(12) United States Patent
Mao et al.

(10) Patent No.: US 11,919,896 B2
(45) Date of Patent: Mar. 5, 2024

(54) [1,2,4]TRIAZOLO[1,5-A]PYRIDINE COMPOUND AS JAK INHIBITOR AND USE THEREOF

(71) Applicant: Zhuhai United Laboratories Co., Ltd., Guangdong (CN)

(72) Inventors: Weiwei Mao, Shanghai (CN);
Wenyuan Qian, Shanghai (CN);
Xuejian Zheng, Shanghai (CN);
Guoping Hu, Shanghai (CN);
Changqing Wei, Shanghai (CN); Jian Li, Shanghai (CN); Shuhui Chen, Shanghai (CN)

(73) Assignee: ZHUHAI UNITED LABORATORIES CO., LTD., Guangdong (CN)

( * ) Notice: Subject to any disclaimer, the term of this patent is extended or adjusted under 35 U.S.C. 154(b) by 575 days.

(21) Appl. No.: 17/263,416

(22) PCT Filed: Aug. 23, 2019

(86) PCT No.: PCT/CN2019/102209
§ 371 (c)(1),
(2) Date: Jan. 26, 2021

(87) PCT Pub. No.: WO2020/038457
PCT Pub. Date: Feb. 27, 2020

(65) Prior Publication Data
US 2021/0155621 A1 May 27, 2021

(30) Foreign Application Priority Data
Aug. 23, 2018 (CN) .......................... 201810968207.6

(51) Int. Cl.
*C07D 471/04* (2006.01)
*A61P 19/02* (2006.01)
(52) U.S. Cl.
CPC ............ *C07D 471/04* (2013.01); *A61P 19/02* (2018.01)
(58) Field of Classification Search
CPC .............................. C07D 471/04; A61P 19/02
See application file for complete search history.

(56) References Cited

U.S. PATENT DOCUMENTS
2009/0220688 A1    9/2009   Morton

FOREIGN PATENT DOCUMENTS

| CN | 102105471 A | 6/2011 |
|---|---|---|
| CN | 108341814 A | 7/2018 |
| WO | 2018019223 A1 | 2/2018 |
| WO | WO2019/036430 | * 2/2019 |

OTHER PUBLICATIONS

International Search Report for Corresponding International Application No. PCT/CN2019/102209 (6 Pages) (dated Sep. 29, 2019).

* cited by examiner

*Primary Examiner* — Samantha L Shterengarts
*Assistant Examiner* — Karen Cheng
(74) *Attorney, Agent, or Firm* — Lucas & Mercanti, LLP

(57) ABSTRACT

Disclosed are a [1,2,4]triazolo[1,5-a]pyridine compound as JAK inhibitor and an application thereof in preparing a drug for treating a disease related to JAK1 or/and TYK2. Specifically, the present invention relates to a compound represented by formula (I), or an isomer or pharmaceutically acceptable salt thereof. (I)

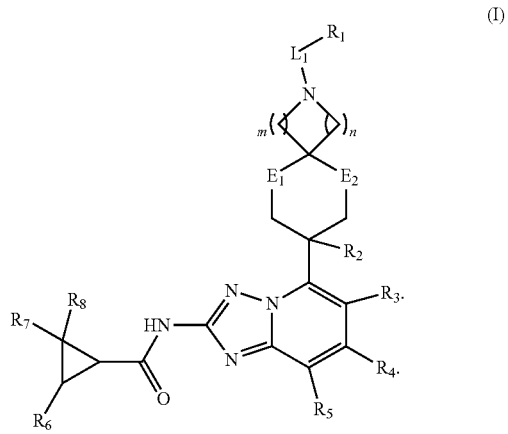

19 Claims, 5 Drawing Sheets

[1,2,4]TRIAZOLO[1,5-A]PYRIDINE COMPOUND AS JAK INHIBITOR AND USE THEREOF

CROSS-REFERENCE TO RELATED APPLICATIONS

This application is a 371 of PCT/CN2019/102209, filed Aug. 23, 2019, which claims the benefit of Chinese Patent Application No. 201810968207.6, filed Aug. 23, 2018.

TECHNICAL FIELD

The present application relates to [1,2,4] triazolo [1,5-a] pyridines compounds as JAK inhibitors, as well as the use thereof for preparing pharmaceuticals for treating diseases associated with JAK1 or/and TYK2. In particular, the present application relates to a compound of formula (I), isomers thereof, or pharmaceutically acceptable salts thereof.

BACKGROUND ART

JAK belongs to tyrosine kinase family which related to inflammations, autoimmune diseases, proliferative diseases, transplant rejection, disease associated with impaired cartilage turnover, congenital cartilage malformation and/or diseases associated with hypersecretion of IL6. The present application further provides the above compound, a method for producing a pharmaceutical composition containing the above compounds, a method for preventing and/or treating inflammations, autoimmune diseases, proliferative diseases, transplant rejection, disease associated with impaired cartilage turnover, congenital cartilage malformation and/or diseases associated with hypersecretion of IL6 by administrating the compounds according to the present application.

Janus kinase (JAK) is a cytoplasmic tyrosine kinase which mediate cytokine signals from a membrane receptor to a STAT transcription factor. Four types of JAK kinases that is, JAK1, JAK2, JAK3 and TYK2, have been described in existing technologies. When a cytokine is combined with its receptor, the members of JAK kinase family are autophosphorylated and/or transphosphorylated with each other, and then STATs phosphorylated, followed by migration into the nucleus to regulate transcription. The JAK-STAT intracellular signals transduction is applicable to interferon, most of interleukins and a variety of cytokines and endocrine factors, such as EPO, TPO, GH, OSM, LIF, CNTF, GM-CSF and PRL (Vainchenker W et al. (2008)).

Study on the combination of genetics model and small molecular JAK inhibitors reveal a few of therapeutic potency of JAKs. JAK3 was identified as an immunosuppressive target by mice and human genetics (O'Shea J. et al. (2004)). JAK3 inhibitors are successfully used in clinical development, initially used for transplant rejection, and later used for other immune inflammation diseases, such as rheumatoid arthritis (RA), psoriasis and Crohn's disease (http://clinicaltrials.gov). It has been proved by genetics and gene knock-out study of mice (Levy D. and Loomis C. (2007)) that TYK2 is potential target for immune inflammation. JAK1 is a new target in the field of immune inflammation diseases. JAK is heterodimerized with other JAKs for transduction with proinflammatory signals driven by transduce cytoplasmic signals. Thus, it predictable that inhibiting JAK1 and/or other JAKs have treatment benefit for a variety of inflammation diseases and/or other diseases driven by signal transduction meditated by JAK.

US2009220688 has disclosed Filgotinib, which is a clinical phase III drug used for rheumatoid arthritis treatment developed by Galapagos.

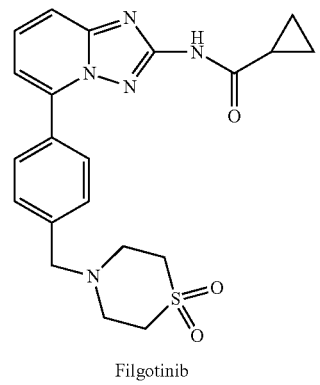 [SMILES: O=C(Nc1nc2cccc(-c3ccc(CN4CCS(=O)(=O)CC4)cc3)n2n1)C1CC1]

Filgotinib

SUMMARY

The present application provides a compound of formula (I), isomers thereof, or pharmaceutically acceptable salts thereof.

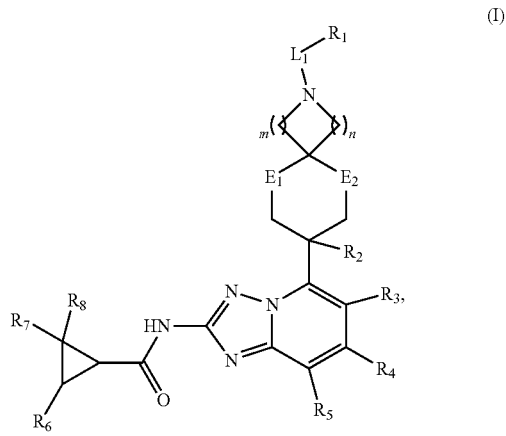

(I)

wherein, $E_1$ and $E_2$ are independently selected from single bond, —$CH_2$— or —$(CH_2)_2$—;

$L_1$ is selected from single bond, —$(CH_2)_g$—, —C(=O)— or —C(=O)—$(CH_2)_h$—;

m is 1 or 2;

n is 1 or 2;

g is 1, 2 or 3;

h is 1, 2 or 3;

$R_1$ is selected from H, CN, $C_{1-6}$ alkyl group or 3~6-membered cycloalkyl groups, in which $C_{1-6}$ alkyl group and 3~6-membered cycloalkyl groups are optionally substituted by one, two or three $R_a$;

$R_2$ is selected from H, F, Cl, Br, I or $C_{1-3}$ alkyl group, in which $C_{1-3}$ alkyl group is optionally substituted by one, two or three $R_b$;

$R_3$, $R_4$ and $R_5$ are independently selected from H, F, Cl, Br, I or $C_{1-3}$ alkyl group, in which $C_{1-3}$ alkyl group is optionally substituted by one, two or three $R_c$;

$R_6$, $R_7$ and $R_8$ are independently selected from H, F, Cl, Br, I or $C_{1-3}$ alkyl group, wherein $C_{1-3}$ alkyl group is optionally substituted by one, two or three $R_d$;

Each of $R_a$ is independently selected from H, F, Cl, Br, I, CN or $C_{1-3}$ alkyl group, wherein $C_{1-3}$ alkyl group is optionally substituted by one, two or three R;

Each $R_b$ is independently selected from F, Cl, Br or I;

Each $R_e$ is independently selected from F, Cl, Br or I;

Each $R_d$ is independently selected from F, Cl, Br or I;

Each R is independently selected from F, Cl, Br or I.

In some embodiments of the present application, each of the above $R_a$ is independently selected from H, F, Cl, Br, I or CN, and other variables are as defined in the present application.

In some embodiments of the present application, the above $R_1$ is selected from H, CN, $C_{1-3}$ alkyl group or 3-5-membered cycloalkyl group, in which the $C_{1-3}$ and 3-5-membered cycloalkyl group are optionally substituted by one, two or three $R_a$, and other variables are as defined in the present application.

In some embodiments of the present application, the above $R_1$ is selected from H, CN, $CH_3$,

in which $CH_3$,

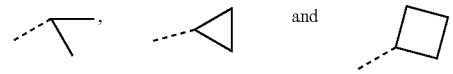

are optionally substituted by one, two or three $R_a$, and other variables are as defined in the present application.

In some embodiments of the present application, the above $R_1$ is selected from H, CN, $CF_3$, $CHF_2$,

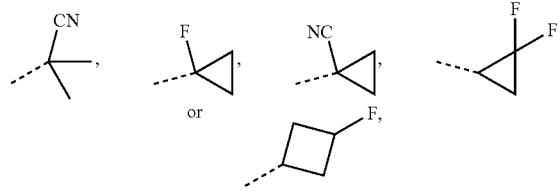

and other variables are as defined in the present application.

In some embodiments of the present application, the above $R_2$ is selected from H, F, Cl, Br or I, and other variables are as defined in the present application.

In some embodiments of the present application, the above $R_3$, $R_4$ and $R_5$ are independently selected from H, F, Cl, Br or I, and other variables are as defined in the present application.

In some embodiments of the present application, the above $R_6$, $R_7$ and $R_8$ are independently selected from H, F, Cl, Br or I, and other variables are as defined in the present application.

In some embodiments of the present application, the above $L_1$ is selected from single bond, —$CH_2$—, —$(CH_2)_2$—, —C(=O)— or —C(=O)—$(CH_2)$—, and other variables are as defined in the present application.

In some embodiments of the present application, the above structure unit

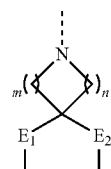

is selected from

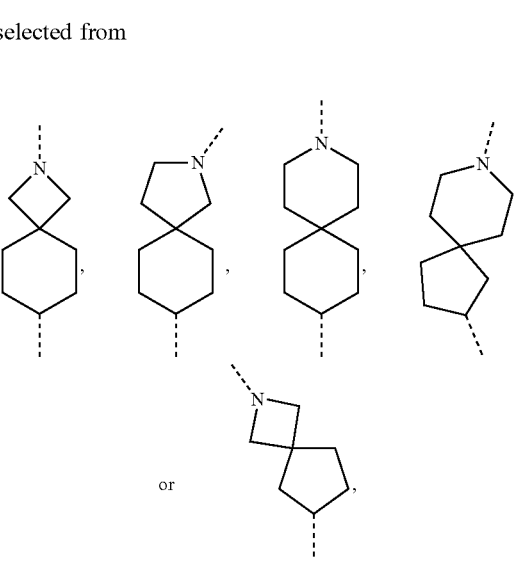

other variables are as defined in the present application.

In some embodiments of the present application, the above structure unit

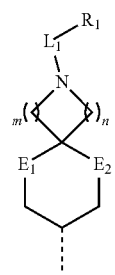

is selected from

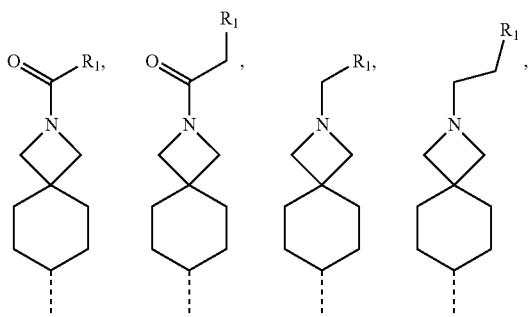

is selected from
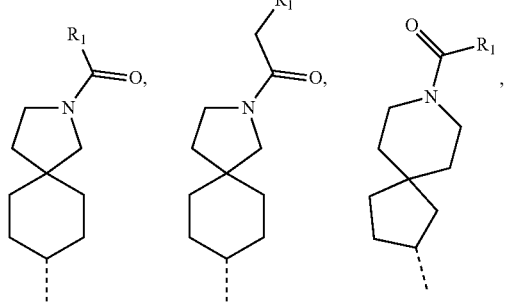
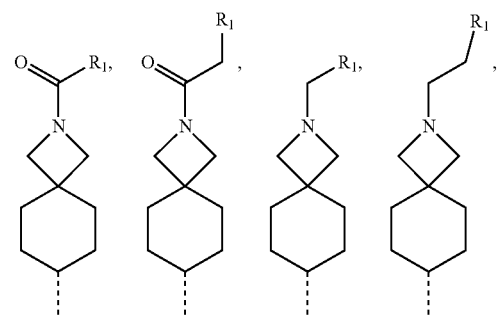
and other variables are as defined in the present application.
In some embodiments of the present application, the above unit
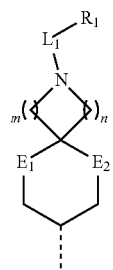
is selected from
and other variables are as defined in the present application.
In some embodiments of the present application, the above structure unit
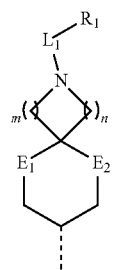

is selected from
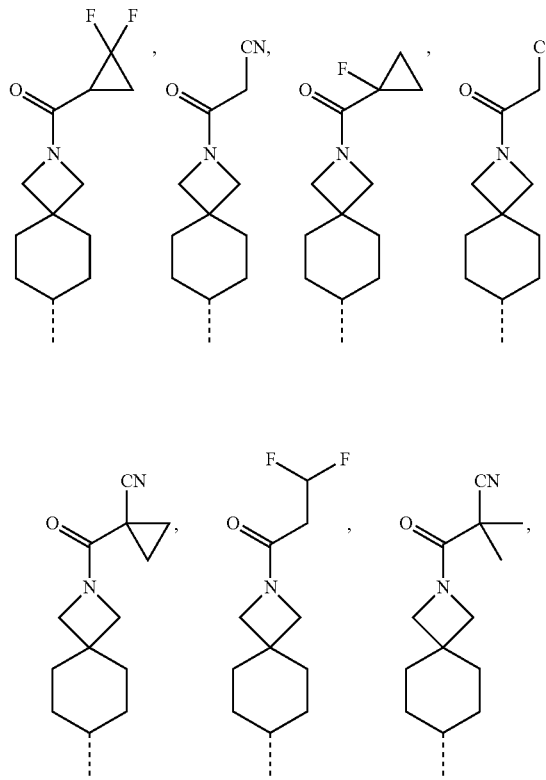
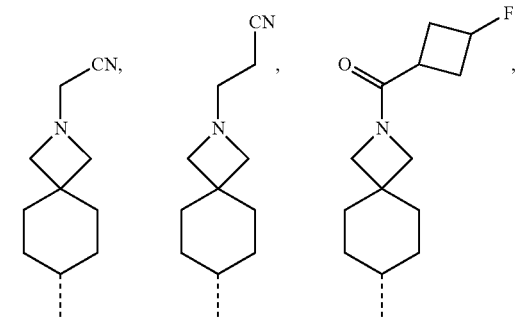
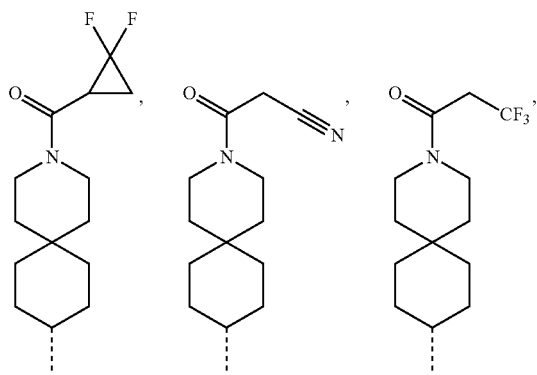
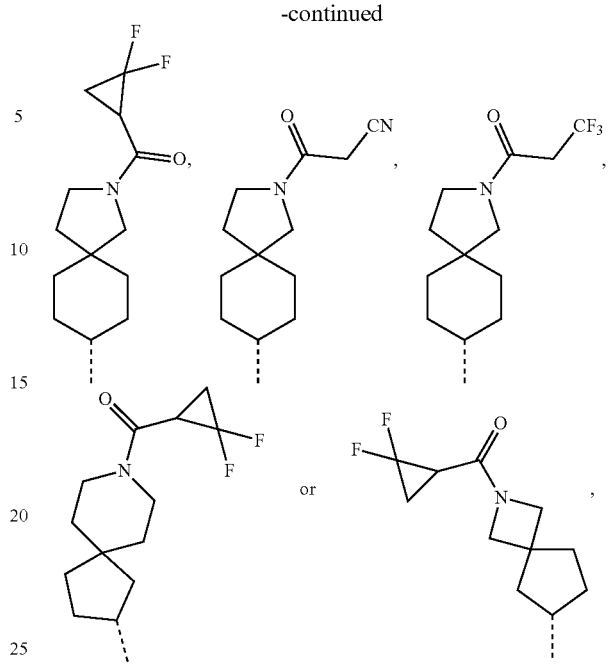
and other variables are as defined in the present application.
There are some embodiments combined from any of the above variables.
In some embodiments of the present application, the above compound of formula (I), isomers thereof, or pharmaceutically acceptable salts thereof, are selected from
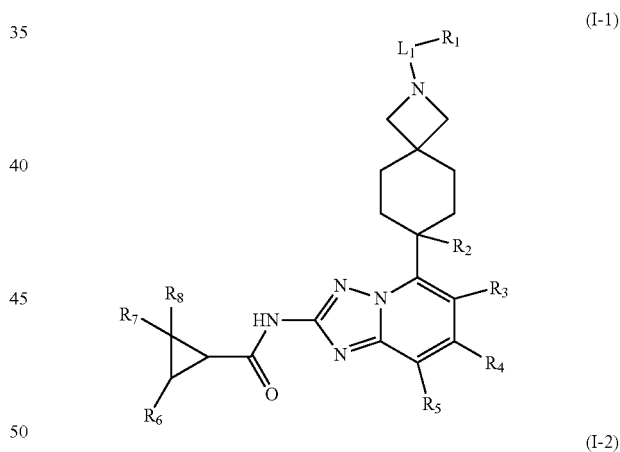
(I-1)
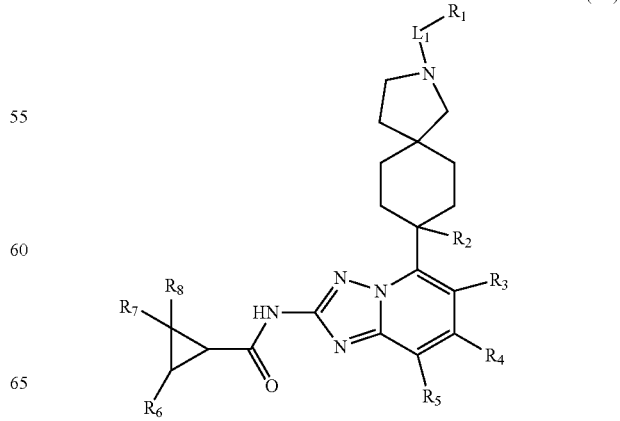
(I-2)

-continued

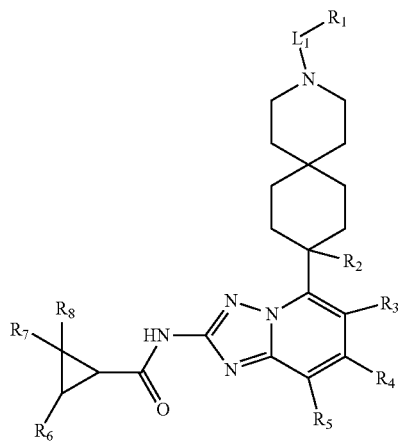
(I-3)

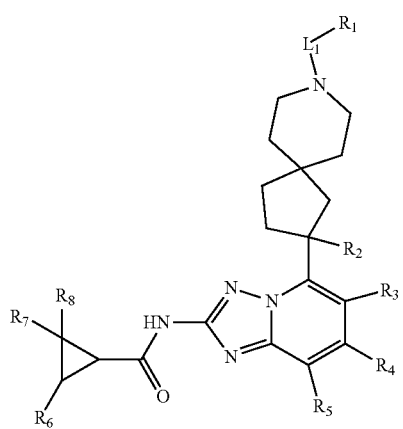
(I-4)

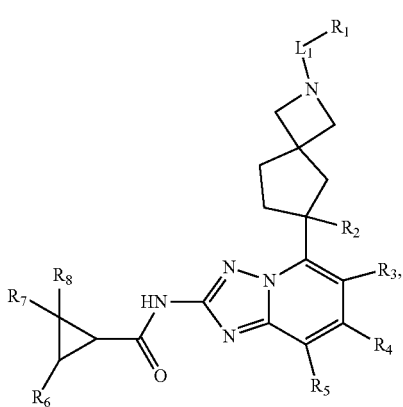
(I-5)

wherein,

L₁, R₁, R₂, R₃, R₄, R₅, R₆, R₇ and R₈ are as defined in the present application.

In some embodiments of the present application, the above compounds of formula (I), isomers thereof, or pharmaceutically acceptable salts thereof, are selected from

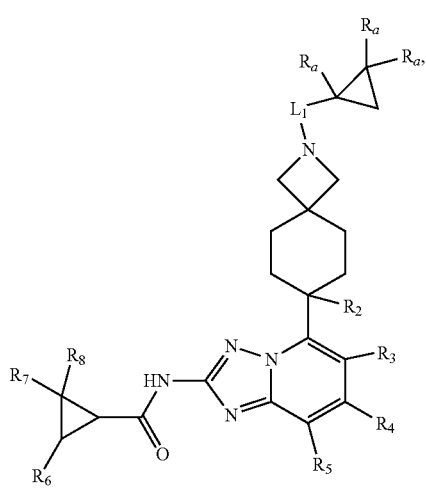
(1-1A)

wherein,

L₁, Rₐ, R₂, R₃, R₄, R₅, R₆, R₇ and R₈ are as defined in the present application.

The present application further provides the following compounds, isomers thereof, or pharmaceutically acceptable salts thereof:

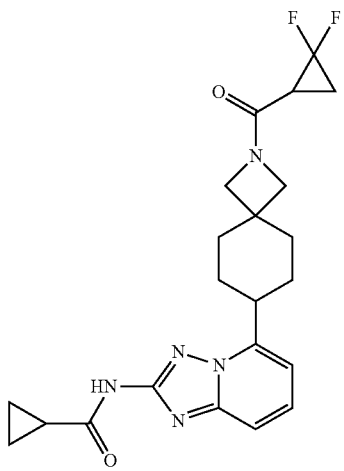

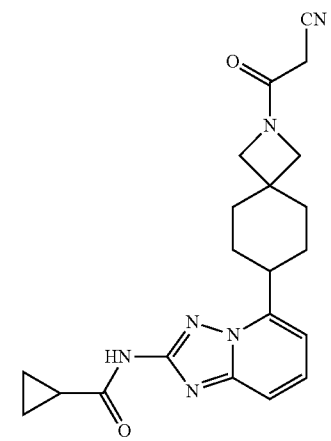

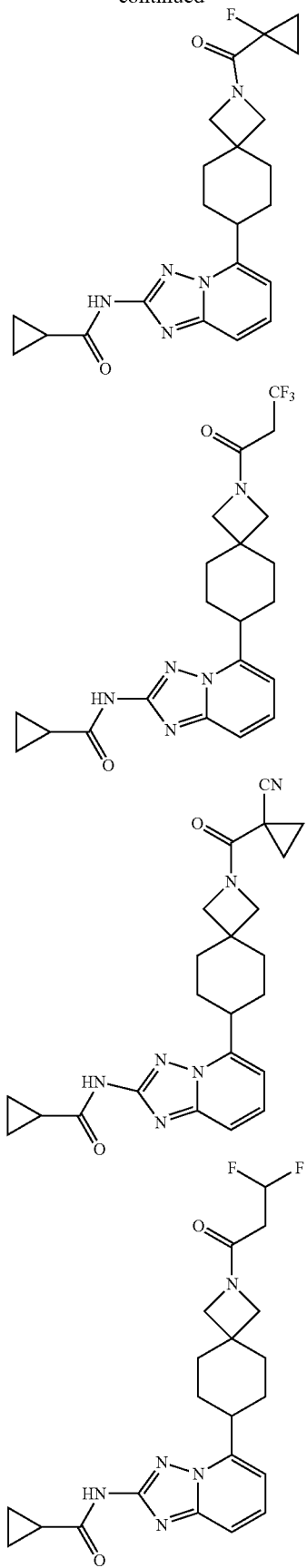

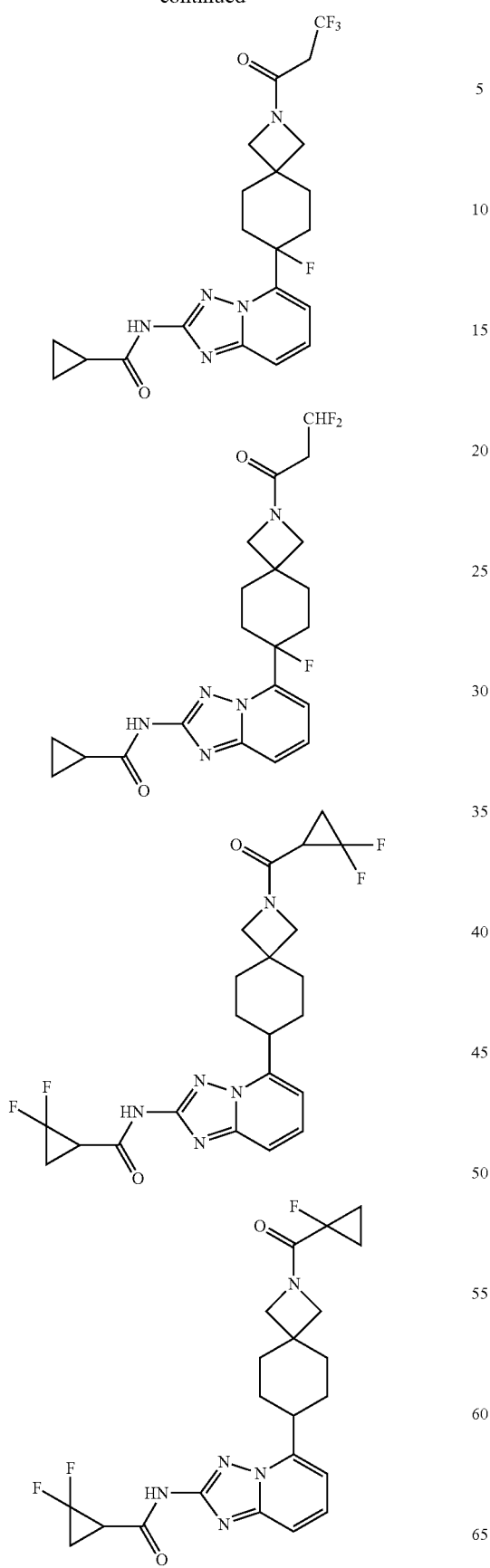
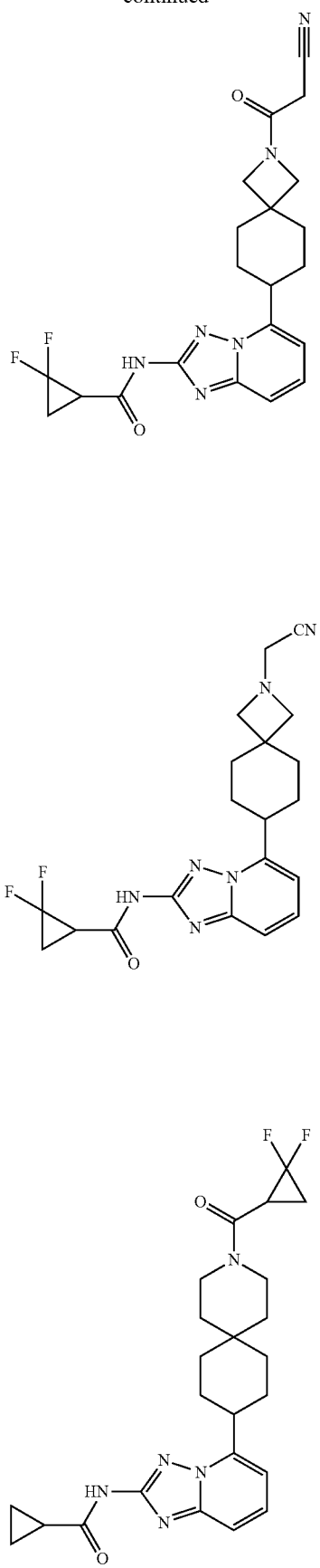

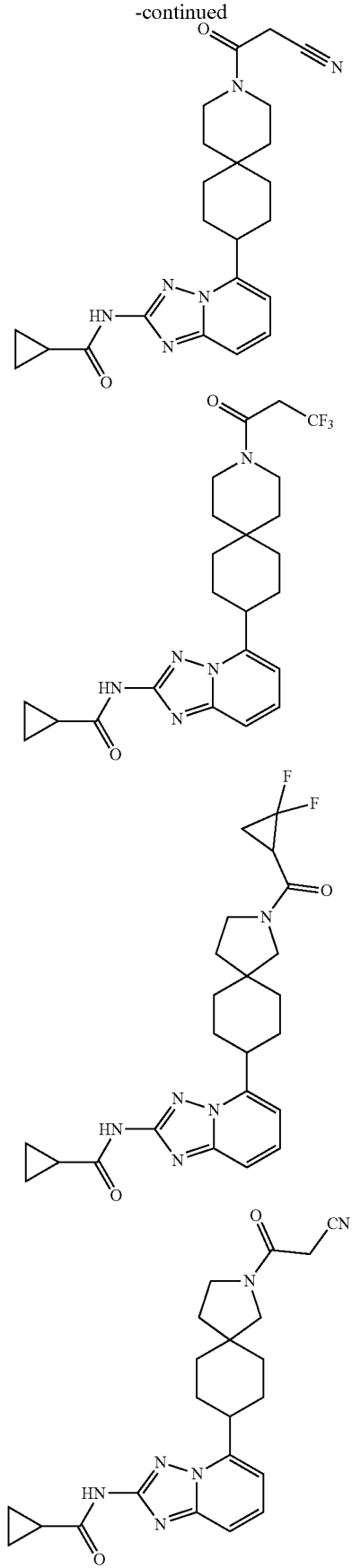
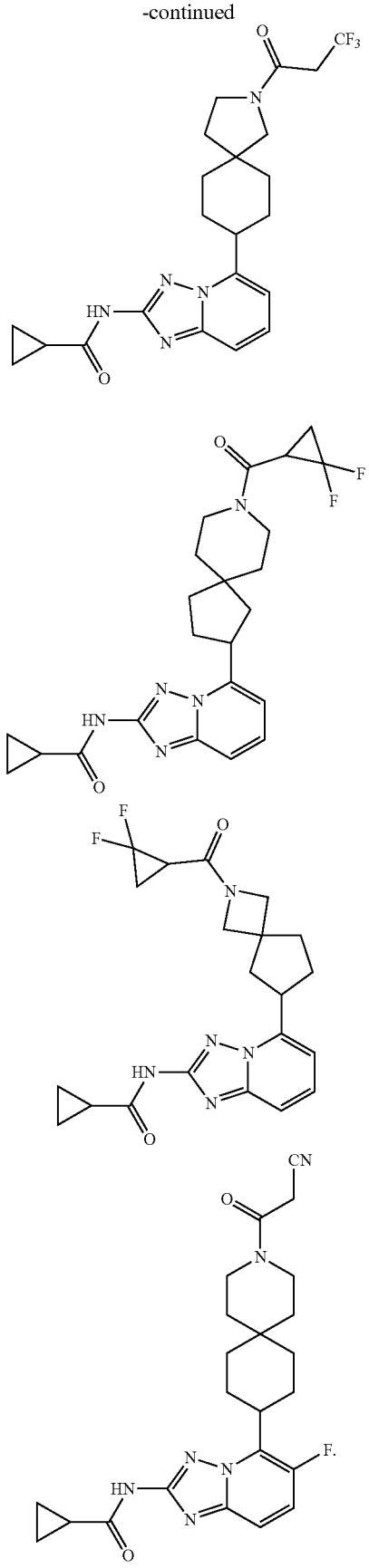

In some embodiments of the present application, the above compound of formula (I), isomers thereof, or pharmaceutically acceptable salts thereof, are selected from
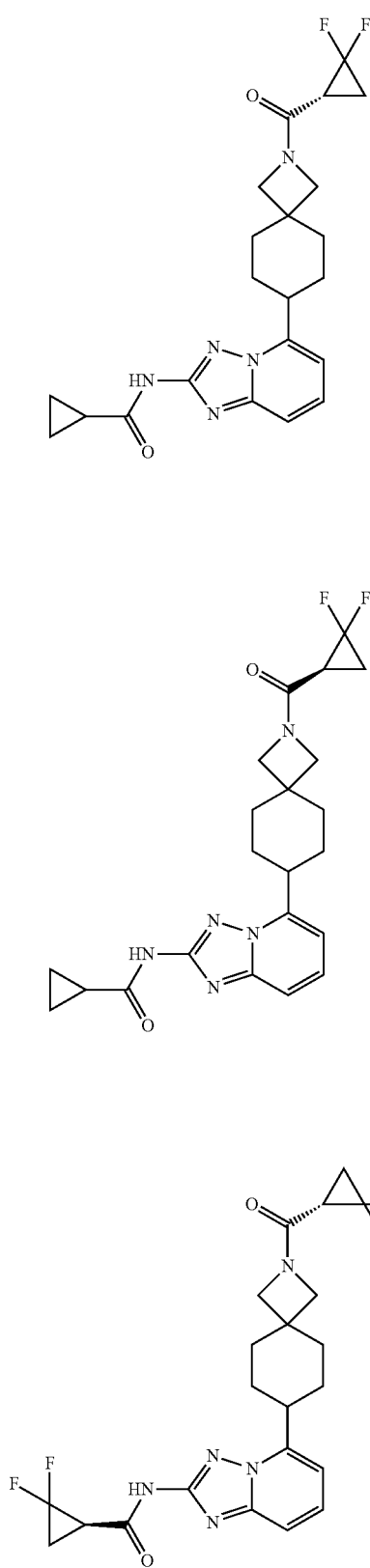
-continued
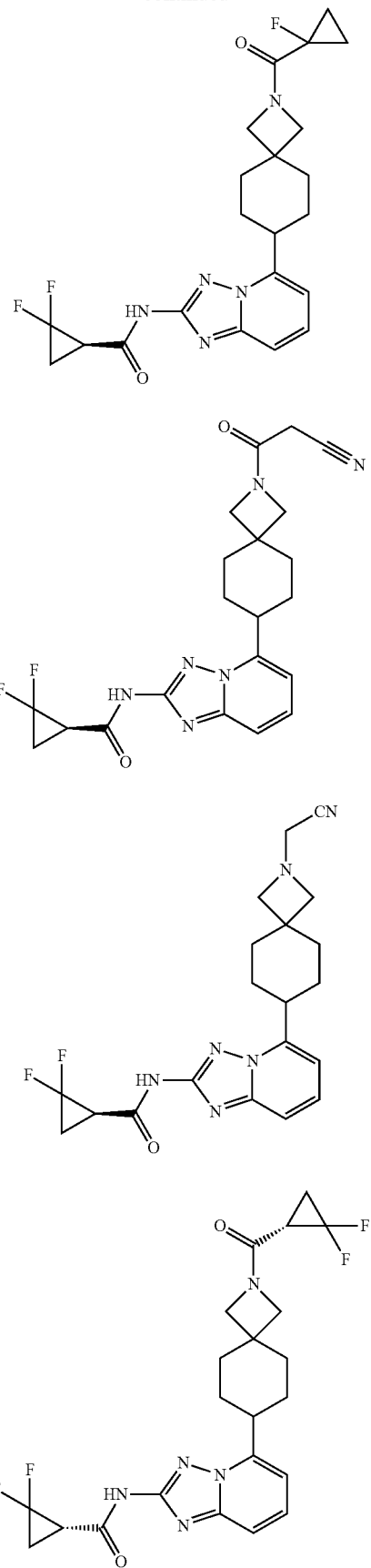

-continued
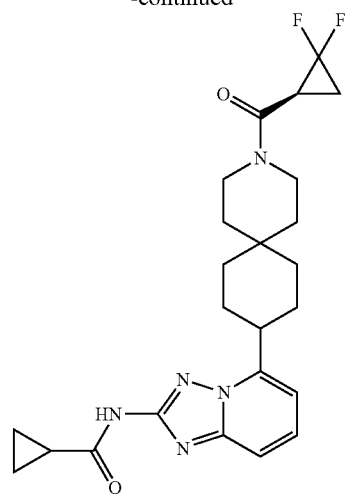
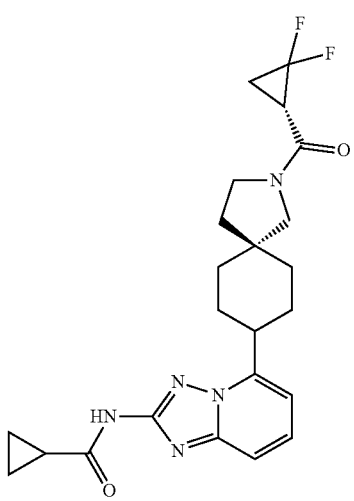
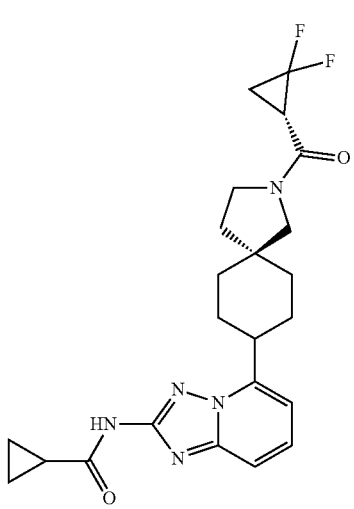
-continued
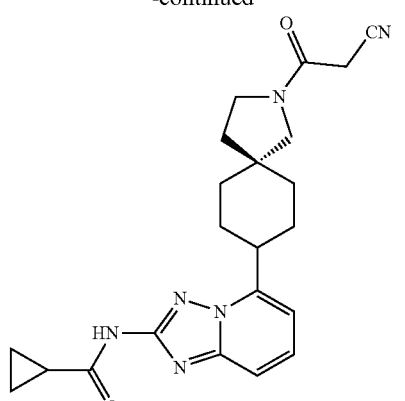
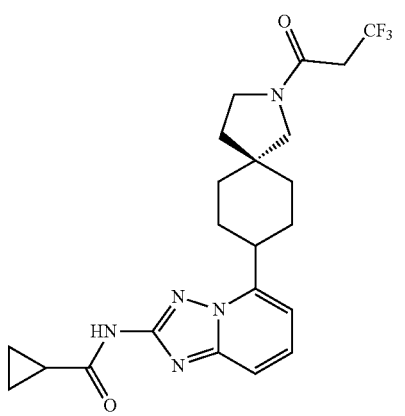
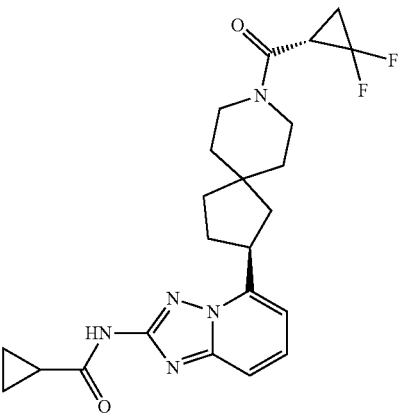
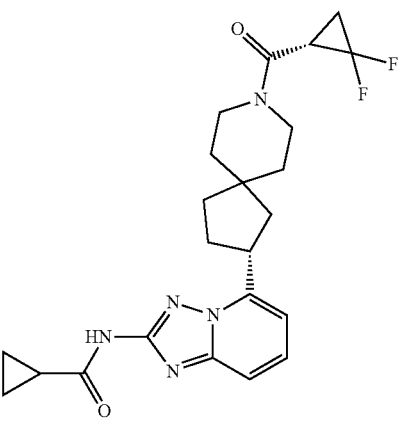

-continued

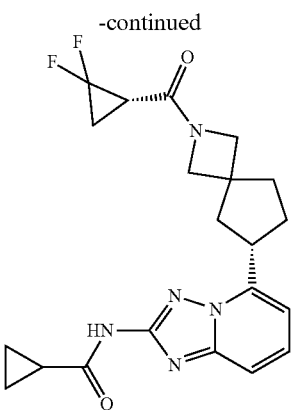

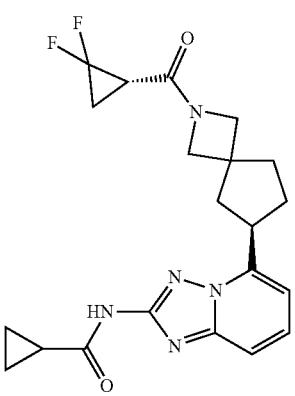

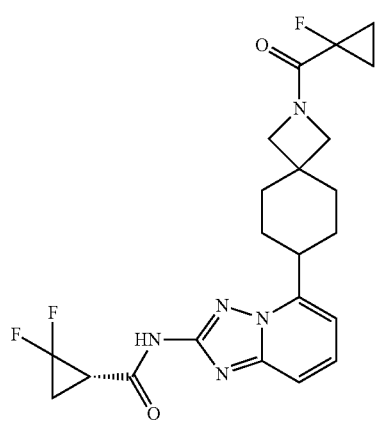

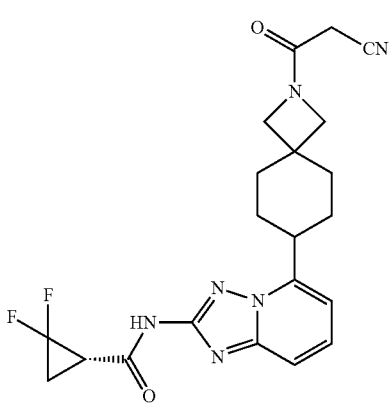

-continued

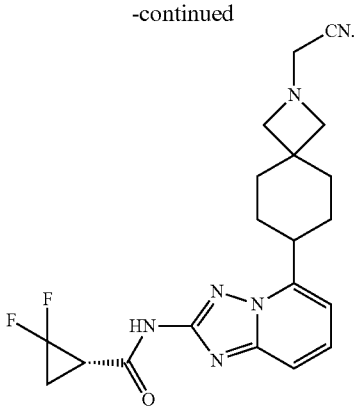

The present application further provides a pharmaceutical composition, which contains therapeutically effective amount of the above compounds, isomers thereof, pharmaceutically acceptable salts thereof or pharmaceutical acceptable carriers thereof as active ingredients.

The present application further provides use of the above compounds or pharmaceutically acceptable salts thereof or pharmaceutical composition thereof in preparing pharmaceuticals for treating diseases related to JAK1 and/or TYK2.

In some embodiments of the present application, the above use is characterized in that the above pharmaceuticals are pharmaceuticals for treatment of rheumatoid arthritis.

Technical Effect

A variety of compounds in the present application have showed good selective inhibit effects to JAK1 and/or TYK2 in the in vitro tests of 4 JAK kinase subtypes (JAK1, JAK2, JAK3 and TYK2), and these compounds show high exposure and good oral bioavailability in pharmacokinetics experiments, which are advantageous for producing good in vivo efficacy.

Definition and Description

Unless otherwise stated, the terms and phrases in the context refer to the following meanings. A specific term or phrase without particular definition should not be considered as uncertain or unclear, and should be considered as their ordinary meanings. When a trade name is mentioned in the context, it refers to its products or active ingredients.

The term "pharmaceutically acceptable" as used here refers to compounds, materials, compositions and/or dosage forms that, within the scope of reliable medical judgment, are suitable for use in contact with human and animal tissues without excessive toxicity, irritation, allergic reaction or other problems or complications, and are commensurate with a reasonable benefit/risk ratio.

The term "pharmaceutically acceptable salt" refers to a salt of the compound in the present application, prepared by compounds from a specific substituent found in the present application and a relatively nontoxic acid or base. When there are relatively acidic functional groups in compounds of the present application, alkali addition salts can be prepared by contacting the neutral form of such compounds with a sufficient amount of alkali in pure solution or suitable inert solvent. Pharmaceutically acceptable alkali addition salts include sodium, potassium, calcium, ammonium, organic amine or magnesium salts and the like. When the compounds of the present application contain relatively alkaline functional groups, acid addition salts can be prepared by contacting the neutral form of such compounds with sufficient amount of acid in pure solution or suitable inert solvent. Examples of pharmaceutically acceptable acid addition salts includes salts derived from mineral acids including hydrochloric acid, hydrobromic acid, nitric acid, carbonic acid, bicarbonate acid, phosphoric acid, monohydrogen phosphate, dihydrogen phosphate, sulfuric acid, hydrosulfate, hydroiodic acid, phosphorous acid, etc; salts derived from organic acids including acetic acid, propionic acid, isobutyric acid, maleic acid, malonic acid, benzoic acid, succinic acid, octanedioic acid, fumaric acid, lactic acid, mandelic acid, phthalic acid, benzenesulfonic acid, para-toluenesulfonic acid, citric acid, tartaric acid, methanesulfonic acid and the like; and slats derived from amino acid (e.g. arginin), and salts from organic acids such as glucuronic acid and the like. Some specific compounds in the present application contain alkaline and acidic functional groups, and thus can be translated to any alkali or acid addition salts.

Pharmaceutical acceptable salts in the present application can be prepared from a parent compound which has acid radical or basic group by conventional chemical methods. In general, a method for preparing such salts includes preparing them by reacting these compounds in the form of free acids or bases with appropriate stoichiometric bases or acids in water or organic solvents or a mixture thereof.

Compounds in the present application can be present as the form of specific geometrical isomer or stereoisomer. Compounds conceived in the present application include cis- and trans-isomers, (−)- and (+)-enantiomers, (R)- and (S)-enantiomers, diastereoisomers, (D)-isomers, (L)-isomers, as well as their racemic mixtures and other mixtures, such as mixtures of enantiomers and diastereoisomers, all of which are included in the scope of the present application. Other asymmetric carbon atoms may be present in substituents such as alkyl groups. All these isomers and their mixtures are included in the scope of the present application Unless otherwise stated, the terms "enantiomer" or "optical isomer" are stereoisomers which are mirror images to each other.

Unless otherwise stated, the terms "cis-trans-isomer" or "geometrical isomer" are formed because double bonds or single bonds of a ring-forming carbon atom cannot rotate freely.

Unless otherwise stated, the term "diastereoisomer" refers to molecules which have two or more chiral centers, and are stereoisomers without mirror-image relation between the molecules.

Unless otherwise stated, "(D)" or "(+)" refers to right-handed rotation, "(L)" or "(−)" refers to left-handed rotation, "(DL)" or "(±)" refers to racemic.

Unless otherwise stated, a wedge-shape full line bond (◥) and wedge-shape dotted line bond (⋰) represents an absolute configuration of stereocenter, a straight solid line bond (◢) and straight dotted line (⋰) represents relative configuration of stereocenter, a wavy line (∿) represents wedge-shape solid line bond (◢) or wedge-shape dotted line bond (⋰), or a wavy line (∿) represents straight solid line bond (◢) and straight dotted line (⋰).

Unless otherwise stated, when there are double bonds in the compounds, such as C═C double bonds, C═N double bonds and N═N double bonds, and the atoms on the double bonds are connected to two different substituent groups (in double bonds containing nitrogen atoms, a pair of lone electrons on the nitrogen atom are considered as a connected substituent group), if the atoms on double bonds of compounds are connected to their substituent groups with a wavy line (∿), it is considered as a (Z) isomer, an (E) isomer, or mixture of both of the compounds. For example, the following formula (A) represents that the compound exists as a single isomer of formula (A-1) or formula (A-2), or a mixture of two isomers of formula (A-1) and formula (A-2); the following formula (B) represents that the compound exists in the form of a single isomer of formula (B-1) or formula (B-2), or a mixture of two isomers of formula (B-1) and formula (B-2). The following formula (C) represents that the compound exists in the form of a single isomer of formula (C-1) or formula (C-2), or a mixture of two isomers of formula (C-1) and formula (C-2).

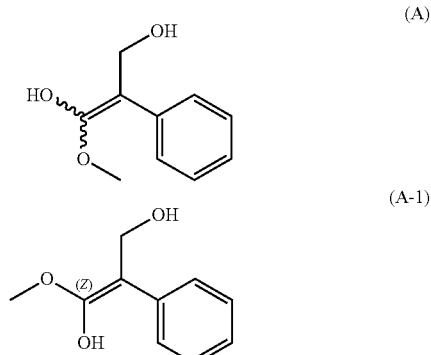

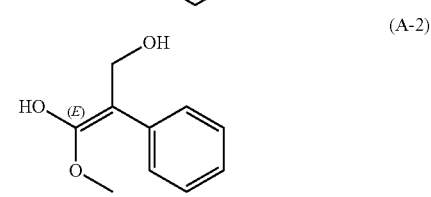

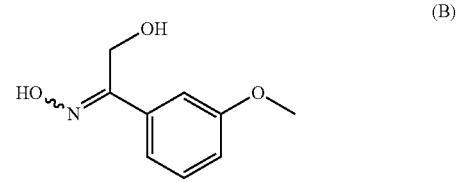

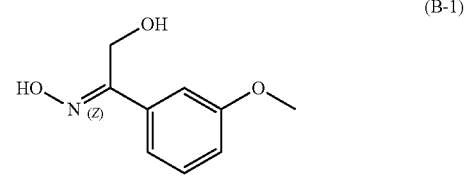

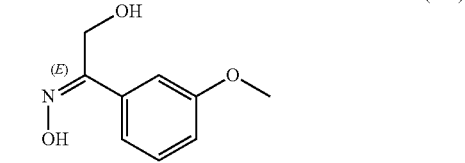

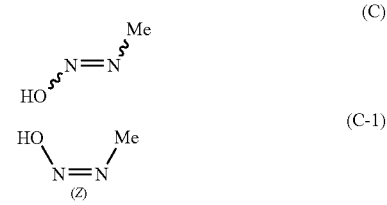

-continued

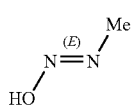
(C-2)

Unless otherwise stated, the term "tautomer" or "tautomer form" means different functional groups isomers can keep dynamic equilibrium, and can be mutually converted at room temperature. When tautomers are available (e.g. in solution), there can be chemical equilibrium of the tautomers. For example, proton tautomers (also called prototropic tautomer) include mutually conversion by protolysis, such as keto-enol tautomerism and imine-enamine tautomerism. Valence tautomers include mutually conversion by some recombination of bonding electrons. In particular, a specific example is mutually conversion of pentane-2,4-dione and 4-hydroxyamyl-3-en-2-one tautomers.

Unless otherwise stated, the terms "rich in a isomer", "isomer enrichment", "rich in an enantiomer", "enantiomer enrichment" means that the content of one of these isomers or enantiomers is less than 100%, and the content of such isomer or enantiomer is more than or equal to 60%, or more than or equal to 70%, or more than or equal to 80%, or more than or equal to 90%, or more than or equal to 95%, or more than or equal to 96%, or more than or equal to 97%, or more than or equal to 98%, or more than or equal to 99%, or more than or equal to 99.5%, or more than or equal to 99.6%, or more than or equal to 99.7%, or more than or equal to 99.8%, or more than or equal to 99.9%.

Unless otherwise stated, the terms "excess isomer" or "excess enantiomer" refer to the differences between relatively percentages of two isomers or enantiomers. For example, the content of an isomer or enantiomer is 90%, while the content of another isomer or enantiomer is 10%, then the value (ee value) of excess isomer or enantiomer is 80%.

Optically active (R)- and (S)-isomers and D and L isomers can be prepared by chiral synthesis or chiral reagents or other conventional techniques. If an enantiomer of a compound of the present application is desired, it can be prepared by asymmetric synthesis or derivatization with a chiral promoter, in which the resulting diastereomer mixture is separated and the auxiliary group is split to provide the desired pure enantiomer. Alternatively, when the molecule contains an alkaline functional group (such as an amino group) or an acidic functional group (such as a carboxyl group), a salt of the diastereomer is formed with an appropriate optically active acid or base, and then the diastereomer is separated by a conventional method known in the art, and then the pure enantiomer is recovered. In addition, the separation of enantiomers and diastereomers is usually accomplished by using chromatography, which uses a chiral stationary phase and is selectively combined with chemical derivatization (e.g., from amines to carbamates). The compound of the present application may contain an unnatural proportion of atomic isotopes on one or more atoms constituting the compound. For example, compounds can be labeled with radioisotopes, such as tritium ($^3$H), iodine-125 ($^{125}$I), or C-14 ($^{14}$C). For example, heavy hydrogen can be used to replace hydrogen to form deuterated drugs. The bond formed by deuterium and carbon is stronger than that formed by ordinary hydrogen and carbon. Compared with undeuterated drugs, deuterated drugs have the advantages of reducing side effects, increasing drug stability, enhancing curative effect and prolonging the biological half-life of drugs. The transformation of all isotopic compositions of the compound of the present application, whether radioactive or not, is included in the scope of the present application. "Optional" or "optionally" means an event or condition that may, but is not necessarily, subsequently described, and such description includes the circumstances in which the event or condition occurs and the circumstances in which the event or condition does not occur.

The term "substituted" refers to the substitution of any one or more hydrogen atoms on a specific atom by a substituent, which can include heavy hydrogen and hydrogen variants, provided that the valence state of the specific atom is normal and the substituted compound is stable. When the substituent is oxygen (i.e. =O), it means that two hydrogen atoms are substituted. Oxygen substitution does not occur on aromatic groups. The term "optionally substituted" means that it can be substituted or not substituted. Unless otherwise specified, the type and number of substituents may be optional on the basis of chemical implementability.

When any variable (e.g. R) exists more than once in the composition or structure of a compound, its definition is independent in each case. Thus, for example, if a group is substituted by 0-2 R, the group can be optionally substituted by at most two R, and the R in each case has an independent option. In addition, combinations of substituents and/or their variants are permitted only if such combinations produce a stable compound.

When the number of a linking group is 0, such as —(CRR)$_0$—, the linking group is a single bond.

When one of the variants is selected from a single bond, it means that the two linking groups are directly linked. For example, when L represents single bond, the structure of A-L-Z is A-Z in fact.

When a substituent is vacant, it means that the substituent does not exist. For example, when X in A-X is vacant, it means that the structure is actually A. When the listed substituents do not indicate which atom is connected to the substituted group, the substituent can be bonded by any atom of the substituent. For example, pyridinyl group as substituent can be connected to the substituted group by any carbon atom on the pyridine ring.

When the listed linking groups does not indicate its connection direction, the connection direction is optional. For example, when the connecting group L in

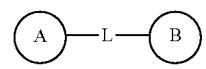

is -M-W—, -M-W— can connect rings A and B in the same direction as reading from left to right to form

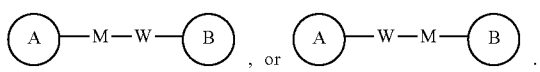

connect rings A and B in the opposite direction as reading from left to right to form The combination of the linking groups, substituents and/or variants thereof is permitted only if such combination produces a stable compound.

Unless otherwise stated, the numbers of the atoms on the rings are identified as numbers of members of rings, such as "5-7-membered ring" refers to a ring with 5-7 atoms surrounding arranged.

Unless otherwise specified, "5-6-membered ring" means cycloalkyl, heterocycloalkyl, cycloalkenyl, heteroalkenyl, cycloalkynyl, heterocycloalkynyl, aryl or heteroaryl consisting of 5 to 6 ring atoms. The ring includes a single ring, and also a double ring system such as a spiral ring, a combined ring and a bridge ring. Unless otherwise specified, the ring optionally contains 1, 2, or 3 heteroatoms independently selected from O, S, and N. The 5-6-membered ring includes 5-element ring, 6-element ring, etc. "5-6-membered ring" includes, for example, phenyl, pyridyl, piperidinyl, etc.; on the other hand, the term "5-6 membered heterocyclic alkyl" includes piperidinyl, etc., but does not include phenyl. The term "ring" also includes a system of rings containing at least one ring, each of which independently conforms to the above definition.

Unless otherwise stated, the term "$C_{1-6}$ alkyl group" refers to unbranched or branched saturated hydrocarbon groups consisting of 1 to 6 carbon atoms. The $C_{1-6}$ alkyl group include $C_{1-5}$, $C_{1-4}$, $C_{1-3}$, $C_{1-2}$, $C_{2-6}$, $C_{2-4}$, $C_6$ and $C_5$ alkyl groups, etc., which can be monovalence (e.g. methyl), bivalence (e.g. methylene), or multivalence (e.g. methyne). The examples of $C_{1-6}$ alkyl group include but, not limited to, methyl (Me), ethyl (Et), propyl (include n-propyl and isopropyl), butyl (including n-butyl, isobutyl, s-butyl and t-butyl), pentyl (including n-pentyl, isopentyl and neopentyl), hexyl, etc.

Unless otherwise stated, the term "$C_{1-3}$ alkyl group" refers to unbranched or branched saturated hydrocarbon groups consisting of 1 to 3 carbon atoms. The described $C_{1-3}$ alkyl group includes $C_{1-2}$ and $C_{2-3}$ alkyl groups, etc., which can be of monovalence (e.g. methyl), divalence (e.g. methylene), or multivalence (e.g. methyne). The examples of $C_{1-3}$ alkyl groups include, but not limited to, methyl (Me), ethyl (Et), propyl (include n-propyl and isopropyl), etc.

Unless otherwise stated, "$C_{3-6}$ cycloalkyl group" refers to saturated cyclic hydrocarbon groups, including monocyclic and bicyclic systems. The $C_{3-6}$ cycloalkyl group includes $C_{3-5}$, $C_{4-5}$ and $C_{5-6}$ cycloalkyl group, etc., which can be of monovalence, divalence or multivalence. The examples of $C_{3-6}$ cycloalkyl group includes, but not limited to, cyclopropyl, cyclobutyl, cyclopentyl, cyclohexyl, etc.

Unless otherwise stated, $C_{n-n+m}$ or $C_n-C_{n+m}$ includes any specific circumstances with n to n+m carbon, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and further includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc. Similarly, n-membered to n+m-membered means that the numbers of atoms on a ring are n to n+m, for example, a 3-12-membered ring includes 3-membered rings, 4-membered rings, 5-membered rings, 6 membered-rings, 7-membered rings, 8-membered-ring, 9-membered rings, 10-membered rings, 11-membered rings, and 12-membered rings, and further includes any range from n to n+m, for example, a 3-12-membered ring including 3-6-membered rings, 3-9-membered rings, 5-6-membered rings, 5-7-membered rings, 6-7-membered rings, 6-8-membered rings, and 6-10-membered rings, etc.

The compounds of the present application can be prepared by a variety of synthesis methods well known to those skilled in the art, including the specific embodiments listed below, the embodiments formed by the combination of the compounds with other chemical synthesis methods, and the equivalent substitution methods well known to those skilled in the art. The preferred embodiments include, but not limited to, the embodiments of the present application.

The solvent used in the present application is commercially available. The present application adopts the following abbreviations: aq for water; HATU for O-(7-azabenzotriazole-1-yl)-N,N,N',N'-tetramethylurea hexafluorophosphate; EDC for N-(3-dimethylaminopropyl)-N'-ethylcarbodiimide hydrochloride; m-CPBA for 3-chloroperoxybenzoic acid; EQ for equivalent or equal amount; CDI for carbonyl diimidazole; DCM for dichloromethane; PE for petroleum ether; DIAD for diisopropyl azodicarboxylate; DMF For N, N-dimethylformamide; DMSO for dimethyl sulfoxide; EtOAc for ethyl acetate; EtOH for ethanol; MeOH for methanol; CBz for benzyloxycarbonyl, an amine protecting group; BOC for tert butoxycarbonyl, an amine protecting group; HOAc for acetic acid; $NaCNBH_3$ for epicyanoberbohydride; R.T. for room temperature; O/N for overnight; THF for tetrahydrofumn; $Boc_2O$ for di-tert-butyl dicarbonate; TFA for trifluoroacetic acid; DIPEA for diisopropylethylamine; $SOCl_2$ for sulfoxide chloride; $CS_2$ for carbon disulfide; TsOH for p-toluenesulfonic acid; NFSI for N-fluoro-N-(phenylsulfonyl) benzene sulfonamide; NCS for 1-chloropyrrolidine-2,5-dione; $n-Bu_4NF$ for tetrabutylammonium fluoride; iPrOH for 2-propanol; mp for melting point; LDA for diisopropylaminolithium; Pd (dppf) $Cl_2 \cdot CH_2Cl_2$ for dichloromethane complex of [1,1'-bis (diphenylphosphino) ferrocene] palladium dichloride; DIEA for N,N-diisopropyl ethylamine; IPA for isopropanol; HOBt for 1-hydroxybenzotriazole; LiHIDS for hexamethyldisilicylaminolithium; TEA for triethylamine; HEPES for 4-hydroxyethyl piperazine ethanesulfonic acid; LiHMDS for hexamethyldisilicylaminolithium; EDCI for carbodiimide; Pd/C for palladium carbon; METHANOL for methanol; KOAc for potassium acetate; $K_2CO_3$ for potassium carbonate.

Compounds are manually named or by ChemDraw® Software, and commercially available compounds are named by supplier catalog name.

DETAILED DESCRIPTION

Figure 1:
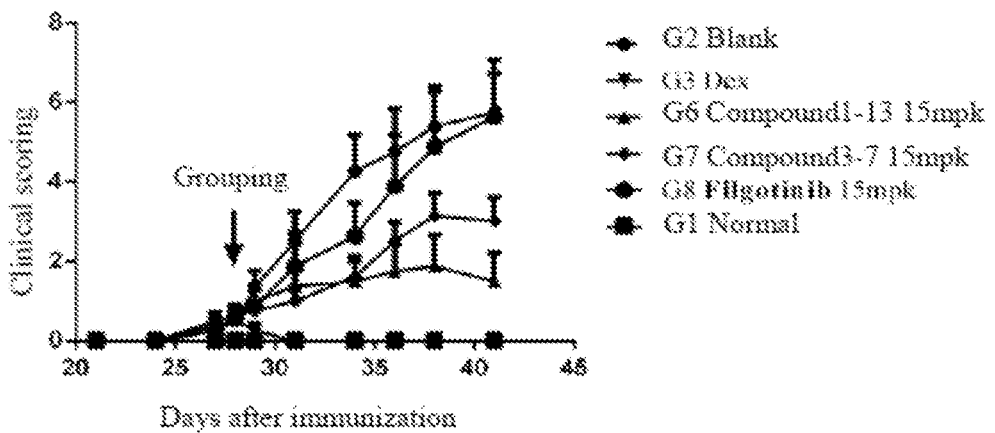
FIG. 1 The average clinic scorings of mice with arthritis.

The present application will be described in detail by the embodiments below, but it is not intended to impose any adverse limitation to the present application. The present application is described in detail herein, and specific embodiments are also disclosed. It will be apparent to those skilled in the art to make various changes and improvements to the specific embodiments of the present application without departing from the spirit and scope of the present application.

Example 1

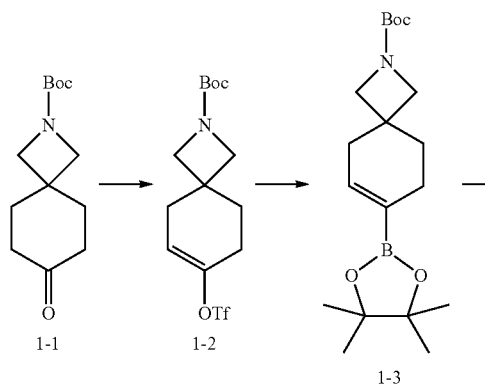

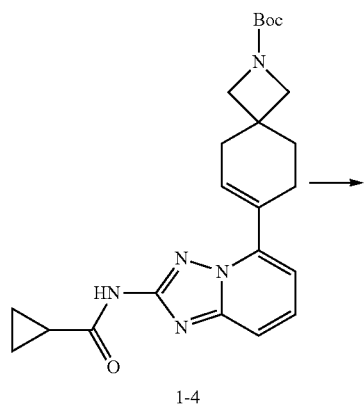

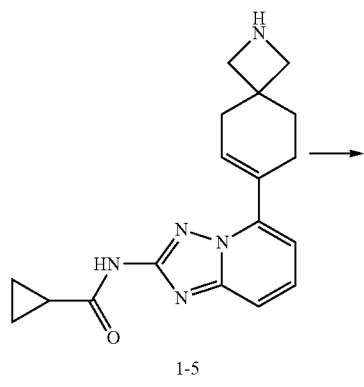

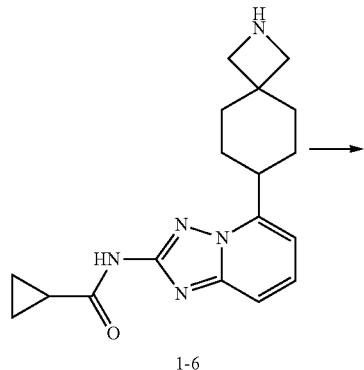

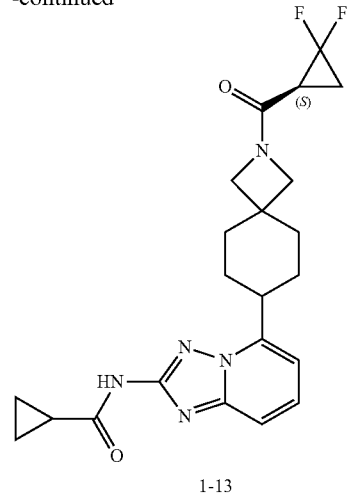

Step 1: LiHMDS (1 M, 51.2 mL) were dripped into THF (150 mL) solution containing compound 1-1 (10.2 g, 42.6 mmol) at −78° C. After stirring the reaction solution for 1 hour at −78° C., THF (150 mL) solution containing 1,1,1-trifluoro-N-phenyl-N-(trifluoromethanesulfonyl) methanesulfonamide (16.7 g, 46.9 mmol) was added to the reaction solution, and then stirred for 12 hours at 15° C. TLC (PE:EA=10:1) showed the raw materials were consumed completely, and there were new points generated. The solution was quenched by using 250 mL saturated ammonium chloride, diluted by 200 mL water, and then extracted with EtOAc (200 mL*3). Organic phases were combined, washed by saturated saline solution, dried by sodium sulfate, filtered and concentrated to provide the compound 1-2. Coarse product was used in the following reactions without purification. $^1$H NMR (400 MHz, CDCl$_3$) δ 5.63 (br s, 1H), 3.50-3.65 (m, 4H), 2.34 (br s, 4H), 1.88 (br t, J=5.90 Hz, 2H), 1.37 (s, 9H).

Step 2: Potassium acetate (12.7 g, 129.3 mmol) and Pd(dppf)Cl$_2$·CH$_2$Cl$_2$ (3.5 g, 4.3 mmol) were added to DMF (100 mL) solution containing compound 1-2 (16 g, 43.1 mmol) and bis(pinacolato)diboron (12.0 g, 47.4 mmol), then replaced with nitrogen for 3 times, and stirred in nitrogen condition for 3 hours at 70° C. TLC showed the raw materials are consumed completely, and there were new points generated. The reaction solution was dispersed in a mixture of 300 mL water and 400 mL EtOAc. Organic phases were separated, washed by saturated saline solution, dried by sodium sulfate, filtered and concentrated to provide a coarse product. The coarse product was purified by silica gel column chromatography to provide compound 1-3. H NMR (400 MHz, CDCl$_3$) δ 6.46 (br s, 1H), 3.71-3.53 (m, 4H), 2.31 (br d, J=3.0 Hz, 2H), 2.24-2.16 (m, 2H), 1.74 (t, J=6.3 Hz, 2H), 1.44 (s, 9H), 1.26 (s, 12H).

Step 3: In a nitrogen atmosphere, potassium carbonate (3.8 g, 27.3 mmol) and Pd(dppf)Cl$_2$·CH$_2$Cl$_2$ (744 mg, 911.0 μmol) were added into the solution of dioxane (60 mL) and water (15 mL) containing compound 1-3 (3.5 g, 10.0 mmol) and N-(5-bromo-[1,2,4]triazolo[1,5-a]pyridine-2-yl) cyclopropane formamide (2.6 g, 9.1 mmol). This reaction solution was stirred for 3 hours at 90° C. LCMS showed the raw materials were consumed completely, and there were target molecular ion peaks detected. The reaction solution was concentrated to provide a coarse product, which was purified and separated by chromatography to provide compound 1-4. LCMS (ESI) m/z: 424.3[M+H]+.

Step 4: Dichloromethane (10 mL) solution containing compound 1-4 (3.5 g, 8.2 mmol) was added with hydrochloric acid/EtOAc (4 M, 30 mL), and stirred for 0.5 hour at 25° C. LCMS showed raw materials were consumed completely, and target molecular ion peaks were detected. Solid was precipitated, filtered and dried to provide compound 1-5 (3.3 g hydrochloride, coarse product), then directly used in following reactions without purification. LCMS (ESI) m/z: 324.1.

Step 5: In a nitrogen atmosphere, Pd/C (1 g, 10%) was added into methanol (100 mL) solution containing compound 1-5 (3.0 g, 8.34 mmol, hydrochloride). The suspension was replaced with hydrogen for 3 times, then stirred for 12 hours in hydrogen (30 psi) atmosphere at 30° C. LCMS showed raw materials were consumed completely, and target molecular ion peaks are detected. The reaction solution was filtered, then concentrated to provide compound 1-6. LCMS (ESI) m/z: 326.2 [M+H]+

Step 6: Compound 1-6 (0.87 g, 2.40 mmol, hydrochloride) was dissolved in N,N-dimethyl formamide (10 mL), added with HOBt (487 mg, 3.6 mmol) and EDCI (691 mg, 3.6 mmol), then added with (1S)-2,2-difluoro cyclopropanecarboxylic acid (323 mg, 2.6 mmol) and ethyldiisopropylamine (621 mg, 4.8 mmol), and left for reacting for 12 hours at 15° C. LC-MS showed reaction was complete. The reaction solution was concentrated under reduced pressure, and residues were processed by preparative HPLC (neutral system) to provide compound 1-13: $^1$H NMR (400 MHz, METHANOL-d$_4$) δ 7.32-7.73 (m, 2H), 6.95 (br s, 1H), 3.62-4.22 (m, 4H), 3.45 (br s, 1H), 3.18-3.37 (m, 1H), 2.61 (br s, 1H), 1.45-2.27 (m, 10H), 0.78-1.17 (m, 4H). LCMS (ESI) m/z: 430.0[M+H]+.

The following compounds having the following characteristic data were obtained from compound 1-6 as common intermediate by using the same synthesis and separation methods as those used for compound 1-13 (i.e. carboxylic acids for synthesizing compound 1-13 were replaced by carboxylic acids corresponding to the following target molecules at acid amide condensation reactions):

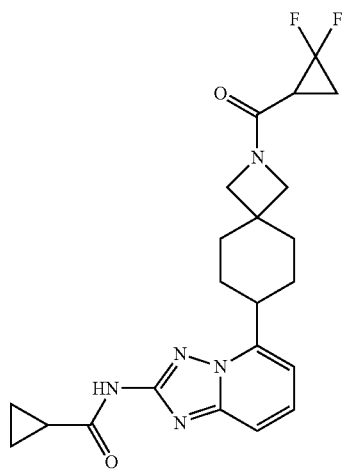

1-7

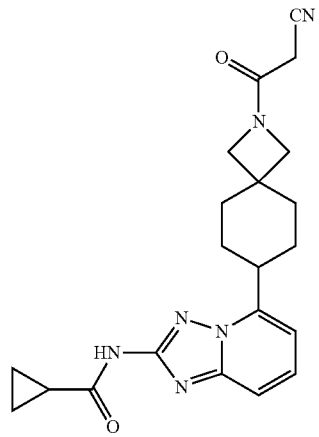

1-8

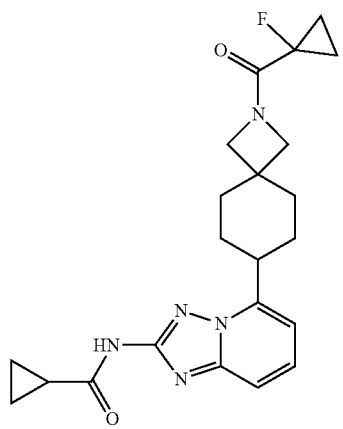

1-9

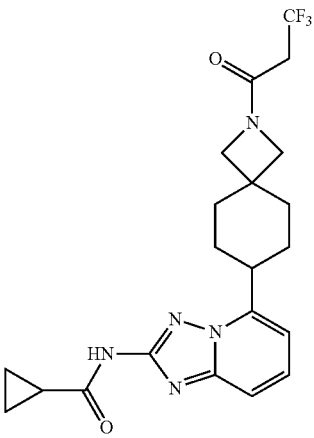

1-10

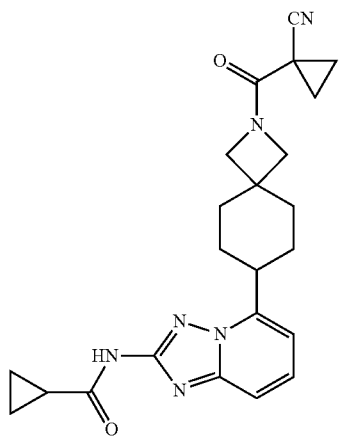

1-11

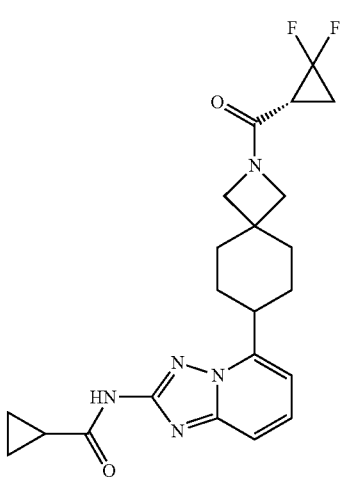

1-12

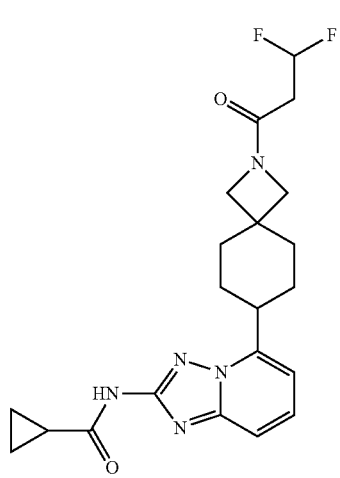

1-14

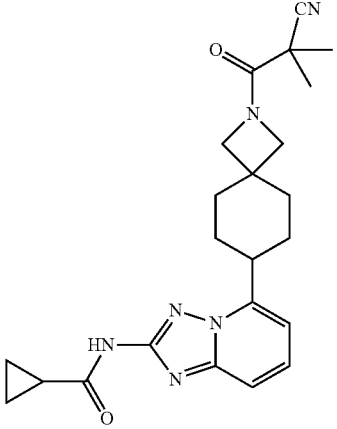

1-15

Compound 1-7: $^1$H NMR (400 MHz, DMSO-d$_6$) δ 11.08 (br s, 1H), 7.48-7.78 (m, 2H), 7.03 (d, J=7.0 Hz, 1H), 3.86-4.25 (m, 2H), 3.61-3.80 (m, 2H), 3.29-3.38 (m, 1H), 2.69-2.88 (m, 1H), 1.85-2.19 (m, 7H), 1.51-1.79 (m, 4H), 0.83-0.96 (m, 4H). LCMS (ESI) m/z: 430.0[M+H]$^+$.

Compound 1-8: $^1$H NMR (400 MHz, DMSO-d$_6$) δ 11.14 (br s, 1H), 7.52-7.66 (m, 2H), 7.00 (d, J=7.03 Hz, 1H), 3.54-3.83 (m, 6H), 3.29 (br t, J=11.54 Hz, 1H), 1.94-2.09 (m, 5H), 1.41-1.70 (m, 4H), 0.77-0.90 (m, 4H). LCMS (ESI) m/z: 393.1[M+H]$^+$.

Compound 1-9: $^1$H NMR (400 MHz, DMSO-d$_6$) δ 10.99 (br s, 1H), 7.49-7.65 (m, 2H), 6.99 (br d, J=7.03 Hz, 1H), 4.02-4.20 (m, 2H), 3.61-3.78 (m, 2H), 1.94-2.13 (m, 5H), 1.48-1.72 (m, 4H), 1.14-1.32 (m, 4H), 0.77-0.87 (m, 4H). LCMS (ESI) m/z: 412.1[M+H]$^+$.

Compound 1-10: $^1$H NMR (400 MHz, METHANOL-d$_4$) δ 7.77-7.87 (m, 1H), 7.62 (d, J=8.78 Hz, 1H), 7.20 (dd, J=7.28, 11.80 Hz, 1H), 4.08 (s, 1H), 3.96 (s, 1H), 3.83 (s, 1H), 3.72 (s, 1H), 3.43-3.56 (m, 1H), 3.22 (dq, J=6.90, 10.75 Hz, 2H), 2.06-2.23 (m, 4H), 1.94 (br s, 1H), 1.56-1.84 (m, 3H), 1.56-2.00 (m, 1H), 0.94-1.14 (m, 4H). LCMS (ESI) m/z: 436.1[M+H]$^+$.

Compound 1-11: $^1$H NMR (400 MHz, METHANOL-d$_4$) δ 7.56-7.67 (m, 1H), 7.50 (d, J=8.78 Hz, 1H), 7.00 (t, J=7.15 Hz, 1H), 4.26-4.48 (m, 2H), 3.70-3.90 (m, 2H), 3.42-3.59 (m, 1H), 2.08-2.24 (m, 4H), 1.48-1.99 (m, 9H), 0.87-1.10 (m, 4H). LCMS (ESI) m/z: 419.1[M+H]$^+$.

Compound 1-12: $^1$H NMR (400 MHz, METHANOL-d$_4$) δ 7.56-7.64 (m, 1H), 7.48 (d, J=9.03 Hz, 1H), 6.97 (d, J=7.28 Hz, 1H), 3.91-4.17 (m, 2H), 3.78-3.86 (m, 1H), 3.67-3.75 (m, 1H), 3.40-3.54 (m, 1H), 2.53-2.69 (m, 1H), 1.92-2.21 (m, 6H), 1.72-1.85 (m, 3H), 1.50-1.69 (m, 2H), 0.86-1.08 (m, 4H). LCMS (ESI) m/z: 430.1[M+H]$^+$.

Compound 1-14: $^1$H NMR (400 MHz, METHANOL-d$_4$) δ 7.57-7.66 (m, 1H), 7.50 (d, J=8.78 Hz, 1H), 6.95-7.03 (m, 1H), 6.01-6.38 (m, 1H), 4.62 (s, 1H), 3.65-4.10 (m, 4H), 3.43-3.58 (m, 1H), 2.76-2.93 (m, 2H), 2.04-2.21 (m, 4H), 1.51-1.87 (m, 4H), 1.01-1.07 (m, 2H), 0.93 (qd, J=3.74, 7.34 Hz, 2H). LCMS (ESI) m/z: 418.1[M+H]$^+$.

Compound 1-15: $^1$H NMR (400 MHz, DMSO-d$_6$) δ 11.01 (br s, 1H), 7.48-7.66 (m, 2H), 7.00 (dd, J=7.53, 9.79 Hz, 1H), 4.11-4.33 (m, 2H), 3.60-3.81 (m, 2H), 3.25-3.32 (m, 1H), 2.03 (br t, J=9.03 Hz, 5H), 1.53-1.73 (m, 4H), 1.49 (d, J=4.77 Hz, 6H), 0.76-0.88 (m, 4H). LCMS (ESI) m/z: 421.1[M+H]$^+$.

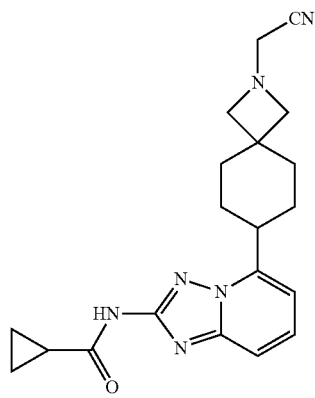

1-16

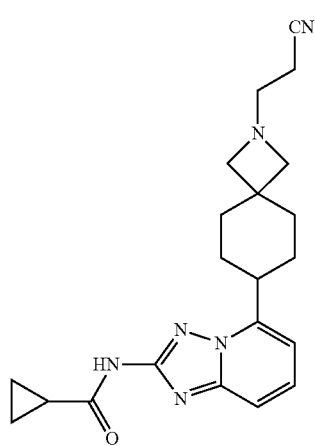

1-17

Synthesis of compound 1-16: Compound 1-6 (100 mg, 227.6 μmol, TFA) was dissolved into N,N-dimethyl formamide (5 mL), added with potassium carbonate (94 mg, 682.7 μmol) and 2-bromoacetonitrile (30 mg, 250.3 μmol), and stirred for 12 hours at 10° C. LC-MS showed reaction was complete. Reaction solution was diluted with water (5 mL), extracted by dichloromethane/methanol (10/1, 10 mL), washed by saturated saline solution (10 mL), dried by sodium sulfate anhydrous, filtered and concentrated under reduced pressure. Residues were processed by preparative HPLC (neutral system) to provide compound 1-16. $^1$H NMR (400 MHz, METHANOL-d$_4$) δ 7.83 (t, J=8.03 Hz, 1H), 7.64 (br d, J=8.78 Hz, 1H), 7.21 (d, J=7.53 Hz, 1H), 4.51 (s, 2H), 4.23 (s, 2H), 4.08 (s, 2H), 3.49 (br t, J=11.92 Hz, 1H), 2.14-2.30 (m, 4H), 1.79-1.97 (m, 3H), 1.59-1.74 (m, 2H), 0.95-1.12 (m, 4H). LCMS (ESI) m/z: 365.0[M+H]$^+$.

The following compounds having the following characteristic data were obtained from compound 1-6 as common intermediate by using the same synthesis and separation methods as those used for compound 1-16 (bromoacetonitrile was correspondingly replaced by bromopropionitrile in the target molecules):

Compound 1-17: $^1$H NMR (400 MHz, DMSO-d$_6$) δ11.00 (br s, 1H), 7.50-7.63 (m, 2H), 6.96 (d, J=6.27 Hz, 1H), 3.33-3.34 (m, 2H), 3.23-3.30 (m, 1H), 2.95 (s, 2H), 3.05 (s, 2H), 2.58-2.69 (m, 2H), 1.99 (br d, J=10.29 Hz, 5H), 1.40-1.65 (m, 4H), 0.74-0.88 (m, 4H). LCMS (ESI) m/z: 379.0[M+H]$^+$.

Example 2

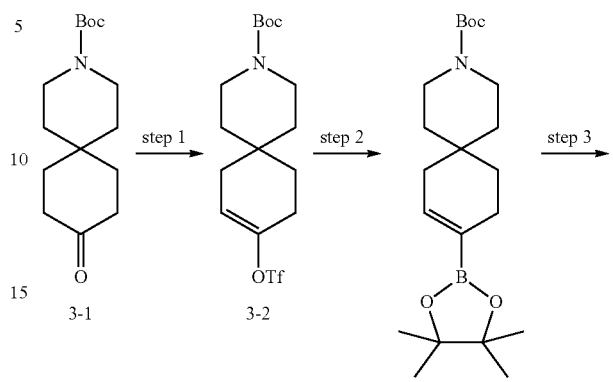

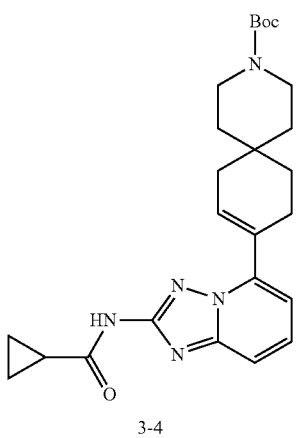

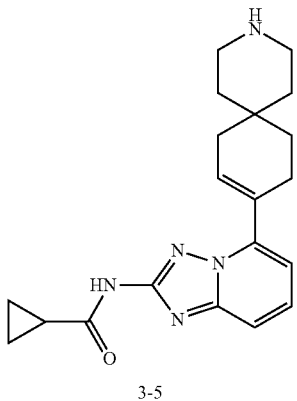

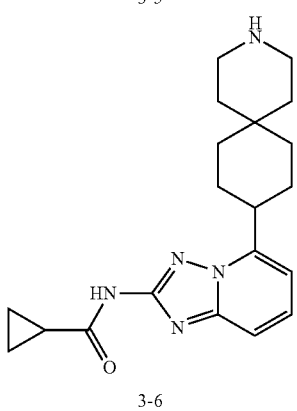

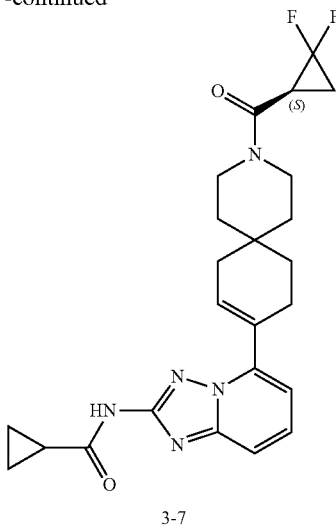

3-7

Step 1: In nitrogen atmosphere at −78° C., tert-butyl 9-oxygen-3-azaspiro[5.5]hendecane-3-carboxylic acid (3-1) (5 g, 18.7 mmol) was dissolved into anhydrous tetrahydrofuran (150 mL), slowly dripped with bis(trimethylsilyl) amine lithium (1 M, 22.4 mL), and stirred for 1 hour at −78° C. Then, the reaction solution was added with anhydrous tetrahydrofuran (50 mL) solution containing 1,1,1-trifluoro-N-[-(trifluoromethyl)sulfonyl]-methane sulfonamide (7.35 g, 20.6 mmol), and stirred for 12 hours at 15° C. TLC showed reaction was complete. The reaction solution was quenched by saturated ammonium chloride (50 mL), and extracted by EtOAc (200 mL*2). The combined organic phase was washed by saturated saline solution (50 mL), dried by anhydrous sodium sulfate, filtered and concentrated at reduced pressure to provide compound 3-2, which was directly used in following reactions without being purified.

Step 2: Compound 3-2 (8 g, 20.0 mmol) and Bis(pinacolato)diboron (5.59 g, 22.0 mmol) were dissolved into N,N-dimethylformamide (100 mL), added with potassium acetate (5.90 g, 60.1 mmol) and 1,1'-Bis(diphenylphosphino)ferrocene-palladium(II)dichloride dichloromethane (1.64 g, 2.0 mmol), and stirred for 3 hours at 70° C. TLC showed reaction was complete. The reaction solution was diluted with water (300 mL), and extracted by EtOAc (200 mL*2). Combined organic phases were washed by saturated saline solution (150 mL), dried by anhydrous sodium sulfate, filtered and concentrated at reduced pressure. Residues were separated by rapid silicon gel column (0~10% EtOAc/PE) to provide compound 3-3. $^1$H NMR (400 MHz, CDCl$_3$) δ6.41 (br s, 1H), 6.34-6.47 (m, 1H), 3.32-3.44 (m, 2H), 3.14-3.29 (m, 2H), 2.00-2.10 (m, 2H), 1.90 (br d, J=3.01 Hz, 2H), 1.38 (s, 9H), 1.28 (br t, J=5.52 Hz, 4H), 1.19 (s, 12H).

Step 3: In nitrogen atmosphere, mixed dioxane (40 ml) and water (10 ml) solution containing N-(5-bromo-[1,2,4]triazole[1,5-a] pyridine-2-yl) cyclopropyl formamide (2 g, 7.1 mmol), compound 3-3 (3.49 g, 9.3 mmol), potassium carbonate (2.95 g, 21.3 mmol), and [1,1-Bis (diphenylphosphine) ferrocene]palladium dichloride dichloromethane (581 mg, 711.5 μmol) was replaced by nitrogen for 3 times, and the reaction solution was heated to 90° C. for 3 hours. LC-MS showed that the reaction was complete. The reaction solution was concentrated under reduced pressure, and the residue was separated by a rapid silica gel column (0~4% methanol/dichloromethane) to provide compounds 3-4. LCMS (ESI) m/z: 452.4[M+H]$^+$.

Step 4: Compound 3-4 (3.5 g, 7.8 mmol) was dissolved into dichloromethane (15 mL), added with hydrochloric acid/EtOAc (4 M, 30 mL), and left to react for 30 minutes at 20° C. LC-MS showed reaction was complete. Solid was precipitated, filtered and dried to provide compound 3-5. LCMS (ESI) m/z: 352.2[M+H]$^+$.

Step 5: In N$_2$ atmosphere, compound 3-5 (2.9 g, 7.4 mmol, hydrochloride) was dissolved into methanol (100 mL), added with catalyst dry palladium/carbon) 1 g, 10%), and replaced by hydrogen for 3 times. The reaction solution was stirred for 12 hours at hydrogen pressure (30 Psi) and reaction temperature of 25° C. LC-MS showed reaction was complete. Solid was filtered by diatomite to provide filtrate, which was then concentrated to provide compound 3-6 ((2.6 g hydrochloride). LCMS (ESI) m/z: 354.7[M+H]$^+$.

Step 6: Compound 3-6 (1 g, 2.6 mmol, hydrochloride) was dissolved into N,N-dimethylformamide (20 mL), added with HOBt (573 mg, 4.2 mmol) and EDCI (813 mg, 4.2 mmol) and then (1S)-2,2-difluorocyclopropyl carboxylic acid (380 mg, 3.1 mmol) and DIEA (731 mg, 5.7 mmol), and left to react for 12 hours at 15° C. LC-MS showed reaction was complete. The reaction solution was diluted with water (100 mL), and extracted by dichloromethane/methanol (10/1, 150 mL*2). Combined organic phases were washed with saturated saline solution (100 mL), dried by anhydrous sodium sulfate, filtered and concentrated at reduced pressure. The residue was processed by preparative HPLC (neutral system) to provide compound 3-7. $^1$H NMR (400 MHz, METHANOL-d$_4$) δ 7.57-7.64 (m, 1H), 7.48 (d, J=8.78 Hz, 1H), 7.02 (d, J=7.28 Hz, 1H), 3.63-3.77 (m, 3H), 3.41-3.61 (m, 2H), 2.93 (dt, J=8.28, 11.80 Hz, 1H), 1.36-2.06 (m, 15H), 1.04 (quin, J=3.76 Hz, 2H), 0.93 (qd, J=3.66, 7.34 Hz, 2H). LCMS (ESI) m/z: 458.1[M+H]$^+$.

The following compounds having the following characteristic data were obtained from compound 3-6 as common intermediate by using the same synthesis and separation methods as those used for compound 3-7 (carboxylic acids for compound 3-7 were replaced by carboxylic acids in the following target molecules at acid amide condensation reactions):

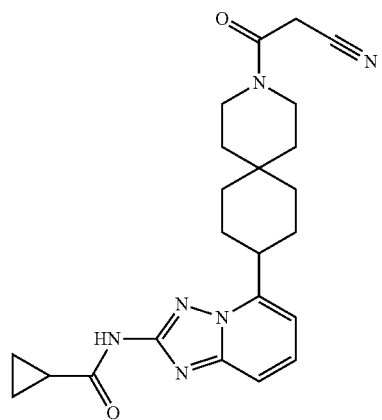

3-8

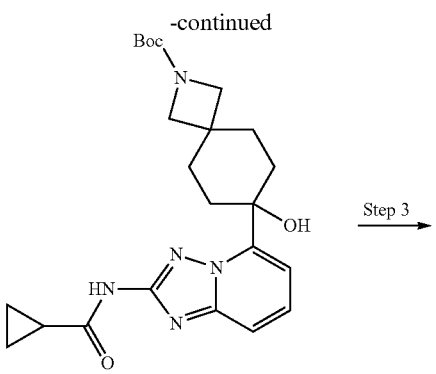

3-9

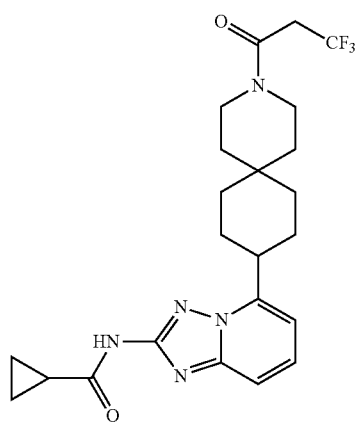

Compound 3-8: $^1$H NMR (400 MHz, METHANOL-$d_4$) δ 7.57-7.67 (m, 1H), 7.49 (d, J=8.53 Hz, 1H), 7.03 (dd, J=3.76, 6.78 Hz, 1H), 4.61 (s, 1H), 3.83-3.91 (m, 1H), 3.62 (td, J=3.76, 7.53 Hz, 2H), 3.42-3.54 (m, 3H), 1.68-2.08 (m, 9H), 1.40-1.56 (m, 4H), 1.05 (quin, J=3.76 Hz, 2H), 0.88-0.97 (m, 2H). LCMS (ESI) m/z: 421.1 [M+H]$^+$.

Compound 3-9: $^1$H NMR (400 MHz, METHANOL-$d_4$) δ 7.61 (dd, J=7.28, 8.78 Hz, 1H), 7.49 (d, J=8.78 Hz, 1H), 7.02 (dd, J=4.52, 6.78 Hz, 1H), 3.63 (td, J=3.83, 7.40 Hz, 2H), 3.43-3.58 (m, 5H), 1.67-2.07 (m, 9H), 1.39-1.54 (m, 4H), 1.01-1.08 (m, 2H), 0.93 (qd, J=3.68, 7.28 Hz, 2H). LCMS (ESI) m/z: 464.1[M+H]$^+$.

Example 3

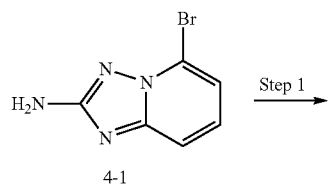

4-1

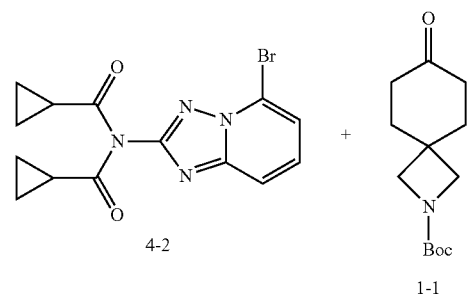

4-2

1-1

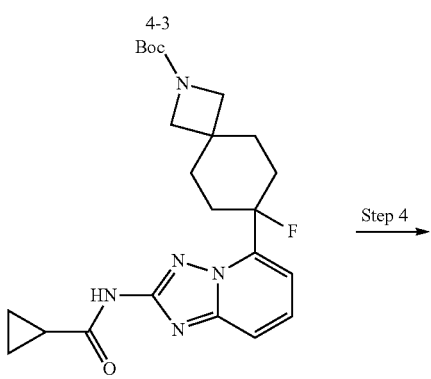

4-3

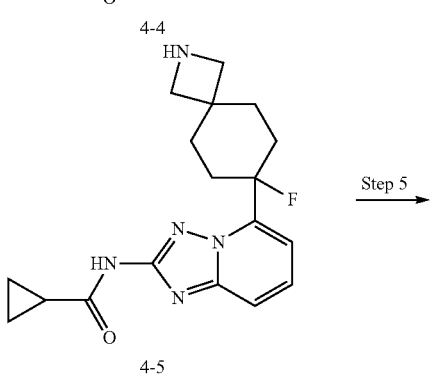

4-4

4-5

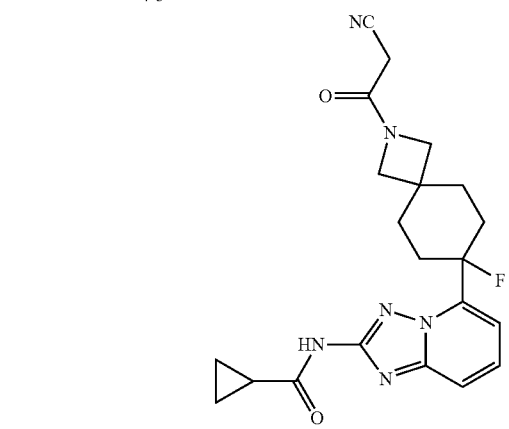

4-6

Step 1: At 0° C., 5-bromo-[1,2,4]triazolo[1,5-a]pyridyl-2-amine (4-1) (5 g, 23.5 mmol) was dissolved into acetonitrile (50 mL), added with triethylamine (11.87 g, 117.4 mmol) and cyclopropanecarbonyl chloride (6.13 g, 58.7 mmol), and left to react for 12 hours at 25° C. TLC showed reaction was complete. Solvent acetonitrile was removed by concentration under reduced pressure, and residues were separated by rapid column (0-5% methanol/dichloromethene) to provide compound 4-2. LCMS (ESI) m/z: 350.8[M+H]⁺.

Step 2: In N₂ atmosphere, compound 4-2 (1.99 g, 5.7 mmol) and compound 1-1 (1.5 g, 6.3 mmol) were dissolved into anhydrous tetrahydrofuran (30 mL), slowly added with n-butyllithium (2.5 M, 5.7 mL) solution at −70° C., and stirred for 30 minutes at 10°. LC-MS showed reaction was complete. The reaction solution was quenched by saturated ammonium chloride (50 mL) at 0° C., and extracted by EtOAc (150 mL*2). Combined organic phases were washed by saturated saline solution (10 mL), dried by anhydrous sodium sulfate, filtered and concentrated under reduced pressure. Residues were separated by rapid silicon gel column (0-3% methanol/dichloromethane) to provide compound 4-3. LCMS (ESI) m/z: 442.3[M+H]⁺.

Step 3: At 0° C., compound 4-3 (0.8 g, 1.81 mmol) was dissolved into anhydrous dichloromethane (10 mL), added with diethylaminosulphur trifluoride (DAST) (351 mg, 2.17 mmol), left to react for 15 minutes at 0° C., and then left to react for 1 hour after heating to 25° C. LC-MS showed reaction was complete. Reaction solution was quenched by saturated aqueous sodium bicarbonate solution (5 mL) at 0° C., diluted by water (10 mL), and extracted by dichloromethane (50 mL*3). The combined organic phases were by saturated saline solution (20 mL), dried by anhydrous sodium sulfate, filtered and concentrated under reduced pressure. Residues were separated by rapid silicon gel column (0-100% EtOAc/PE) to provide compound 4-4. LCMS (ESI) m/z: 444.3[M+H]⁺.

Step 4: Compound 4-4 (410 mg, 924.4 μmol) was dissolved into dichloromethane (5 mL), added with hydrochloric acid/EtOAc (4 M, 10 mL), and left to react for 30 minutes at 20° C. LC-MS showed reaction was complete. Solid was precipitated, filtered and dried to provide compound 4-5 (390 mg hydrochloride). LCMS (ESI) m/z: 344.2[M+H]⁺.

Step 5: Compound 4-5 (130 mg, 342.2 μmol, hydrochloride) was dissolved into N,N-dimethylformamide (10 mL), added with HOBt (77 mg, 567.9 μmol) and EDCI (109 mg, 567.9 μmol), then added with 2-cyanoacetic acid (35 mg, 416.4 μmol) and diisopropylethylamine (98 mg, 757.1 μmol), and left to react for 12 hours at 15° C. LC-MS showed reaction was complete. Reaction solution was concentrated under reduced pressure, and residues were processed by preparative HPLC (neutral system) to provide compound 4-6. ¹H NMR (400 MHz, METHANOL-d₄) δ 7.66-7.72 (m, 1H), 7.56-7.62 (m, 1H), 7.25 (t, J=7.28 Hz, 1H), 4.29 (s, 1H), 4.03 (s, 1H), 3.97 (s, 1H), 3.76 (s, 1H), 3.26-3.30 (m, 2H), 2.97-3.28 (m, 2H), 1.74-2.08 (m, 7H), 0.89-1.13 (m, 4H). LCMS (ESI) m/z: 411.1 [M+H]⁺.

The following compounds 4-7 and 4-8 having the following characteristic data were obtained from compound 4-5 as common intermediate by using the same synthesis and separation methods as those used for compound 4-6 (carboxylic acids compounds with different substituents from compound 4-6 were added)

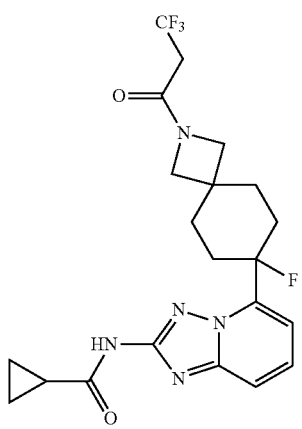

4-7

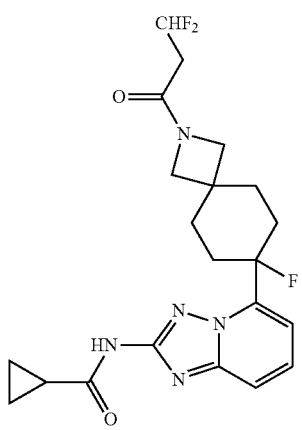

4-8

Compound 4-7: ¹H NR (400 MHz, METHANOL-d₄) δ=7.65-7.73 (m, 1H), 7.59 (dt, J=1.13, 9.72 Hz, 1H), 7.20-7.29 (m, 1H), 4.33 (s, 1H), 4.01 (d, J=11.29 Hz, 2H), 3.76 (s, 1H), 2.99-3.30 (m, 4H), 1.74-2.10 (m, 7H), 0.88-1.12 (m, 4H). LCMS (ESI) m/z: 454.1[M+H]⁺.

Compound 4-8: ¹H NMR (400 MHz, METHANOL-d₄) δ=7.64-7.73 (m, 1H), 7.59 (dt, J=1.25, 9.16 Hz, 1H), 7.20-7.28 (m, 1H), 6.01-6.44 (m, 1H), 4.30 (s, 1H), 3.99 (d, J=11.80 Hz, 2H), 3.73 (s, 1H), 2.99-3.27 (m, 2H), 2.76-2.99 (m, 2H), 1.75-2.10 (m, 7H), 0.89-1.10 (m, 4H). LCMS (ESI) m/z: 436.1[M+H]⁺.

Example 4

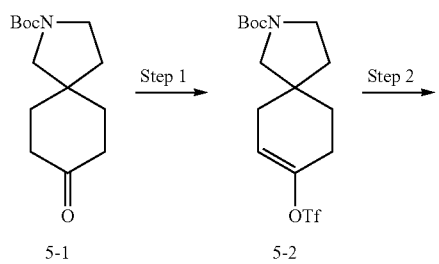

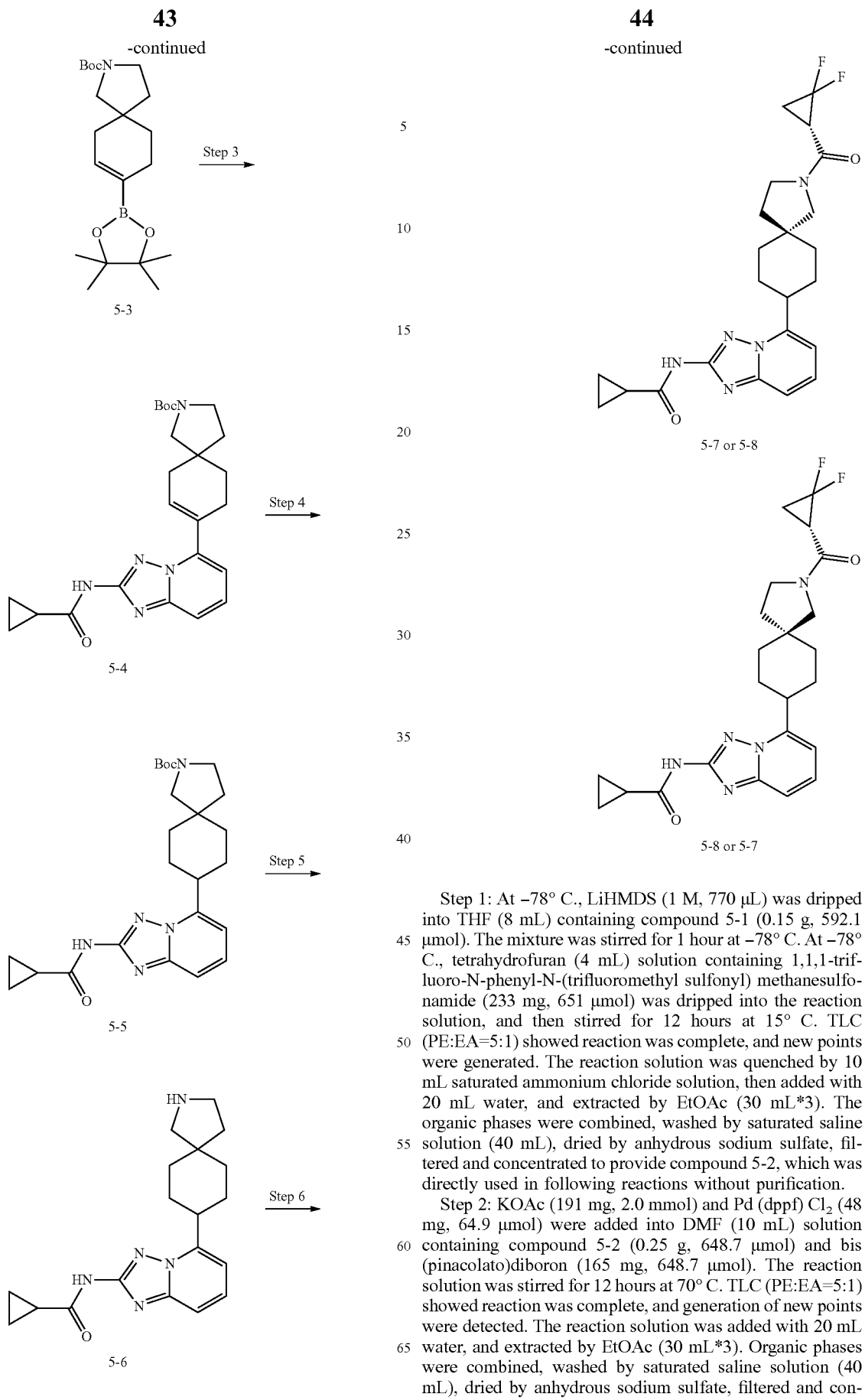

Step 1: At −78° C., LiHMDS (1 M, 770 μL) was dripped into THF (8 mL) containing compound 5-1 (0.15 g, 592.1 μmol). The mixture was stirred for 1 hour at −78° C. At −78° C., tetrahydrofuran (4 mL) solution containing 1,1,1-trifluoro-N-phenyl-N-(trifluoromethyl sulfonyl) methanesulfonamide (233 mg, 651 μmol) was dripped into the reaction solution, and then stirred for 12 hours at 15° C. TLC (PE:EA=5:1) showed reaction was complete, and new points were generated. The reaction solution was quenched by 10 mL saturated ammonium chloride solution, then added with 20 mL water, and extracted by EtOAc (30 mL*3). The organic phases were combined, washed by saturated saline solution (40 mL), dried by anhydrous sodium sulfate, filtered and concentrated to provide compound 5-2, which was directly used in following reactions without purification.

Step 2: KOAc (191 mg, 2.0 mmol) and Pd (dppf) Cl$_2$ (48 mg, 64.9 μmol) were added into DMF (10 mL) solution containing compound 5-2 (0.25 g, 648.7 μmol) and bis(pinacolato)diboron (165 mg, 648.7 μmol). The reaction solution was stirred for 12 hours at 70° C. TLC (PE:EA=5:1) showed reaction was complete, and generation of new points were detected. The reaction solution was added with 20 mL water, and extracted by EtOAc (30 mL*3). Organic phases were combined, washed by saturated saline solution (40 mL), dried by anhydrous sodium sulfate, filtered and concentrated to provide a coarse product, which was separated and purified by chromatography (SiO$_2$, PE:EA=50:0~20:1) to provide colorless oily compound 5-3. $^1$H NMR (400 MHz, METHANOL-d4) δ6.50 (br s, 1H), 3.35-3.49 (m, 2H), 3.07-3.15 (m, 2H), 2.02-2.22 (m, 4H), 1.54-1.81 (m, 4H), 1.47 (s, 9H), 1.27 (s, 12H).

Step 3: The solution of dioxane (4 mL) and water (1 mL) containing compound 5-3 (0.13 g, 357.8 μmol), N-(5-bromo-[1,2,4]triazolo[1,5-a]pyridine-2-yl)cyclopropane formamide (101 mg, 357.8 μmol), K$_2$CO$_3$ (149 mg, 1.1 mmol), and Pd(dppf)Cl$_2$ (26 mg, 35.8 μmol) was replaced by nitrogen gas. The mixture was stirred in nitrogen atmosphere for 12 hours at 90° C. LCMS showed reaction was complete, and target molecular ion peaks were detected. The reaction solution was removed of the solvent by concentrating, then dispersed in 10 mL water, and extracted by DCM/MeOH (10:1, 30 mL*3). Organic phases were combined, washed by the saturated saline solution (40 mL) and dried by anhydrous sodium sulfate, then filtered to provide filtrate, which was distillated under reduced pressure to provide a coarse product. The coarse product was purified by the chromatographic column method (SiO$_2$, DCM:MeOH=1:0 to 20:1) to provide compound 5-4. LCMS (ESI) m/z: 438.3[M+H]$^+$.

Step 4: In argon atmosphere, Pd/C (10%, 50 mg) was added into methanol (10 mL) containing compound 5-4 (0.2 g, 457.1 μmol). The mixture was replaced by hydrogen for 3 time, and then stirred in hydrogen atmosphere (15 psi) for 2 hours at 25° C. LCMS showed raw materials were consumed completely, and target molecular ion peaks were detected. The reaction solution was filtered and concentrated to provide compound 5-5, which was directly used in following reactions without purification. LCMS (ESI) m/z: 440.4[M+H]$^+$.

Step 5: Dichloromethane (10 mL) containing compound 5-5 (150 mg, 341.3 μmol) and TFA (4 mL) was replaced by nitrogen for 3 times, and the reaction solution was stirred for 30 minutes at 25° C. LCMS showed raw materials were consumed completely, and target molecular ion peaks were detected. The reaction solution was concentrated and removed of solvent to provide compound 5-6 (0.15 g, TFA salt), which was directly used in following reactions without purification. LCMS (ESI) m/z: 340.2[M+H]$^+$.

Step 6: EDCI (104 mg, 541.1 μmol), HOBt (73 mg, 541.1 μmol), and DIEA (140 mg, 1.1 mmol, 189 μL) were added into DMF (4 mL) containing (1S)-2,2-difluorocyclopropyl formic acid (44 mg, 360.7 μmol), stirred to react for 5 minutes at 25° C., then added with compound 5-6 (122 mg, 270 μmol, TFA salt), and stirred for 16 hours at 25° C. LCMS showed raw materials were consumed completely, and target molecular ion peaks were detected. Coarse product was separated (neutral separation condition, chromatographic column: Waters Xbridge 150 mm*25 mm 5 μm; mobile phase: [H$_2$O (10 mM NH$_4$HCO$_3$)-ACN]; B (CH$_3$CN) %: 25%-55%, 7 min) and SFC chiral separation (chromatographic column: DAICEL CHIRALCEL OD-H (250 mm*30 mm, 5 μm); mobile phase: [0.1% NH$_3$H$_2$O EtOH]; B (CO$_2$) %: 40%) to provide compound 5-7, SFC retention time: 3.685 min. $^1$H NMR (400 MHz, METHANOL-d$_4$) δ 7.48-7.55 (m, 1H), 7.39 (d, J=8.78 Hz, 1H), 6.92 (dd, J=6.90, 3.39 Hz, 1H), 3.35-3.76 (m, 5H), 2.66-2.94 (m, 1H), 1.51-2.10 (m, 13H), 0.94 (br s, 2H), 0.78-0.88 (m, 2H). LCMS (ESI) m/z: 444.1[M+H]$^+$. Compound 5-8, SFC retention time: 4.283 min. $^1$H NMR (400 MHz, METHANOL-d$_4$) δ 7.48-7.59 (m, 1H), 7.40 (br d, J=8.53 Hz, 1H), 6.94 (br d, J=6.78 Hz, 1H), 3.23-3.78 (m, 5H), 2.65-2.81 (m, 1H), 1.54-2.06 (m, 13H), 0.95 (br s, 2H), 0.77-0.87 (m, 2H). LCMS (ESI) m/z: 444.2[M+H]$^+$.

The following compounds having the following characteristic data were obtained from compound 5-6 as common intermediate by using the same synthesis and separation methods as those used for compound 5-7 (carboxylic acids compounds with different substituents from compound 5-7 were added):

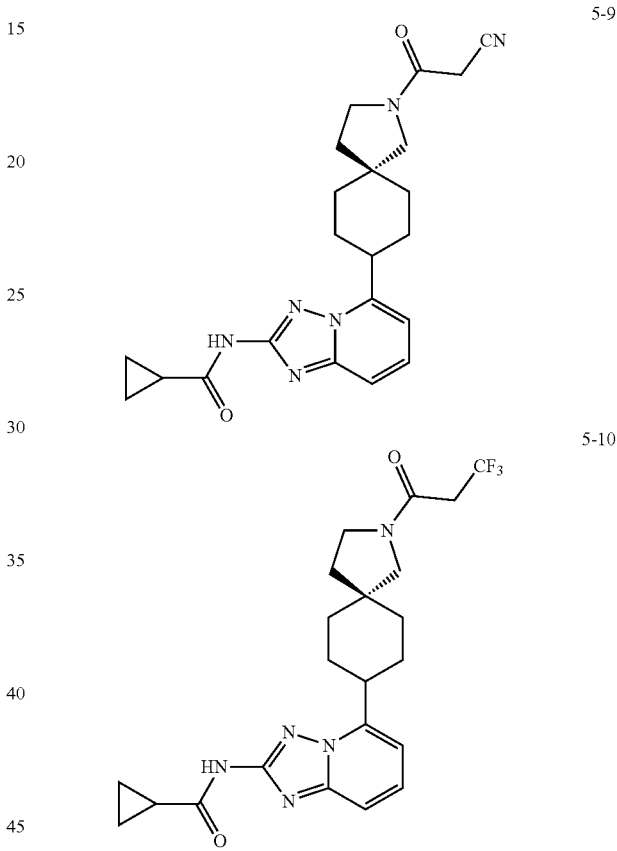

5-9

5-10

Compound 5-9: Use HPLC (neutral separation condition, chromatographic column: Waters Xbridge 150 mm*25 mm 5 μm; mobile phase: [H$_2$O (10 mM NH$_4$HCO$_3$)-ACN]; B (CH$_3$CN) %: 18%-32%, 9 min) for separation, retention time of 2.117 min. $^1$H NMR (400 MHz, METHANOL-d$_4$) δ 7.60-7.68 (m, 1H), 7.52 (d, J=8.6 Hz, 1H), 7.05 (dd, J=3.4, 6.8 Hz, 1H), 3.44-3.73 (m, 4H), 3.31 (br s, 2H), 2.11 (td, J=7.6, 14.9 Hz, 3H), 2.01 (br t, J=7.3 Hz, 1H), 1.96 (br s, 1H), 1.66-1.88 (m, 6H), 1.31 (br s, 1H), 1.02-1.10 (m, 2H), 0.91-0.99 (m, 2H). LCMS (ESI) m/z: 407.2[M+H]$^+$.

Compounds 5-10: SFC chiral resolution condition, chromatographic column: DAICEL CHIRALCEL OD-H (250 mm*30 mm, 5 μm); mobile phase: [0.1% NH$_3$H$_2$O EtOH]; B (CO$_2$) %: 40%-40%, retention time of 4.114 min. $^1$H NMR (400 MHz, METHANOL-d$_4$) δ=7.52 (br d, J=8.0 Hz, 1H), 7.40 (br d, J=8.8 Hz, 1H), 6.89-6.98 (m, 1H), 3.57 (t, J=7.0 Hz, 1H), 3.25-3.51 (m, 6H), 1.78-2.09 (m, 5H), 1.51-1.76 (m, 6H), 0.94 (br d, J=3.8 Hz, 2H), 0.79-0.88 (m, 2H). LCMS (ESI) m/z: 450.2[M+H]$^+$.

Example 5

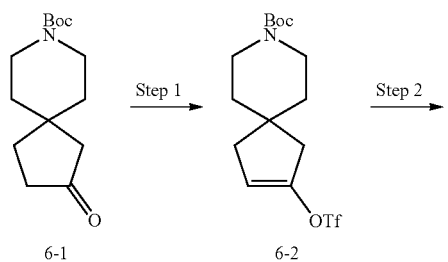

6-1 → 6-2

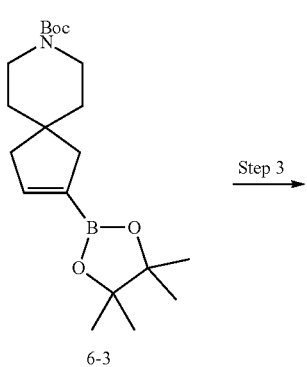

6-3

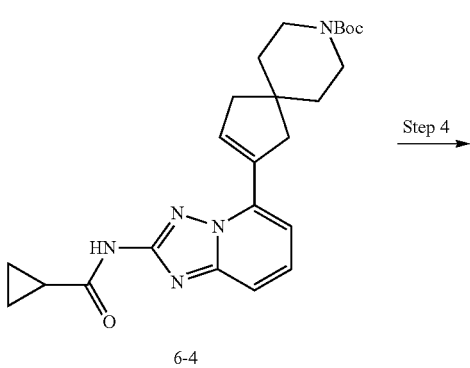

6-4

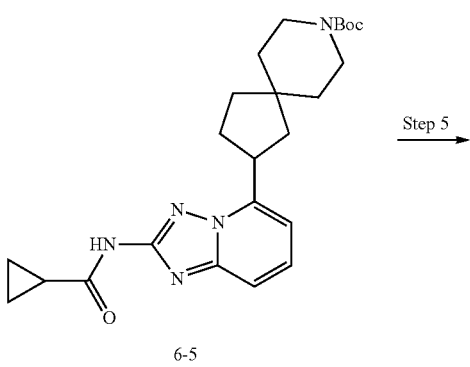

6-5

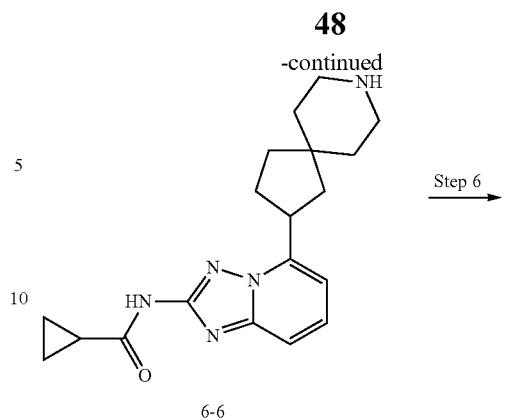

6-6

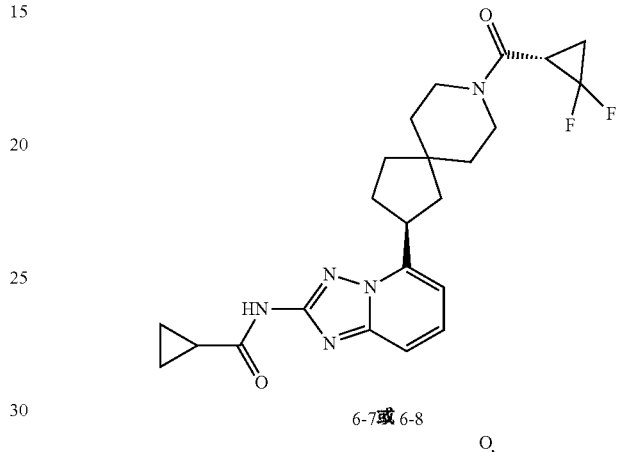

6-7或 6-8

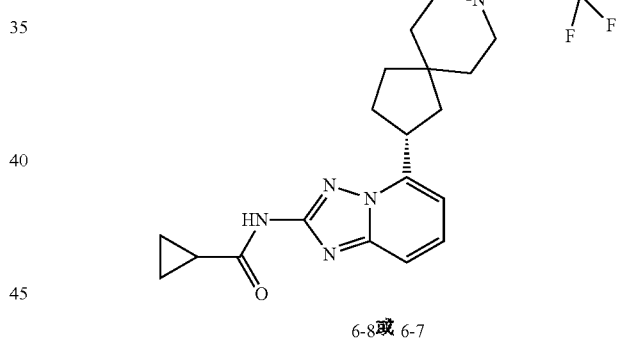

6-8或 6-7

Step 1: At −78° C., LiHMDS (1 M, 1.3 mL) was dripped into THF (8 mL) containing compound 6-1 (250 mg, 986.8 μmol). The mixture was stirred for 1 hour at −78° C. At −78° C., tetrahydrofuran (4 mL) containing 1,1,1-trifluoro-N-phenyl-N-(trifluoromethyl sulfonyl) methane sulfonamide (388 mg, 1.1 mmol) was dripped to the reaction solution, and then stirred for 12 hours at 25° C. TLC (PE:EA=5:1) showed raw materials were completely reacted, and new points were generated. The reaction solution was quenched by using 10 mL saturated ammonium chloride solution, then added with 20 mL water, and extracted by EtOAc (30 mL*3). Organic phases were combined, washed by saturated saline solution (40 mL), dried by anhydrous sodium sulfate, filtered and concentrated to provide coarse product, then separated and purified by chromatographic column (SiO$_2$, PE:EA=20:1~10:1) to provide compound 6-2.

Step 2: KOAc (295 mg, 3.0 mmol) and Pd(dppf)Cl$_2$·CH$_2$Cl$_2$ (82 mg, 100 μmol) were added into DMF (5 mL) solution containing compound 6-2 (386 mg, 1.0 mmol) and bis(pinacolato)diboron (254 mg, 1.0 mmol). The reaction solution was stirred for 12 hours at 70° C. TLC (PE:EA=5:1) showed raw materials were consumed completely, and generation of new points were detected. The reaction solution was added with 20 mL water, and extracted by EtOAc (30 mL*3). Organic phases were combined, washed by saline solution (40 mL), dried by anhydrous sodium sulfate, filtered and concentrated to provide coarse product, which was separated and purified by chromatographic column (SiO$_2$, PE:EA=50:0~20:1) to provide compound 6-3.

Step 3: Dioxane (4 mL) and water (1 mL) solution containing compound 6-3 (186 mg, 512 μmol), N-(5-bromo-[1,2,4]triazolo[1,5-a]pyridine-2-yl)cyclopropane formamide (144 mg, 512 μmol), K$_2$CO$_3$ (212 mg, 1.5 mmol), Pd(dppf)Cl$_2$·CH$_2$Cl$_2$ (42 mg, 51.2 μmol) was replaced by nitrogen for 3 times. In nitrogen condition, the mixture was stirred for 12 hours at 90° C. LCMS showed raw materials were consumed completely, and target molecular ion peaks were detected. The reaction solution was removed of solvent, dispersed in 10 mL water, and extracted by DCM:MeOH (10:1, 30 mL*3). Organic phases were combined, washed by saturated saline solution (40 mL), dried by anhydrous sodium sulfate, filtered, and then distillated under reduced pressure to provide a coarse product. The coarse product was purified by chromatographic column method (SiO$_2$, DCM:MeOH=1:0~20:1) to provide compound 6-4. LCMS (ESI) m/z: 438.7 [M+H]$^+$.

Step 4: In argon atmosphere, Pd/C (10%, 50 mg) was into methanol solution (10 mL) containing compound 6-4 (196 mg, 448 μmol). The mixture was replaced by hydrogen for 3 times, and then stirred for 16 hours in hydrogen atmosphere (15 psi) at 25° C. LCMS showed raw materials were consumed completely, and target molecular ion peaks were detected. The reaction solution was filtered, then concentrated to provide compound 6-5, which was directly used in following reactions without purification. LCMS (ESI) m/z: 440.3[M+H]$^+$.

Step 5: Dichloromethane (10 mL) solution containing compound 6-5 (130 mg, 296 μmol) and TFA (4 mL) was replaced by nitrogen for 3 times, and then stirred for 30 minutes at 25° C. LCMS showed raw materials were consumed completely, and target molecular ion peaks were detected. The reaction solution was concentrated to remove the solvent, to provide compound 6-6 (134 mg, TFA salt), which was directly used in following reactions without purification.

Step 6: EDCI (85 mg, 443.3 μmol), HOBt (60 mg, 443.3 μmol), and DIEA (115 mg, 886.5 μmol, 154.4 μL) were added into DMF (4 mL) containing (1S)-2,2-bifluorocyclopropanecarboxylic acid (36 mg, 295.5 μmol), stirred to react for 5 minutes at 25° C., then added with compound 6-6 (134 mg, 295.5 μmol, TFA salt), and stirred for 16 hours at 25° C. LCMS showed that raw materials were consumed completely, and target molecular ion peaks were detected. Coarse product was separated (neutral condition, chromatographic column: Waters Xbridge 150*25 5 μm; mobile phase: [water (10 mM NH$_4$HCO$_3$)-ACN]; B %: 30%-50%, 7 min) and SFC chiral separation (chromatographic column: YMC CHIRAL Amylose-C (250 mm*30 mm, 10 μm; mobile phase: [0.1% NH$_3$H$_2$O EtOH]; B %: 50%). Compound 6-7 was obtained with a SFC retention time of 2.339 min. $^1$H NMR (400 MHz, DMSO-d$_6$) δ 11.01 (br s, 1H), 7.51-7.63 (m, 2H), 7.08 (br d, J=6.78 Hz, 1H), 3.83 (br s, 1H), 3.41-3.66 (m, 4H), 3.15 (br d, J=5.02 Hz, 1H), 2.14-2.35 (m, 2H), 2.06 (br s, 1H), 1.75-1.95 (m, 4H), 1.40-1.73 (m, 6H), 0.84 (br s, 4H). LCMS (ESI) m/z: 444.1[M+H]$^+$. Compound 6-8: SFC retention time is, 4.142 min. $^1$H NMR (400 MHz, DMSO-d$_6$) δ 11.01 (br s, 1H), 7.54-7.65 (m, 2H), 7.08 (br s, 1H), 3.80-3.90 (m, 1H), 3.45-3.66 (m, 4H), 3.09-3.22 (m, 1H), 2.18-2.36 (m, 2H), 2.06 (br s, 1H), 1.75-1.95 (m, 4H), 1.68 (br d, J=7.28 Hz, 3H), 1.50 (br d, J=4.77 Hz, 3H), 0.77-0.88 (m, 4H). LCMS (ESI) m/z: 444.1 [M+H]$^+$.

Example 6

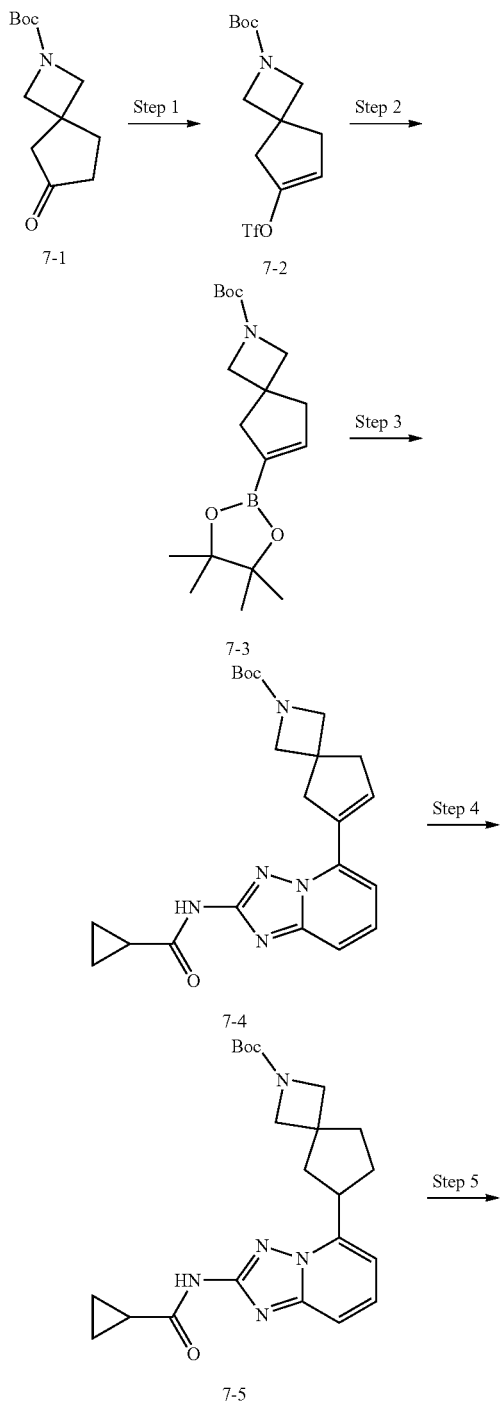

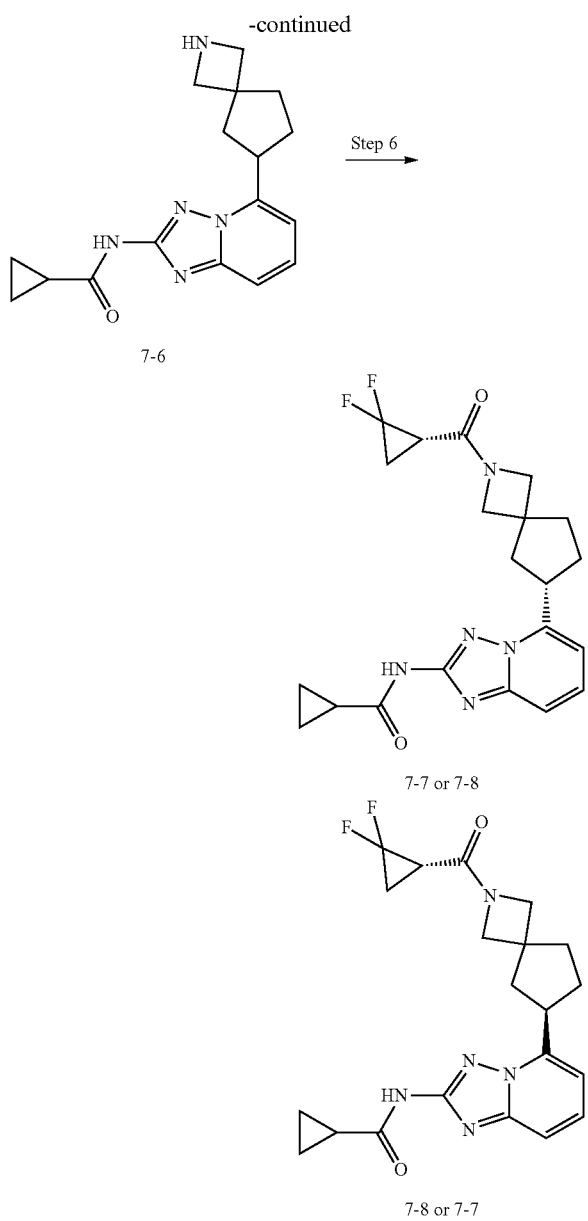

mL) solution containing compound 7-2 (0.46 g, 1.3 mmol) and bis(pinacolato)diboron (327 mg, 1.3 mmol). The reaction solution was stirred for 12 hours at 70° C. TLC (PE:EA=5:1) showed raw materials were reacted completely, and generation of new points were detected. The reaction solution was quenched by adding 20 mL water, and extracted by EtOAc (30 mL*3). Organic phases were combined, washed by saturated saline solution (40 mL), dried by anhydrous sodium sulfate, filtered and concentrated to provide a coarse product, which was purified by chromatographic method (SiO$_2$, PE:EA=50:0~20:1) to provide compound 7-3. $^1$H NMR (400 MHz, CDCl$_3$) δ 6.45 (t, J=1.88 Hz, 1H), 3.83-3.88 (m, 2H), 3.73-3.78 (m, 2H), 2.36-2.42 (m, 2H), 2.04 (t, J=7.03 Hz, 2H), 1.37 (s, 9H), 1.21 (s, 12H).

Step 3: Dioxane (4 mL) and water (1 mL) solution containing compound 7-3 (0.15 g, 447.43 μmol), N-(5-bromo-[1,2,4]triazolo[1,5-a]pyridine-2-yl)cyclopropane formamide (126 mg, 447.43 μmol), K$_2$CO$_3$ (186 mg, 1.34 mmol), and Pd(dppf)Cl$_2$·CH$_2$Cl$_2$ (37 mg, 44.7 μmol) was replaced by nitrogen for 3 times. The mixture was stirred in nitrogen atmosphere for 12 hours at 90° C. LCMS showed that raw materials were consumed completely, and target molecular ion peak were detected. The reaction solution was concentrated to remove solvent, then dispersed in 10 mL water, and extracted by DCM:MeOH (10:1, 30 mL*3). Organic phases were combined, washed by saturated saline solution (40 mL), dried by hydrous sodium sulfate, filtered, and distilled under reduced pressure to provide coarse product, which was purified by chromatographic column method (SiO$_2$, DCM:MeOH=1:0~20:1) to provide compound 7-4. LCMS (ESI) m/z: 410.2[M+H]$^+$.

Step 4: In argon atmosphere, Pd/C (10%, 0.05 g) was added into methanol (10 mL) solution containing compound 7-4 (0.15 g, 366.3 μmol). The mixture was replaced by hydrogen for 3 times, and then stirred for 16 hours in hydrogen atmosphere (15 psi) at 25° C. LCMS showed raw materials were consumed completely, and target molecular ion peaks were detected. The reaction solution was filtered, and concentrated to provide compound 7-5, which was directly used in following reactions without purification. LCMS (ESI) m/z: 412.2[M+H]$^+$.

Step 5: Dichloromethane solution (10 mL) containing compound 7-5 (0.13 g, 315.9 μmol) and TFA (4 mL) was replaced by nitrogen for 3 times, and then stirred for 30 minutes at 25° C. LCMS showed raw materials were consumed completely, and target molecular ion peaks were detected. The reaction solution and remove solvent to provide compound 7-6 (130 mg, TFA salt), which was directly used in following reactions without purification. LCMS (ESI) m/z: 312.1[M+H]$^+$.

Step 6: EDCI (88 mg, 458.4 μmol), HOBt (62 mg, 458.4 μmol), and DIEA (119 mg, 916.8 μmol, 160 μL) were added into DMF (4 mL) solution containing (1S)-2,2-bifluorocyclopropyl formic acid (37 mg, 305.6 μmol) then stirred to react for 5 minutes at 25° C., then added with compound 7-6 (0.13 g, 305.6 μmol, TFA salt), and stirred for 16 hours at 25° C. LCMS showed that raw materials were consumed completely, and target molecular ion peaks were detected. The coarse product was separated (chromatographic column: Waters Xbridge 150*25 5 μm; mobile phase: [H$_2$O (10 mM NH$_4$HCO$_3$)-ACN]; B (CH$_3$CN) %: 20%-50%, 7 min) and chiral separation (chromatographic column: DAICEL CHIRALPAK AD (250 mm*30 mm, 10 μm); mobile phase, A %: (0.1% NH$_3$H$_2$O EtOH); B (CO$_2$) %: (40%-40%) to provide compound 7-7, SFC retention time: 3.714 min.

$^1$H NMR (400 MHz, CDCl$_3$) δ=9.59 (br d, J=12.05 Hz, 1H), 7.34-7.57 (m, 2H), 6.70-6.84 (m, 1H), 4.06-4.21 (m,

2H), 3.92-3.99 (m, 1H), 3.74-3.92 (m, 2H), 1.81-2.38 (m, 8H), 1.59 (dtd, J=11.36, 7.62, 7.62, 3.76 Hz, 1H), 1.08-1.24 (m, 2H), 0.79-0.96 (m, 2H). LCMS (ESI) m/z: 416.0[M+H]⁺. Separation was performed to provide compound 7-8, SFC retention time: 4.468 min. ¹H NMR (400 MHz, CDCl₃) δ=9.48 (br s, 1H), 7.34-7.54 (m, 2H), 6.76 (br d, J=7.03 Hz, 1H), 4.03-4.25 (m, 2H), 3.73-3.99 (m, 3H), 2.50 (ddd, J=16.81, 13.18, 8.16 Hz, 1H), 1.80-2.40 (m, 8H), 1.53-1.66 (m, 1H), 1.05-1.23 (m, 2H), 0.80-0.95 (m, 2H). LCMS (ESI) m/z: 416.0[M+H]⁺.

Example 7

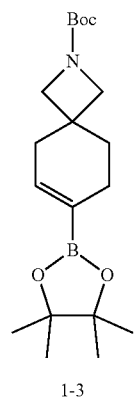

1-3

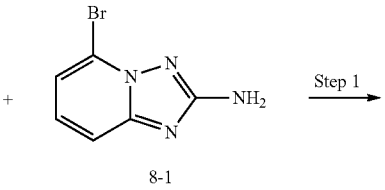

8-1

Step 1 →

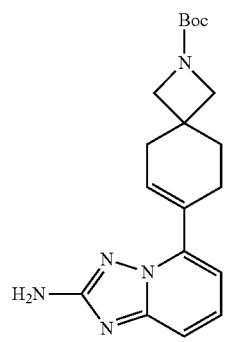

8-2

Step 2 →

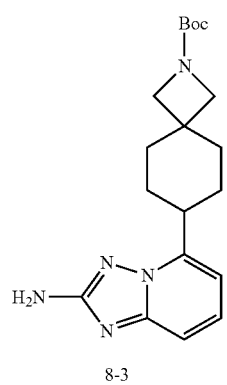

8-3

Step 3 →

-continued

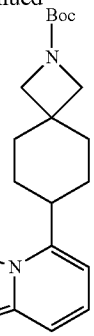

Step 4 →

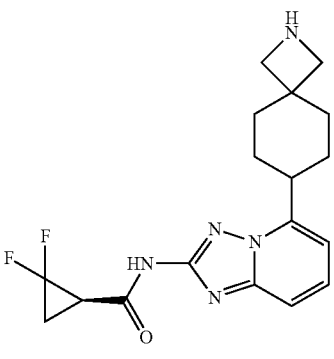

8-4

Step 5 →

8-5

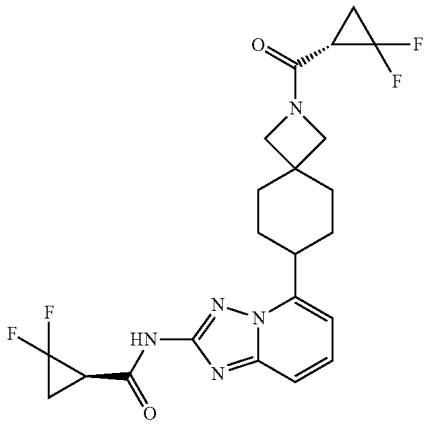

8-6

Step 1: In nitrogen atmosphere, mixed dioxane (40 mL) and water (10 mL) solution containing compound 8-1 (1.11 g, 5.21 mmol), compound 1-3, potassium carbonate (2.16 g, 15.6 mmol), and 1,1'-Bis(diphenylphosphino)ferrocene-palladium(II)dichloride dichloromethane (425 mg, 520.6 μmol) was replaced by nitrogen for 3 times, and then heated to 90° C. to react for 3 hours. LC-MS showed reaction was complete. The reaction solution was concentrated under reduced pressure to provide residues, which were separated by rapid column (04% methanol/dichloromethane) to provide compound 8-2. LCMS (ESI) m/z: 356.3[M+H]⁺.

Step 2: Under the protection of N₂ atmosphere, compound 8-2 (2 g, 5.6 mmol) was dissolved into methanol (100 mL) solution, added with catalyst, that is, dry palladium/carbon (0.5 g, 10%), and replaced by hydrogen for 3 times. The reaction solution was stirred for 12 hours in the condition of hydrogen pressure (30 Psi) and reaction temperature of 30°

C. LC-MS showed 50% of the raw materials were remained. The catalyst was removed by filtration, new catalyst, that is, dry palladium/carbon (1 g) was added, and the reaction was continued for 3 hours. LCMS showed that reaction was complete. The solid was filtered by diatomite to provide filtrate, which was concentrated under reduced pressure to provide compound 8-3. LCMS (ESI) m/z: 358.2[M+H]⁺.

Step 3: (1R)-2,2-difluorocyclopropyl carboxylic acid (282 mg, 2.3 mmol) was dissolved into pyridine (10 mL), added with EDCI (4.0 g, 21.0 mmol) and compound 8-3 (0.75 g, 2.1 mmol), and stirred for 12 hours at 10° C. LC-MS showed reaction was complete. The reaction solution was diluted by water (30 mL), and extracted with dichloromethane/methanol (10/1, 50 mL*3). The combined organic phases were washed by saturated saline solution (30 mL), dried by anhydrous sodium sulfate, filtered and concentrated under reduced pressure. Residues were separated by rapid silicon gel column (0-3% methanol/dichloromethane), and then beating-purified by EtOAc to provide compound 8-4. LCMS (ESI) m/z: 462.3[M+H]⁺.

Step 4: Compound 8-4 (300 mg, 650.1 μmol) was dissolved into dichloromethane (5 mL), added with hydrochloric acid/EtOAc (4 M, 10 mL), and left to react for half-hour at 15° C. LC-MS showed that reaction was complete. The reaction solution was concentrated to provide compound 8-5 (hydrochloride). LCMS (ESI) m/z: 362.2[M+H]⁺.

Step 5: Compound 8-5 (100 mg, 251.4 μmol, HCl) was dissolved into N,N-dimethyformamide (5 mL), added with HOBt (51 mg, 377.0 μmol) and EDCI (72.28 mg, 377.0 μmol), then added with (1S)-2,2-difluorocyclopropyl carboxylic acid (34 mg, 276.5 μmol) and diisopropylethylamine (65 mg, 502.7 μmol), and left to react for 12 hours at 15° C. LC-MS showed that reaction was complete. The reaction solution was concentrated under reduced pressure, and the residues were processed by preparative HPLC (neutral system) to provide compound 8-6. ¹H NMR (400 MHz, METHANOL-d₄) δ 7.59-7.67 (m, 1H), 7.51 (d, J=8.78 Hz, 1H), 7.01 (br d, J=7.53 Hz, 1H), 3.92-4.20 (m, 2H), 3.79-3.88 (m, 1H), 3.67-3.77 (m, 1H), 3.43-3.57 (m, 1H), 2.81 (br s, 1H), 2.62 (dq, J=7.78, 11.96 Hz, 1H), 2.07-2.24 (m, 5H), 1.52-2.05 (m, 7H). LCMS (ESI) m/z: 466.2[M+H]⁺.

The following compounds 8-7 and 8-8 having the following characteristic data were obtained from compound 8-5 as common intermediate by using the same synthesis and separation methods as those used for compound 8-6 (carboxylic acids compounds with different substituents from compound 8-6 were added)

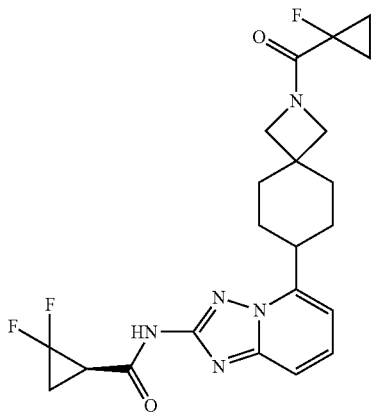

8-7

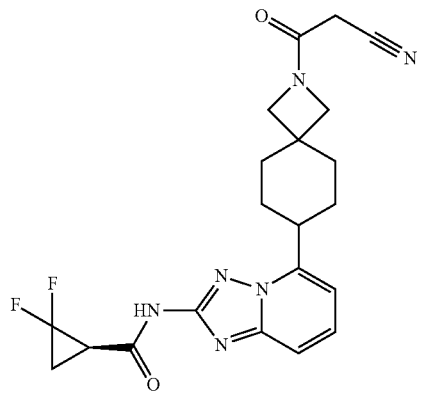

8-8

Compound 8-7, Coarse product was processed by preparative HPLC (neutral system) for purification. ¹H NMR (400 MHz, METHANOL-d₄) δ 7.59-7.66 (m, 1H), 7.51 (d, J=8.78 Hz, 1H), 6.97-7.04 (m, 1H), 4.30 (d, J=4.27 Hz, 1H), 4.18 (d, J=4.27 Hz, 1H), 3.87 (s, 1H), 3.76 (s, 1H), 3.49 (br t, J=11.80 Hz, 1H), 2.81 (br s, 1H), 2.05-2.28 (m, 5H), 1.74-1.96 (m, 3H), 1.53-1.70 (m, 2H), 1.23-1.33 (m, 4H). LCMS (ESI) m/z: 448.2[M+H]⁺.

Compound 8-8, Coarse product was processed by preparative HPLC (neutral system) for purification. ¹H NMR (400 MHz, METHANOL-d₄) δ 7.59-7.67 (m, 1H), 7.51 (d, J=8.78 Hz, 1H), 7.00 (t, J=7.40 Hz, 1H), 4.61 (s, 2H), 3.69-4.11 (m, 4H), 3.41-3.54 (m, 1H), 2.82 (br s, 1H), 2.04-2.26 (m, 5H), 1.72-1.93 (m, 3H), 1.61 (q, J=11.80 Hz, 2H). LCMS (ESI) m/z: 429.0[M+H]⁺.

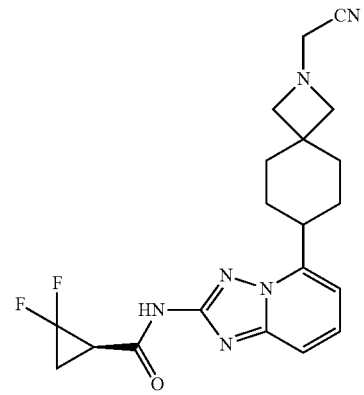

8-9

Synthesis of compound 8-9: Intermediate 8-5 (100 mg, 227.6 μmol, TFA) was dissolved into N,N-dimethylformamide (5 mL), added with potassium carbonate (94 mg, 682.7 μmol) and 2-bromoacetonitrile (30 mg, 250.3 μmol), and stirred for 12 hours at 10° C. LC-MS showed reaction was complete. The reaction solution was diluted by water (5 mL), and extracted by dichloromethane/methanol (10/1, 10 mL). The organic phases were washed by saturated saline solution (10 mL), dried by anhydrous sodium sulfate, then filtered and concentrated under reduced pressured under reduced pressure. Residues were processed by preparative HPLC (neutral system) for purification, to provide compound 8-9. ¹H NMR (400 MHz, METHANOL-d₄) δ 7.59-7.66 (m, 1H), 7.50 (d, J=8.78 Hz, 1H), 6.99 (d, J=7.53 Hz, 1H), 3.62 (s, 2H), 3.46 (br t, J=12.05 Hz, 1H), 3.33 (s, 2H), 3.21 (s, 2H), 2.80 (br s, 1H), 2.14 (br d, J=9.79 Hz, 5H), 1.82-1.95 (m, 1H), 1.52-1.77 (m, 4H). LCMS (ESI) m/z: 401.0[M+H]⁺.

Example 8

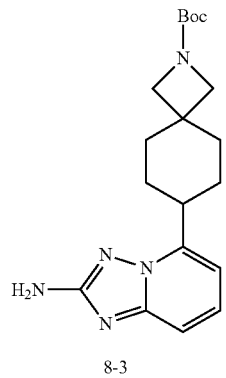

8-3

Step 1 →

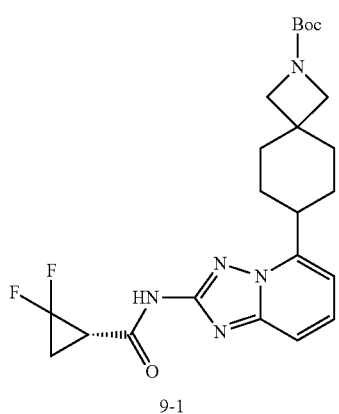

9-1

Step 2 →

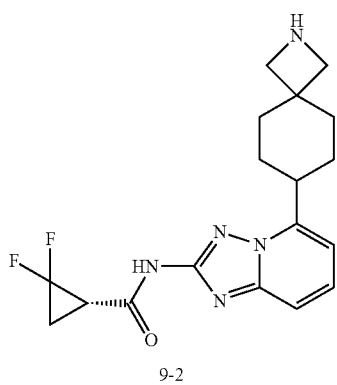

9-2

Step 3 →

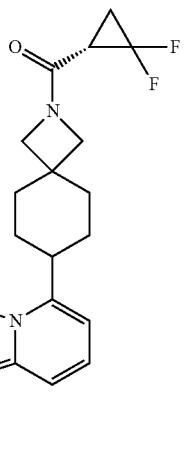

9-3

Step 1: (S)-2,2-difluorocyclopropyl carboxylic acid (1.13 g, 9.2 mmol) was dissolved into pyridine (150 mL), added with EDCI (16.1 g, 84 mmol) and compound 8-3 (3 g, 8.4 mmol), and stirred for 12 hours at 10° C. LC-MS showed that reaction was complete. The reaction solution was diluted by aq (100 mL), and then extracted by dichloromethane/methanol (10/1, 100 mL*3). The combined organic phases were washed by saturated saline solution (30 mL), then dried by anhydrous sodium sulfate, filtered and concentrated under reduced pressure. Residues were separated by rapid column (0-3% methanol/dichloromethane), and then beating-purified by using EtOAc to provide compound 9-1. LCMS (ESI) m/z: 462.3[M+H]⁺.

Step 2: Compound 9-1 (2.3 g, 4.9 mmol) was dissolved into dichloromethane (5 mL), added with hydrochloric acid/EtOAc (4 M, 20 mL), and left to react for half-hour at 15° C. LC-MS showed that reaction was complete, and target molecular ion peaks were detected. The precipitated solid was filtered, and dried to provide compound 9-2 (hydrochloride). LCMS (ESI) m/z: 362.2[M+H]⁺.

Step 3: Compound 9-2 (1.23 g, 3.1 mmol, HCl) was dissolved into N,N-dimethylformamide (20 mL), add HOBt (626 mg, 4.6 mmol) and EDCI (889 mg, 4.6 mmol), then added with (1S)-2,2-difluorocyclopropyl carboxylic acid (414.92 mg, 3.40 mmol) and diisopropylethylamine (798.70 mg, 6.18 mmol), and left to react for 12 hours at 15° C. LC-MS showed that reaction was complete. The reaction solution was diluted by water (10 mL), and extracted by dichloromethane/methanol (10/1, 50 mL). Organic phases were washed by saturated saline solution (10 mL), dried by anhydrous sodium sulfate, filtered and concentrated under reduced pressure. Residues were processed by preparative HPLC (neutral system) to provide compound 9-3. ¹H NMR (400 MHz, METHANOL-d₄) δ 7.63 (dd, J=7.53, 8.78 Hz, 1H), 7.51 (d, J=8.78 Hz, 1H), 7.01 (br d, J=7.28 Hz, 1H), 3.92-4.19 (m, 2H), 3.79-3.87 (m, 1H), 3.67-3.76 (m, 1H), 3.44-3.55 (m, 1H), 2.52-2.92 (m, 2H), 1.53-2.25 (m, 12H). LCMS (ESI) m/z: 466.1[M+H]⁺.

The following compounds 9-4, 9-5 having the following characteristic data were obtained from compound 9-2 as common intermediate by using the same synthesis and separation methods as those used for compound 9-3 (carboxylic acids compounds with different substituents from compound 9-3 were added):

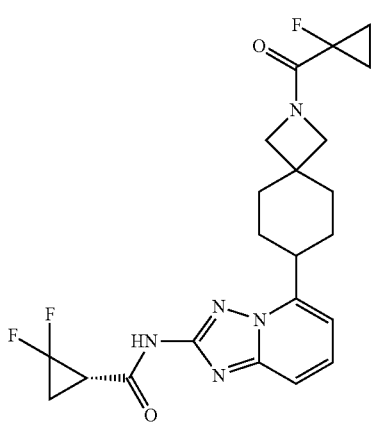

9-4

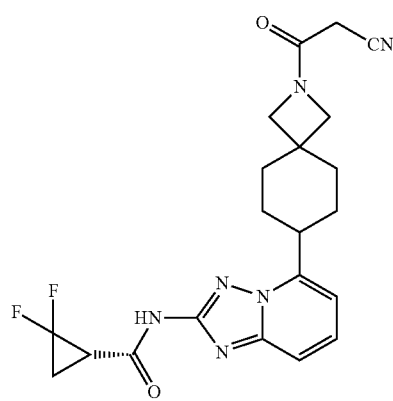

9-5

Compound 9-4: $^1$H NMR (400 MHz, METHANOL-d$_4$) δ 7.58-7.68 (m, 1H), 7.51 (d, J=8.78 Hz, 1H), 6.97-7.05 (m, 1H), 4.30 (d, J=4.02 Hz, 1H), 4.18 (d, J=4.27 Hz, 1H), 3.87 (s, 1H), 3.76 (s, 1H), 3.49 (br t, J=11.80 Hz, 1H), 2.82 (br s, 1H), 2.07-2.25 (m, 5H), 1.73-1.95 (m, 3H), 1.51-1.70 (m, 2H), 1.24-1.35 (m, 4H). LCMS (ESI) m/z: 448.2[M+H]$^+$.

Compound 9-5: $^1$H NMR (400 MHz, METHANOL-d$_4$) δ 7.58-7.68 (m, 1H), 7.51 (d, J=9.03 Hz, 1H), 7.00 (t, J=7.53 Hz, 1H), 4.61 (s, 2H), 3.69-4.10 (m, 4H), 3.43-3.55 (m, 1H), 2.82 (br s, 1H), 2.05-2.25 (m, 5H), 1.72-1.97 (m, 3H), 1.51-1.69 (m, 2H). LCMS (ESI) m/z: 429.0[M+H]$^+$.

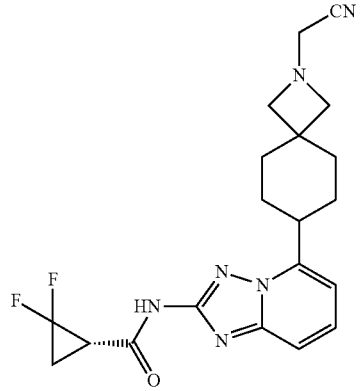

9-6

Synthesis of compound 9-6: The intermediate compound 9-2 (190 mg, 525.8 μmol) was dissolved into N,N-dimethylformanide (5 mL), potassium carbonate (218 mg, 1.6 mmol) and 2-bromoacetonitrile (70 mg, 578.3 μmol) were added, reaction solution was stirred for 12 hours at 10° C. LC-MS showed that reaction was complete. Reaction solution was diluted with water (5 mL), extracted by dichloromethane/methanol (10/1, 10 mL), washed organic phase by saturated saline solution (10 mL), dried by anhydrous sodium sulfate, filtered and concentrated under reduced pressure. Residues were processed by preparative HPLC (neutral system) for purification, to provide compound 9-6. $^1$H NMR (400 MHz, METHANOL-d$_4$) δ 7.58-7.66 (m, 1H), 7.50 (d, J=8.53 Hz, 1H), 6.99 (d, J=7.28 Hz, 1H), 3.62 (s, 2H), 3.46 (br t, J=11.42 Hz, 1H), 3.33 (s, 2H), 3.21 (s, 2H), 2.81 (br s, 1H), 2.14 (br d, J=10.29 Hz, 5H), 1.81-1.95 (m, 1H), 1.51-1.78 (m, 4H). LCMS (ESI) m/z: 401.2[M+H]$^+$.

Example 9

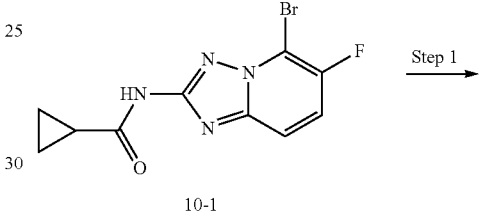

10-1

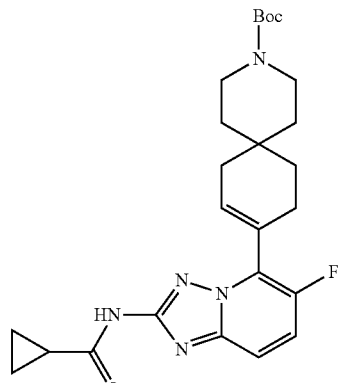

10-2

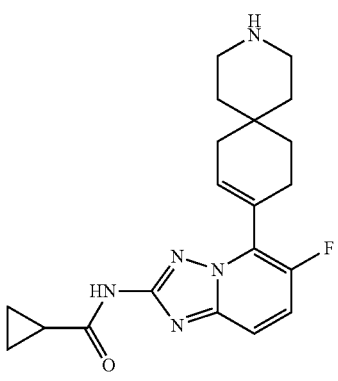

10-3

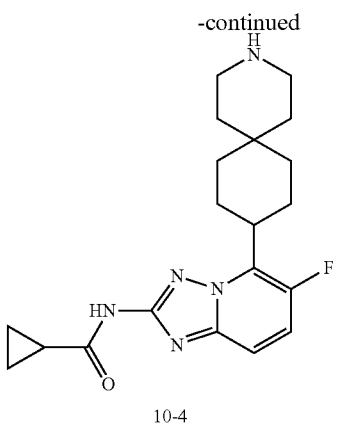

10-4

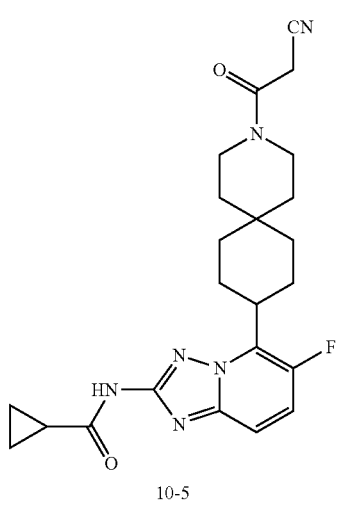 [SMILES: N#CCC(=O)N1CCC2(CCC(c3c(F)ccc4nc(NC(=O)C5CC5)nn34)CC2)CC1]

10-5

Step 1: Mixed dioxane (12 mL) and H₂O (3 mL) containing compound 10-1 (100 mg, 334.3 μmol), compound 3-3 (126 mg, 334.3 μmol), Pd(dppf)Cl₂ (25 mg, 33.4 μmol), and potassium carbonate (139 mg, 1.00 mmol) was replaced by nitrogen by 3 times, and stirred in nitrogen atmosphere for 2 hours at 90° C. LCMS showed that raw materials were consumed completely, and the main peak was detected as target molecular ion peak. The reaction solution was filtered and concentrated to remove solvent, and separated and purified by using a preparation plate to provide compound 10-2. LCMS (ESI) m/z: 470.4[M+H]⁺.

Step 2: Dichloromethane (1 mL) solution containing compound 10-2 (130 mg, 276.9 μmol) and HCl/EtOAc (4 M, 2 mL) was stirred for 5 minutes at 25° C. LCMS showed that raw materials were consumed completely, and the main peak was detected as target molecular ion peak. Reaction solution was concentrated under reduced pressure to provide yellow solid compound 10-3 (120 mg, hydrochloride), which was directed used in following reactions without purification. LCMS (ESI) m/z: 370.6[M+H]⁺.

Step 3: In nitrogen atmosphere, Pd/C (20 mg, 10%) was added into MeOH (25 mL) solution containing compound 10-3 (120 mg, 295.6 μmol, hydrochloride). Suspension was replaced by hydrogen for 3 times, and then stirred for 12 hours in nitrogen atmosphere (15 Psi), 25° C. LCMS showed that raw materials were consumed completely, and main peak was detected as target molecular ion peak. Reaction solution was filtered, concentrated under reduced pressure to remove the solvent, and provide compound 10-4 (130 mg, hydrochloride), which was directly used in following reactions without purification. LCMS (ESI) m/z: 372.3[M+H]⁺.

Step 4: DMF (5 mL) solution containing compound 10-4 (130 mg, 318.7 μmol, hydrochloride), 2-cyanoacetic acid (33 mg, 382.4 μmol), EDCI (92 mg, 478 μmol), HOBt (65 mg, 478 μmol) and DIEA (206 mg, 1.6 mmol, 277.6 μL) was stirred for 12 hours at 25° C. LCMS showed that raw materials were consumed completely, and target molecular ion peaks were detected. Reaction solution was concentrated under reduced pressure to remove solvent, and then separated to provide compound (neutral system) 10-5. ¹H NMR (400 MHz, METHANOL-d₄) δ=7.57-7.65 (m, 1H), 7.49-7.55 (m, 1H), 3.59-3.81 (m, 3H), 3.44-3.54 (m, 2H), 3.34-3.38 (m, 2H), 2.48 (br s, 2H), 1.81-2.04 (m, 5H), 1.64-1.77 (m, 2H), 1.36-1.58 (m, 4H), 0.86-1.12 (m, 4H). LCMS (ESI) m/z: 439.1[M+H]⁺.

Biological Activity Test

Experiment 1: In Vitro Test of Activities of Jak1, Jak2, Jak3, Tyk2 Kinases

Materials

Recombinant human JAK1, JAK2, JAK3, Tyk2 protease, most of the apparatuses and reagents were supplied by Eurofins (UK).

Methods

Dilution of JAK2, JAK3 and TYK2: 20 mM 3-(N-morpholine)propanesulfonic acid (MOPS), 1 mM EDTA, 0.01% Brij-35.5% glycerol, 0.1% β-mercaptoethanol, 1 mg/mL BSA; Dilution of JAK1: 20 mM TRIS, 0.2 mM EDTA, 0.1% β-mercaptoethanol, 0.01% Brij-35.5% glycerol. All the compounds were prepared into 100% DMSO solution and the concentration reached final measured concentration of 50 times. The test compound was diluted by a 3-fold concentration gradient, and the final concentration was 9 concentrations from 10 μM to 0.001 μM. The content of DMSO in the detect reaction was 2%. The stock solution of this compound was added into wells as a first component, then the other components were added as the following detailed process.

Enzyme Reaction of JAK1(h)

JAK1(h) was incubated with 20 mM Tris/HC pH7.5, 0.2 mM EDTA, 500 μM MGEEPLYWSFPAKKK, 10 mM magnesium acetate and [γ-³³P]-ATP (activities and concentration were customized as required). Mixture of Mg/ATP was added to start reaction, which was stopped by adding 0.5% phosphoric acid after 40 minutes incubation at room temperature. Then 10 μL of the reaction was dispersed on the P30 filter pad, washed with 0.425% phosphoric acid for three times and with methanol for one time within 4 minutes, dried, and scintillate counted.

Enzyme Reaction of JAK2(h)

JAK2(h) was incubated with 8 mM MOPS pH 7.0, 0.2 mM EDTA, 100 μM KTFCGTPEYLAPEVRREPRILSEE-EQEMFRDFDYIADWC, 10 mM magnesium acetate and [γ-³³P]-ATP (activities and concentration were customized as required). Mixture of Mg/ATP was added to start reaction, which was stopped by adding 0.5% phosphoric acid after 40 minutes incubation. Then 10 μL of the reaction solution was dispersed on the P30 filter pad, washed with 0.425% phosphoric acid for three times and with methanol for one time within 4 minutes, dried, and scintillate counted.

Enzyme Reaction of JAK3(h)

JAK3(h) was incubated with 8 mM MOPS pH 7.0, 0.2 mM EDTA, 500 μM GGEEEEYFELVKKKK, 10 mM magnesium acetate and [γ-33P]-ATP (activities and concentration were customized as required). Mixture of Mg/ATP was added to start reaction, which was stopped by adding 0.5% phosphoric acid after 40 minutes incubation. Then 10 μL of the reaction solution was dispersed on the P30 filter pad, washed with 0.425% phosphoric acid for three times and with methanol for one time within 4 minutes, dried, and scintillate counted.

Enzyme Reaction of TYK2(h)

TYK2(h) was incubated with 8 mM MOPS pH 7.0, 0.2 mM EDTA, 250 M GGMEDIYFEFMGGKKK, 10 mM magnesium acetate and [γ-³³P]-ATP (activities and concentration were customized as required). Mixture of Mg/ATP was added to start reaction, which was stopped by adding 0.5% phosphoric acid after 40 minutes incubation. Then 10 µL of the reaction solution was dispersed on the P30 filter pad, washed with 0.425% phosphoric acid for three times and with methanol for one time within 4 minutes, dried, and scintillate counted.

Data Analyses

Results of $IC_{50}$ were provided by analysis of XLFIT5 (205 formula) from IDBS, and details are shown in table 1.

TABLE 1

The test results of compound screening in vitro

| Compounds | TYK2 ($IC_{50}$, nM) | JAK1 ($IC_{50}$, nM) | JAK2 ($IC_{50}$, nM) | JAK3 ($IC_{50}$, nM) |
|---|---|---|---|---|
| 1-7 | 38 | 6 | 60 | 3834 |
| 1-8 | 27 | 14 | 78 | 2939 |
| 1-9 | 366 | 34 | 315 | >10000 |
| 1-10 | 311 | 32 | 426 | >10000 |
| 1-11 | 18 | 15 | 198 | >10000 |
| 1-12 | 360 | 45 | 527 | >10000 |
| 1-13 | 36 | 3 | 37 | 1517 |
| 1-14 | 134 | 12 | 144 | 5035 |
| 1-15 | 106 | 20 | 208 | 9669 |
| 1-16 | 581 | 114 | 1020 | >10000 |
| 1-17 | 371 | 65 | 791 | >10000 |
| 3-7 | 26 | 3 | 40 | 1002 |
| 3-8 | 26 | 20 | 80 | 2323 |
| 3-9 | 155 | 54 | 294 | >10000 |
| 4-6 | 307 | 170 | 2008 | 8448 |
| 4-7 | 194 | 436 | 7685 | >10000 |
| 4-8 | >10000 | 244 | 3711 | 364 |
| 5-7 | 67 | 31 | 324 | 5759 |
| 5-8 | 692 | 75 | 789 | 7349 |
| 5-9 | 278 | 68 | 520 | >10000 |
| 5-10 | 1526 | 131 | 2730 | >10000 |
| 6-7 | 829 | 63 | 998 | 9391 |
| 6-8 | 570 | 381 | 1924 | >10000 |
| 7-7 | 830 | 63 | 1632 | >10000 |
| 7-8 | 404 | 176 | 2313 | >10000 |
| 8-6 | 127 | 14 | 110 | 7637 |
| 8-7 | 1032 | 63 | 5463 | >10000 |
| 8-8 | 109 | 60 | 1376 | >10000 |
| 8-9 | 1329 | 52 | 3672 | >10000 |
| 9-3 | 105 | 7 | 292 | >10000 |
| 9-4 | 1186 | 253 | 982 | >10000 |
| 9-5 | 175 | 224 | 624 | >10000 |
| 9-6 | 1388 | 432 | 1174 | >10000 |
| 10-5 | 430 | 336 | 812 | 5410 |

Conclusion: The compounds in the present application showed good selectivity inhibition to JAK1 and/or TYK2 in the in vitro test of activities of the 4 subtypes of kinases JAK1, JAK2, JAK3 and TYK2 kinases.

Experiment 2: Pharmacokinetics (PK) Test

The clear solution obtained by dissolving the test compound was injected into the tail vein and intragastrically administered to male mice (C57BL/6) or rats (SD) (overnight fasting, 7-8 weeks old). After administration of the test compound, for the intravenous group (2 mg/kg) at 0.117, 0.333, 1, 2, 4, 7 and 24 hours and the intravenous group (15 mg/kg) at 0.25, 0.5, 1, 2, 4, 8 and 24 hours, blood was collected from the mandibular vein and centrifuged to obtain plasma. LC-MS/MS method was used to determine the plasma concentration, and the WinNonlin™ Version 6.3 pharmacokinetic software was used to calculate the relevant pharmacokinetics by the non-compartmental model linear logarithmic ladder method Parameters. The test results are as follows:

TABLE 2-1

The result of PK test of compound 1-11 in mice

| PK parameters | Results |
|---|---|
| $T_{1/2}$ (hr) | 2.99 |
| $C_{max}$ (nM) | 5745 |
| $AUC_{0-inf}$ (nM · hr) | 9918 |
| Bioavailability (%)[a] | 42.1% |

TABLE 2-2

The result of PK test of compound 1-13 in mice

| PK parameters | Results |
|---|---|
| $T_{1/2}$ (hr) | 1.61 |
| $C_{max}$ (nM) | 5105 |
| $AUC_{0-inf}$ (nM · hr) | 9917 |
| Bioavailability (%)[a] | 38.1% |

TABLE 2-3

The result of PK test of compound 3-7 in mice

| PK parameters | Results |
|---|---|
| $T_{1/2}$ (h) | 4.74 |
| $C_{max}$ (nM) | 7380 |
| $AUC_{0-inf}$ (nM · h) | 17969 |
| Bioavailability (%)[a] | 50.1% |

Note: $T_{1/2}$: half-life; $C_m$x: peak concentration;
$AUC_{0-inf}$: AUC of plasma concentration-time from time 0 to infinity;

Conclusion: Compound in the present application has good bioavailability, high exposure, and excellent in vivo efficacy.

Experiment 3: In Vivo Efficacy Study of Collagen-Induced Arthritis (CIA) in Mice Experimental Purpose:

Rheumatoid arthritis (RA) is a type of multiple autoimmune diseases with a global incidence rate of about 1%, which leads to inflammation, damages and malformation of arthrosis, and in serious situation, leads to systemic inflammation reactions. Studies of drugs for RA treatment can help ease the symptom of rheumatoid arthritis, and can improve quality of life of a patient. Collagen-induced mice arthritis model is an animal model often used to evaluate the efficacy of drugs in the treatment of RA. Its pathogenesis and symptoms are significantly related to RA disease. The reactivity of B cells and T cells to bone collagen are activated by injecting type II collagen in the model, and activated B cells and T cells enter the joint site to cause joint damage, which triggers a series of symptoms similar to human rheumatoid arthritis. Evaluation of drug treatment for rheumatoid before clinical in the process of candidate compounds for arthritis, collagen-induced arthritis in mice is often used to evaluate its effectiveness.

The purpose of the experiment is to study the therapeutic effects of compound 1-13, compound 3-7 and reference compound Filgotinib in collagen-induced arthritis of mice, thus to provide pre-clinical pharmacodynamic information for subsequent clinical studies.

Experimental Methods:

1. Type II Collagen/Complete Freund's Adjuvant Immune

Preparation of acetic acid: 2N acetic acid was diluted to 100 mM, filtered by 0.22 micron filter membrane, and stored at 4° C.

Bovine type 2 collagen (CII) was dissolved in 100 mM acetic acid solution, then stored overnight at 4° C. Final concentration of the collagen is 8 mg/ml.

Preparation of emulsion: the overnight stored CII solution was mixed with equal volume of complete Freund's adjuvant, and homogenized on ice on a high-speed homogenizer at 30,000 revolutions per minute for approximately 60 minutes until the solution forms a stable emulsion.

2. Induction of Arthritis:

Mice were randomly divided into different treatment groups. The day for the first immunization is recorded as day 0, and the subsequent days are marked in order.

DBA/1 mice were anesthetized with isoflurane and injected with 50 ml prepared collagen emulsion (containing 200 mg CII) subcutaneously (2-3 cm from the root of the tail). At day 21, the tail was injected with the same volume of collagen emulsion in the same way. The mice in the normal group was not immunized.

3. Designs of Administration and Dosages

At day 28, when average clinical score is about 1, 50 mice with moderate incidence were selected ad randomly divided into 5 treatment groups based on body weights and scores, with each group having 8 mice.

Dexamethasone (Dex.) was used as a reference drug for measuring whether the model was successfully established, with a dose of 0.3 mg/kg (a commonly used dose in a CIA model). In addition, according to the results of preliminary experiments, the dosages of test compound 1-13, compound 3-7 and reference compound Filgotinib were determined and shown in table 3-1: the first group is of normal mice without any treatment; the second group is a blank group given only solvent; the third group is given a dose of 0.3 mg/kg of dexamethasone; the sixth group, the seventh group and the eighth group are given the dose of 15 mg/kg. They were administered twice a day for a total of 14 days.

TABLE 3-1

Design of dosages and grouping

| Groups | Names of test drugs | Numbers | Administration route | Concentration mg/mL | Dosage mg/kg | Administration frequency |
|---|---|---|---|---|---|---|
| G1 | Normal | 5 | N/A | N/A | N/A | N/A |
| G2 | Blank (Solvent control) | 8 | p.o. | N/A | N/A | bid, 14 days |
| G3 | dexamethasone (Dex.) | 8 | p.o. | 0.03 | 0.3 | qd, 14 days |
| G6 | Compound 1-13 | 8 | p.o. | 1.5 | 15 | bid, 14 days |
| G7 | Compound 3-7 | 8 | p.o. | 1.5 | 15 | bid, 14 days |
| G8 | Filgotinib | 8 | p.o. | 1.5 | 15 | bid, 14 days |

Note:
PO: oral;
bid: twice a day;
qd: once a day.

4. Measuring of Incidence Index of Arthritis

Clinical observation: from 7 days before immunization to the 21st day after immunization, the basic health status and weight changes of DBA/1 mice was observed daily (recorded once a week). After the 22nd day, the health status, the incidence circumstances, and weight changes of the mice was observed every day (recorded at least three times a week) until the end of the experiment.

Clinical scoring: the incidence of the mice was observed every day after boosting the immune function. After the mice was attacked (showing clinical symptoms of arthritis), the incidence was scored from 0-4 as scoring standard according to different levels of the disease (redness, joint deformation). The highest score for each limb is 4, and the highest score for each animal is 16. The scoring standards are shown in Table 3-2. The scoring was performed three times a week.

TABLE 3-2

Clinical scoring criteria of arthritis

| Scores | Clinical symptoms |
|---|---|
| 0 | No erythema and swelling |
| 1 | Erythema or slight swelling near tarsal bone or ankle or metatarsal bone, and swelling on one toe |
| 2 | Slight erythema and swelling on ankle and metatarsal bone, or swellings on more than two toes |
| 3 | Moderate erythema and swelling on ankle and wrist joints and metatarsal bone |
| 4 | Severe swelling on all of ankle and wrist joints, metatarsal bone and toes |

5. Statistic Processing

The experimental data is expressed as mean standard error (Mean SEM), and the area under the curve (AUC) is analyzed by one-way ANOVA. $P<0.05$ is considered to be significant.

Experimental Results:

1. Clinical Scoring and Incidence:

At day 28 after the first immune (day 7 after the second immune), mice began to show clinical symptoms of arthritis. The administration was started at day 28. The detailed experimental results were showed in table 5 and FIG. 1. The average clinical score of the solvent control group gradually increased, reaching 5.8 on the 41st day, indicating the successful establishment of the collagen-induced arthritis model. Compounds 1-13, 3-7 and Filgotinib at the same dose of 15 mg/kg can significantly reduce the clinical scores of arthritis mice at the endpoint (day 41) of the experiment. The average score of compounds 1-13, 3-7 and Filgotinib at the same dosage dropped to 1.5, 3.0 and 5.6 points (see the values in Table 5), showing that compounds 1-13, 3-7 at 15 mg/kg can effectively reduce collagen-induced arthritis. Dexamethasone 0.3 mg/kg (G3 group) treatment can significantly inhibit the clinical score of collagen-induced arthritis, and from the 27th day, the clinical score is maintained at about 0.3 and on the 31st day (the clinical score drops to 0, see the value in Table 3-3) the curve and the normal group curve (G1 group) coincide until the end of the experiment. (see FIG. 1).

TABLE 3-3*

Average clinical scores of the present application

| Date | G2 Blank group | G3 Dex | G6 Compound1-13 | G7 Compound3-7 | G8 Filgotinib | G1 Normal |
|---|---|---|---|---|---|---|
| 21 | 0.00 ± 0.00 | 0.00 ± 0.00 | 0.00 ± 0.00 | 0.00 ± 0.00 | 0.00 ± 0.00 | 0.00 ± 0.00 |
| 24 | 0.00 ± 0.00 | 0.00 ± 0.00 | 0.00 ± 0.00 | 0.00 ± 0.00 | 0.00 ± 0.00 | 0.00 ± 0.00 |
| 27 | 0.38 ± 0.18 | 0.25 ± 0.16 | 0.50 ± 0.19 | 0.50 ± 0.19 | 0.25 ± 0.16 | 0.00 ± 0.00 |
| 28 | 0.50 ± 0.19 | 0.50 ± 0.27 | 0.63 ± 0.26 | 0.63 ± 0.26 | 0.63 ± 0.26 | 0.00 ± 0.00 |
| 29 | 1.38 ± 0.38 | 0.25 ± 0.16 | 1.00 ± 0.38 | 0.75 ± 0.25 | 0.88 ± 0.40 | 0.00 ± 0.00 |
| 31 | 2.50 ± 0.73 | 0.00 ± 0.00 | 1.38 ± 0.53 | 1.00 ± 0.33 | 1.88 ± 0.81 | 0.00 ± 0.00 |
| 34 | 4.25 ± 0.73 | 0.00 ± 0.00 | 1.50 ± 0.63 | 1.63 ± 0.38 | 2.63 ± 0.82 | 0.00 ± 0.00 |
| 36 | 4.75 ± 1.08 | 0.00 ± 0.00 | 1.75 ± 0.67 | 2.50 ± 0.46 | 3.88 ± 1.27 | 0.00 ± 0.00 |
| 38 | 5.38 ± 1.00 | 0.00 ± 0.00 | 1.88 ± 0.77 | 3.13 ± 0.58 | 4.88 ± 1.39 | 0.00 ± 0.00 |
| 41 | 5.75 ± 0.96 | 0.00 ± 0.00 | 1.50 ± 0.71 | 3.00 ± 0.60 | 5.63 ± 1.45 | 0.00 ± 0.00 |

*Note:
average clinical score ± standard error

Figure 2:
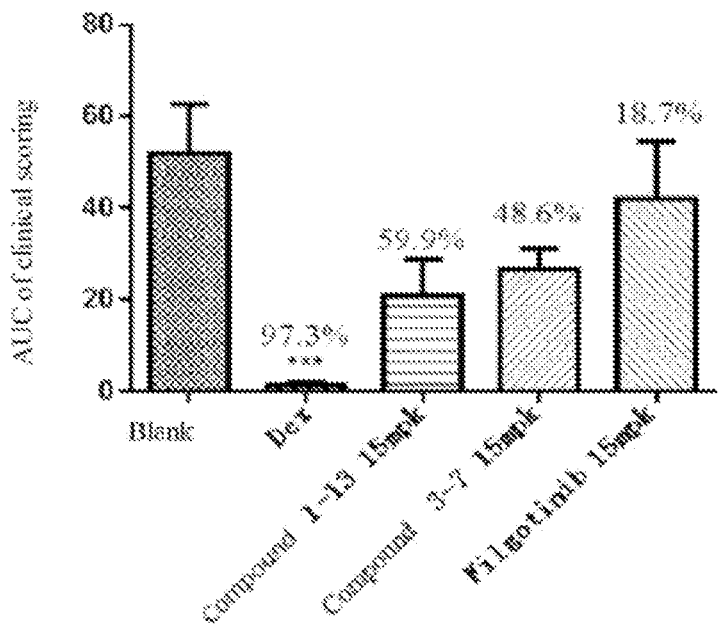
FIG. 2 The inhibitory rates of arthritis in mice calculated by the areas under the AUC in administration period.

By analyzing the clinical scoring curve of each animal in each group, the area under the curve (AUC) was calculated, and the inhibition rate of each administration group relative to the solvent control group was calculated by the AUC average between groups. The detailed results are shown in Table 3-4 and FIG. 2. Compounds 1-13, 3-7 and Filgotinib can reduce the clinical score AUC of arthritic animals at the same dose of 15 mg/kg, and the inhibition rates are 59.9%, 48.6% and 18.7%, respectively. Dexamethasone can also significantly reduce the clinical score of arthritis animals, with an inhibition rate of 97.3%.

TABLE 3-4*

AUC of incidence

| | G2 Blank group | G3 Dex | G6 Compound1-13 | G7 Compound3-7 | G8 Filgotinib |
|---|---|---|---|---|---|
| AUC ± SEM | 51.75 ± 10.97 | 1.38 ± 0.81 | 20.75 ± 8.05 | 26.63 ± 4.57 | 42.06 ± 12.50 |
| Inhibition rate | N/A | 97.3% | 59.9% | 48.6% | 18.7% |

Figure 3:
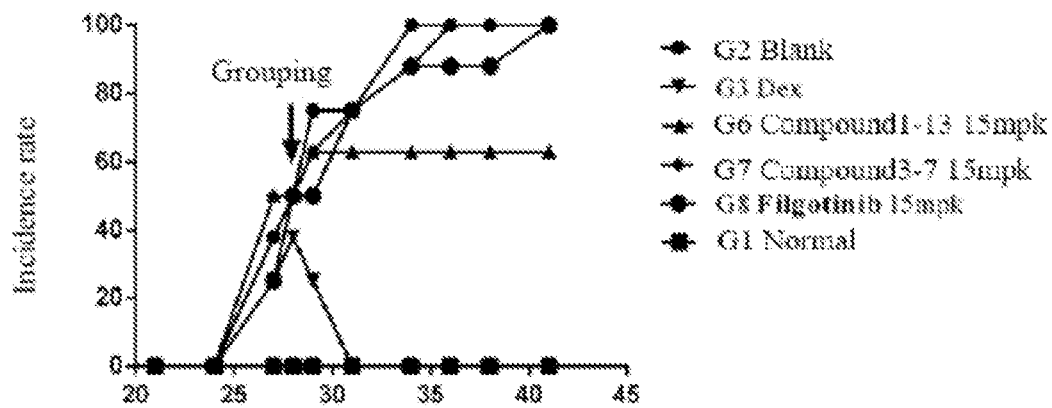
FIG. 3 The incidence rates of arthritis in mice in administration period.

*Note:
the value of the area under the curve is fitted according to the animal's clinical software Graphpad Prism ®, and they are the area under the incidence curve of each mouse in each group during the administration period. Inhibition rate = (average area under the curve in the blank group Value-the average of the area under the curve of the administration group)/the average of the area under the curve of the blank group Various treatment factors can also affect the incidence of collagen-induced arthritis. The detailed results of the experiment are shown in Table 7 and FIG. 3. The incidence for test compounds 1-13 reached 63% on day 29 and was kept until the end of the experiment (see specific values in table 3-5). The incidence for compound 3-7 reached 88% on the 34th day, and was kept at 100% till the end. The incidence of the Filgotinib group was decreased after the initial administration, and then gradually increased until 100% after the last administration. The incidence of arthritis in the solvent control group reached and maintained at 100% on the 34th day after immunization; and the incidence of the positive control dexamethasone 0.3 mg/kg group began to decrease after administration and decreased to 0% on the 31st day.

TABLE 3-5*

Incidence of the present application

| Date | G2 Blank group | G3 Dex | G6 Compound1-13 | G7 Compound3-7 | G8 Filgotinib | G1 Normal |
|---|---|---|---|---|---|---|
| 21 | 0% | 0% | 0% | 0% | 0% | 0% |
| 24 | 0% | 0% | 0% | 0% | 0% | 0% |
| 27 | 38% | 25% | 50% | 50% | 25% | 0% |
| 28 | 50% | 38% | 50% | 50% | 50% | 0% |
| 29 | 75% | 25% | 63% | 63% | 50% | 0% |
| 31 | 75% | 0% | 63% | 75% | 75% | 0% |
| 34 | 100% | 0% | 63% | 88% | 88% | 0% |
| 36 | 100% | 0% | 63% | 100% | 88% | 0% |
| 38 | 100% | 0% | 63% | 100% | 88% | 0% |
| 41 | 100% | 0% | 63% | 100% | 100% | 0% |

*Note:
incidence = the number of pathogenic animals in each group/the total number of animals in each group *100%

2. Body Weight

Figure 4:
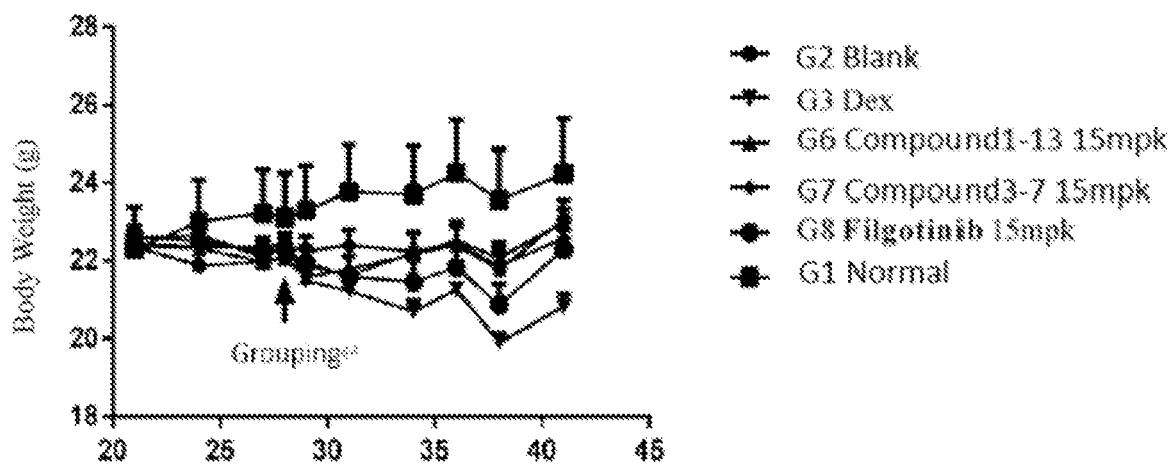
FIG. 4 Change in the body weight of mice with arthritis.

The detailed results of the experiment are shown in Table 8 and FIG. 4. Compared with the normal group, the weight of the mice after immunizing and modeling was reduced after immunization, and the weight of each administration group decreased from day 28 to day 34 (see FIG. 4), then began to recover slowly. The dexamethasone group had the largest weight loss, but there was no significant difference compared with other groups. There was no significant difference between the compounds 1-13, 3-7 and Filgotinib groups, and the body weights thereof are changed in a basically same way (see specific values in Table 3-6), suggesting that the compound does not have much effect on the weight of mice.

TABLE 3-6*

Average body weight in the present application

| Date | G2 Blank group | G3 Dex | G6 Compound1-13 | G7 Compound3-7 | G8 Filgotinib | G1 Normal |
|---|---|---|---|---|---|---|
| 21 | 22.38 ± 0.23 | 22.41 ± 0.26 | 22.38 ± 0.30 | 22.59 ± 0.27 | 22.63 ± 0.27 | 22.30 ± 1.10 |
| 24 | 21.89 ± 0.67 | 22.36 ± 0.20 | 22.33 ± 0.37 | 22.66 ± 0.28 | 22.50 ± 0.33 | 23.00 ± 1.07 |
| 27 | 21.96 ± 0.63 | 22.35 ± 0.25 | 21.99 ± 0.44 | 22.10 ± 0.33 | 22.25 ± 0.32 | 23.22 ± 1.11 |
| 28 | 22.14 ± 0.56 | 22.43 ± 0.26 | 22.08 ± 0.51 | 22.36 ± 0.30 | 22.30 ± 0.35 | 23.12 ± 1.12 |
| 29 | 21.89 ± 0.47 | 21.51 ± 0.23 | 21.59 ± 0.41 | 22.26 ± 0.38 | 21.95 ± 0.40 | 23.30 ± 1.15 |
| 31 | 21.64 ± 0.48 | 21.24 ± 0.23 | 21.80 ± 0.58 | 22.40 ± 0.42 | 21.61 ± 0.49 | 23.78 ± 1.17 |
| 34 | 22.21 ± 0.54 | 20.71 ± 0.26 | 22.18 ± 0.53 | 22.25 ± 0.49 | 21.46 ± 0.57 | 23.70 ± 1.24 |
| 36 | 22.40 ± 0.52 | 21.28 ± 0.20 | 22.53 ± 0.47 | 22.46 ± 0.42 | 21.84 ± 0.61 | 24.26 ± 1.36 |
| 38 | 21.79 ± 0.44 | 19.91 ± 0.20 | 22.09 ± 0.40 | 21.88 ± 0.49 | 20.88 ± 0.54 | 23.56 ± 1.32 |
| 41 | 23.06 ± 0.49 | 20.84 ± 0.30 | 22.99 ± 0.34 | 22.59 ± 0.43 | 22.30 ± 0.52 | 24.24 ± 1.42 |

*Note:
average body weight ± standard error

Conclusion: In the collagen-induced mice arthritis (CIA) model, the compounds according to the present application showed a good therapeutic effect on the disease, with no significant effect on the body weight of mice, and has better in vivo efficacy than Filgotinib at the same dose.

Experiment 4: In Vivo Efficacy Study of Adjuvant Induced Arthritis (AIA)

Experimental Purpose:

Adjuvant induced arthritis (AIA) rat model is one of the commonly used animal models in rheumatoid arthritis disease research and new drug development. Its pathogenesis and clinical symptoms are similar to those of human rheumatoid arthritis. The model is established by injecting *Mycobacterium tuberculosis* into the footpad to induce immune cells and antibodies with bone and joint damage functions, which caused a systemic response manifested as joint swelling, osteolysis, synovial damage and other symptoms similar to human rheumatoid arthritis. The purpose of this experiment is to evaluate the therapeutic effect of compound 1-13 on adjuvant-induced arthritis rat model by using dexamethasone and filgotinib as reference compounds. There are 8 groups in this experiment, namely the normal group (Normal group), the solvent control group (Vehicle group), compound 1-13 1 mg/kg BID, 3 mg/kg BID, 10 mg/kg BID and 30 mg/kg BID dose groups, the positive drug dexamethasone 0.3 mg/kg QD group and the reference compound Filgotinib 30 mg/kg BID group. Except for the normal group, all the rats were injected with Freund's complete adjuvant subcutaneously into the left foot on day 0 to induce arthritis. According to the experimental protocol, groups were grouped according to body weight and scores, and the administration was started on the 13th day, which continued for 14 days. During the experiment, the body weight, feet volume (measured three times a week after the 13th day) and clinical score of the rats were monitored. At the end of the experiment, the right hind feet of rats were collected for hematoxylin-eosin staining (HE) staining for pathological score analysis.

Experimental Method:

1. Arthritis Model

Adjuvant preparation: 100 mg of *Mycobacterium tuberculosis* H37Ra were weighted, ground for about 5 minutes, added with 3 mL of paraffin oil to dissolve the powder, and transferred to a brown dispensing bottle. The mortar was washed twice with 3 mL and 4 mL of paraffin oil, and all the oil were transferred into the brown dispensing bottle, which had a final concentration of 10 mg/mL. The solution was broken by ultrasonic wave in an ice-water mixture for about 30 minutes.

2. Induction of Arthritis

The prepared adjuvants were homogenized under shaking, and removed of air bubbles by drawing with a 1 mL glass syringe (20 G needle), and then a 25 G needle. The rats were anesthetized with isoflurane. Before immunization, the syringe was turned upside down, so that the *Mycobacterium tuberculosis* was thoroughly mixed. After anesthesia, 0.1 mL of adjuvant was injected subcutaneously into the sole of the left foot of the rat. The day of the injection of 0.1 mL of paraffin oil subcutaneously in the soles of the rats in the normal group was the 0th day.

3. Administration

On the 13th day, all the animals showed symptoms of arthritis such as erythema or swelling of the feet, and they were stratified and randomly grouped according to score, foot size and weight. The grouping was shown in Table 9. 70 rats were divided into 7 groups, 10 rats in each group, and 5 rats in the normal group. According to Table 4-1, the dosage of each group is as follows. The intragastric administration volume was 5 mL/kg. Compound was administered twice a day for a total of 14 days.

TABLE 4-1

Grouping and dosage design

| Group | Test drugs | Number | Administration | Concentration mg/mL | Dosage mg/kg | Administration frequency |
|---|---|---|---|---|---|---|
| G1 | Normal | 5 | N/A | N/A | N/A | N/A |
| G2 | Vehicle | 10 | p.o. | N/A | N/A | bid, 14 days |
| G3 | Dex. | 10 | po | 0.06 | 0.3 | qd, 14 days |
| G4 | Filgotinib | 10 | p.o. | 6 | 30. | bid, 14 days |
| G5 | Compound1-13 | 10 | p.o. | 0.2 | 1 | bid, 14 days |
| G6 | Compound1-13 | 10 | p.o. | 0.6 | 3 | bid, 14 days |
| G7 | Compound1-13 | 10 | p.o. | 2 | 10 | bid, 14 days |
| G8 | Compound1-13 | 10 | p.o. | 6 | 30 | bid, 14 days |

4. Determination of the Incidence of Arthritis

Weight: the rats were weighed for three times a week from day 13 to day 27.

Foot volume: it was measured once before immunization, three times a week from the 13th day to the 27th day.

Scoring: the scoring was performed for three times a week from the 13th day to the 27th day. According to the different degrees of the lesions (redness, joint deformation) and the standard of 0-4 points, the highest score for each limb is 4 points, and the highest score for each animal is 12 points (except for the left hind limb on the injection side). The scoring standards are shown in Table 4-2.

TABLE 4-2

Clinical scoring criteria of arthritis

| Scores | Clinical symptoms |
|---|---|
| 0 | No erythema and swelling |
| 1 | Erythema or slight swelling on tarsal bone nearby or ankle or metatarsal bone, or erythema and swelling on one toe |
| 2 | Slight erythema and swelling on ankle and metatarsal bone, erythema and swelling on two or more toes |
| 3 | Moderate erythema and swelling on ankles, wrist joints and metatarsal bone |
| 4 | Severe swelling on all of ankles, wrist joints, metatarsal bone and toes |

5. Pathological Analysis

On day 27, the rats were euthanized. After blood collection, the right hind leg of the rat was taken, soaked in 10% formalin solution, decalcified with formic acid solution, embedded in paraffin, sectioned, HE stained, and observed under microscope. The degree of joint damage was evaluated from four aspects: inflammatory cell infiltration, pannus formation, cartilage injury and bone resorption, and scored according to the 0-4 points standard. The scoring standards are as follows (Table 4-3)

TABLE 4-3

Standard for pathology score of arthritis

| Lesion | Lesion characteristics | Score |
|---|---|---|
| inflammatory cell infiltration | There was no inflammatory cells observed; | 0 |
| | The subsynovial cells were fibrotic with minimal cellularinfiltration; | 1 |
| | Synovial cells proliferated with a small number of mononuclear cells infiltrated; | 2 |
| | Synovial cell proliferation, a large number of monocytes, plasma cells, lymphocytes infiltrated; | 3 |
| | A large number of inflammatory cell infiltrated around tire joint, tissue fibrosis, synovial thickening; | 4 |
| Pannus formation | No pannus formation were observed; | 0 |
| | There was very little pannus formation in the margin of cartilage; | 1 |
| | There was a proliferation of intercartilaginous fibrous tissue with a small amount of pannus formation at the joint margin; | 2 |
| | Pannus formation was present on 50% of articular cartilage; | 3 |
| | Pannus formation was observed throughout the articular cartilage; | 4 |
| cartilage injury | No cartilage injury was observed; | 0 |
| | Articular chondrocytes proliferated; | 1 |
| | The chondrocyte matrix was lost and a small number of chondrocytes were destroyed; | 2 |
| | There was a proliferation of fibrous tissue around the joint and a large number of chondrocytes are destroyed; | 3 |
| | There was a lot of fibrous tissue hyperplasia between articular cartilage, cartilage erosion; | 4 |
| Bone resorption | No bone resorption was observed; | 0 |
| | Minimal bone resorption was observed at the synovial margin; | 1 |
| | A small number of osteoclasts can be formed in small areas of bone tissue; | 2 |
| | Local subarticular cartilage bone tissue with bone resorption; | 3 |
| | Bone resorption in large areas of bone tissue with cartilage erosion; | 4 |

6. Statistical Processing

The experimental data is expressed by Mean±Standard Error (Mean±SEM), and weight, clinical score, and pathology score are expressed by One-way ANOVA, and p<0.5 is considered to be significant Experimental Results:

1. Clinical Scoring

Figure 5:
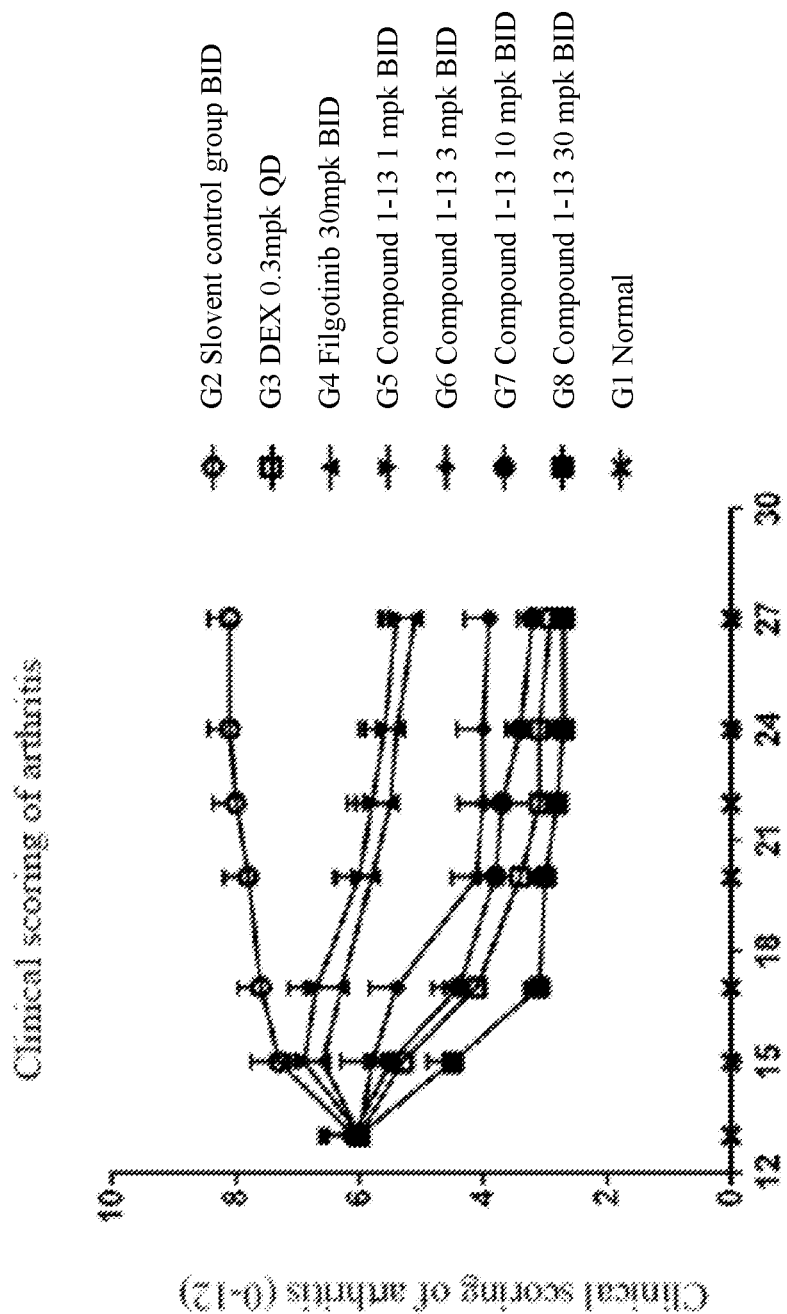
FIG. 5 Clinical scoring of rate with arthritis.

This experiment evaluated the improvement effect of compound 1-13 on clinical scores in a rat arthritis (AIA) model by using dexamethasone and Filgotinib as references. Rats began to develop arthritis symptoms on the 6th day after adjuvant immunization. The administration started on the 13th day, and the average clinical score of the solvent control group gradually increased. Experimental results showed that the average clinical score of the solvent control group reached a peak on the 24th day and were stabilized at about 8 points, indicating the successful establishment of the AIA model (FIG. 5, Table 4-4).

At the end of the experiment (day 27), compound 1-13 at four doses of 1, 3, 10, and 30 mg/kg significantly inhibited the clinical score of arthritic rats (compared with the solvent control group, p values are all <0.0001), and the clinical scores of arthritic rats were reduced to 5.4, 3.9, 3.2 and 2.7, respectively, in a dose-dependent manner (compared with the high-dose group and the low-dose group, p<0.0001). Among them, the effect of compound 1-13 at 30 mg/kg is the most obvious (starting from day 17, there is a very significant difference compared with the solvent control group, p<0.0001). The average arthritis clinical score of this group is 6.0 from the peak on day 13, dropped to 2.7 points on the 27th day of the experimental end point (FIG. 5, Table 12). The score of the reference compound Filgotinib 30 mg/kg BID dropped to 5.1 on the 27th day of the experimental end point, which was significantly lower than the solvent control group (p<0.001) but significantly higher than compound 1-13 30 mg/kg BID (p<0.001). The improvement effect of compound 1-13 on the clinical score of arthritis was significantly better than the effect of Filgotinib at the same dosage.

The average clinical score of the positive control dexamethasone treatment group reached the highest value of 6.0 after the 13th day. After the administration, the clinical score continued to decline and dropped to 2.7 at the experimental end point on the 27th day. Compared with the control group, there is a very significant difference (FIG. 5, Table 4-4).

2. Feet Volume

Figure 6:
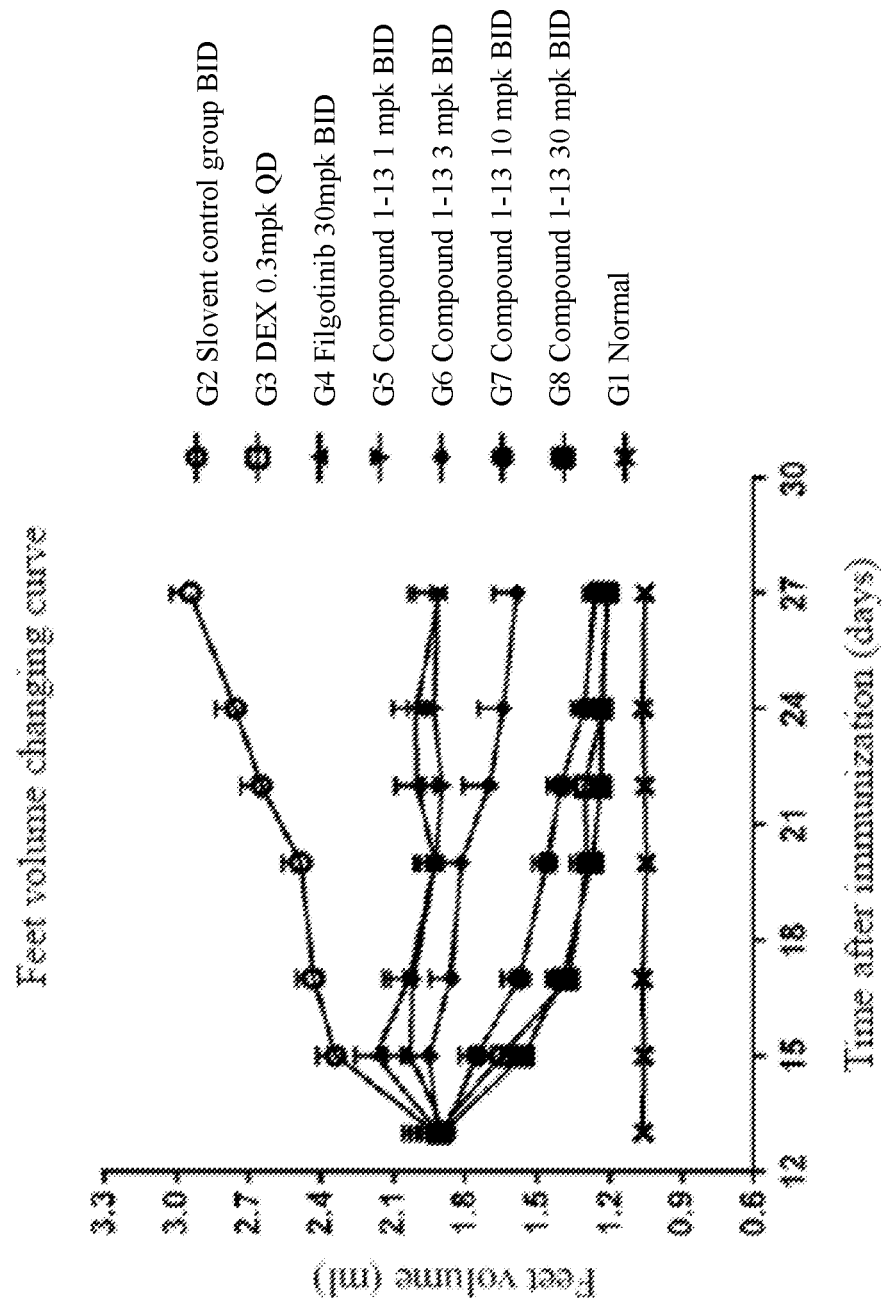
FIG. 6 Feet volume changing curve of rate with arthritis.

This experiment evaluated the effect of compound 1-13 on foot volume in a rat arthritis (AIA) model, with dexamethasone and Filgotinib as references. The average foot volume of animals in the solvent control group increased steadily from 1.9 mL on day 13 to 2.9 mL at the end of the experiment on day 27, marking the successful establishment of the AIA model (FIG. 6, Table 4-5). At the end of the experiment, compound 1-13 at the doses of 1, 3, 10 and 30 mg/kg can significantly inhibit the increase in foot volume of arthritic rats (compared with the solvent control group, all p values are <0.0001). The mean foot volume of inflammatory rats was reduced to 1.59 mL, 1.26 mL and 1.21 mL, respectively, in a dose-dependent manner (compared between the high-dose group and the low-dose group, p<0.0001). Reference compound Filgotinib 30 mg/kg BID On the 27th day of the end of the experiment, the foot volume decreased to 1.91 points, which was significantly lower than the solvent control group (p<0.0001) but significantly higher than that of compound 1-13. 30 mg/kg BID (p<0.0001) compound 1-13 on rats. The effect of improving foot volume is significantly better than that of Filgotinib at the same dosage. The positive control dexamethasone treatment group also suppressed the increase in average foot volume very well. After the administration, the foot volume steadily decreased until the end of the experiment, which was stabilized on day 17 and was significantly different from the solvent control group, P<0.0001 (FIG. 6, Table 4-5).

3. Weight

Figure 7:
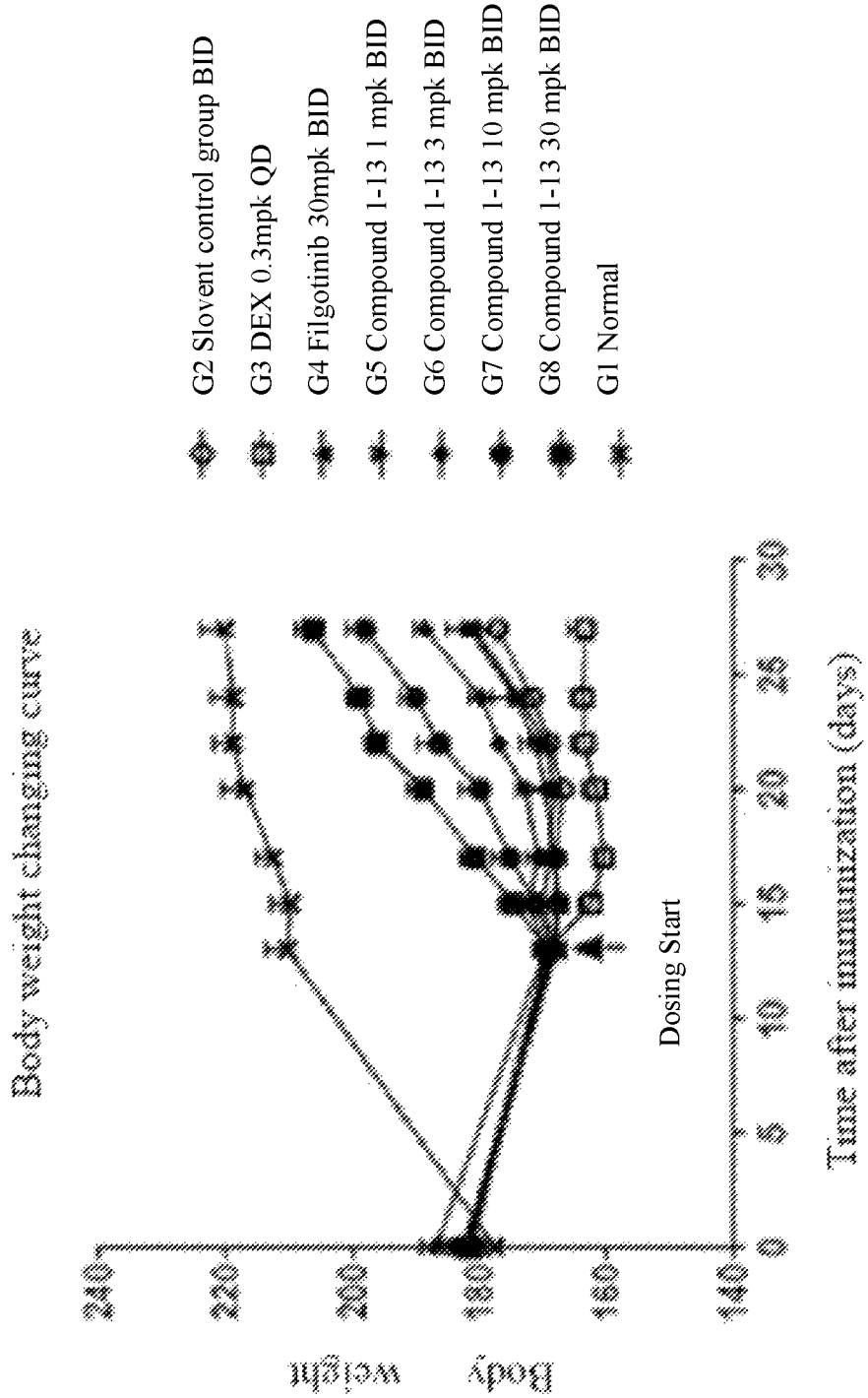
FIG. 7 Body weight changing curve of rate with arthritis.

Compared with the normal group, the body weight of the rats was reduced after immunizing and modeling. After the start of administration on the 13th day, the body weight of each administration group increased slowly and continuously compared with the solvent control group, while the weight of the positive control dexamethasone group recovered more slowly, which suggests that the rats tolerate Filgotinib and compound 1-13 well. The body weight of the compound 1-13 30 mg/kg group increased the fastest, and the body weights for 4 dosages were increased in a dose-dependent manner (FIG. 7 and Table 4-6).

4 Histopathological Test Results

Arthritis rats in the solvent control group had a total pathological score of 16±0.00, and for those administrated with compound 1-13 at a dose of 1 mg/kg, the score decreased to 13.3±0.44 (compared with the solvent control group, P=0.09, no statistical difference), with an inhibition rate of 16.9%; while the 3 mg/kg, 10 mg/kg and 30 mg/kg doses can significantly reduce the pathological scores of arthritic rats to 11.3±1.64, 4.4±1.16 and 1.6±0.47, respectively, with p values of 0.014, <0.0001 and <0.0001, and inhibition rate of 29.4%, 72.5% and 90%. The reference compound Filgotinib 30 mg/kg had a total pathological score of 15.2±0.49, and the inhibition rate was 5%. There was no significant difference compared with the solvent group. Compound 1-13 at the same dose (30 mg/kg) has a total pathological score of significantly lower than Filgotinib (p<0.0001). The control compound dexamethasone at 0.3 mg/kg dose extremely significantly reduced the pathological score of arthritic rats to 4.4 0.8, p value<0.0001, inhibition rate 72.5% (Table 4-7).

TABLE 4-4

Clinical scoring

| Days | Normal group | | Solvent control group | | dexamethasone acetate group (0.3 mg/kg) | | Filgotinib (30 mg/kg) | | Compound1-13 (1 mg/kg) | |
|---|---|---|---|---|---|---|---|---|---|---|
| | Average | Standard error | Average | Standard error | Average | Standard error | Average | Standard error | Average | Standard error |
| 13 | 0.0 | 0.0 | 6.1 | 0.5 | 6.0 | 0.5 | 6.0 | 0.6 | 6.0 | 0.5 |
| 15 | 0.0 | 0.0 | 7.3 | 0.4 | 5.3* | 0.5 | 6.6 | 0.5 | 6.9 | 0.5 |
| 17 | 0.0 | 0.0 | 7.6 | 0.4 | 4.1**** | 0.5 | 6.3 | 0.6 | 6.7 | 0.4 |
| 20 | 0.0 | 0.0 | 7.8 | 0.4 | 3.4**** | 0.5 | 5.8** | 0.6 | 6.0* | 0.4 |
| 22 | 0.0 | 0.0 | 8.0 | 0.4 | 3.1**** | 0.5 | 5.5*** | 0.6 | 5.8** | 0.4 |

TABLE 4-4-continued

| | | | | Clinical scoring | | | | | |
|---|---|---|---|---|---|---|---|---|---|
| 24 | 0.0 | 0.0 | 8.1 | 0.3 | 3.1**** | 0.5 | 5.4**** | 0.5 | 5.6*** | 0.4 |
| 27 | 0.0 | 0.0 | 8.1 | 0.3 | 2.9**** | 0.5 | 5.1**** | 0.5 | 5.4**** | 0.3 |

| | Compound1-13 (3 mg/kg) | | Compound1-13 (10 mg/kg) | | Compound1-13 (30 mg/kg) | |
|---|---|---|---|---|---|---|
| Days | Average | Standard error | Average | Standard error | Average | Standard error |
| 13 | 6.0 | 0.6 | 6.1 | 0.5 | 6.0 | 0.5 |
| 15 | 5.8 | 0.5 | 5.5* | 0.4 | 4.5*** | 0.4 |
| 17 | 5.4** | 4.4 | 4.4**** | 0.4 | 3.1**** | 0.2 |
| 20 | 4.1**** | 3.8 | 3.8**** | 0.2 | 3.0**** | 0.2 |
| 22 | 4.0**** | 3.7 | 3.7**** | 0.3 | 2.8**** | 0.2 |
| 24 | 4.0**** | 3.4 | 3.4**** | 0.2 | 2.7**** | 0.2 |
| 27 | 3.9**** | 3.2 | 3.2**** | 0.1 | 2.7**** | 0.2 |

*$p < 0.05$,
**$p < 0.01$,
***$p < 0.001$,
****$p < 0.0001$ vs. Solvent control group, one-way ANOVA.

TABLE 4-5

| | Feet volume | | | | | | | | | |
|---|---|---|---|---|---|---|---|---|---|---|
| | Normal group | | Solvent control group | | dexamethasone acetate group (0.3 mg/kg) | | Filgotinib (30 mg/kg) | | Compound1-13 (1 mg/kg) | |
| Days | Average | Standard error | Average | Standard error | Average | Standard error | Average | Standard error | Average | Standard error |
| 13 | 1.1 | 0.0 | 1.9 | 0.1 | 1.9 | 0.1 | 1.9 | 0.1 | 1.9 | 0.1 |
| 15 | 1.1 | 0.0 | 2.3 | 0.1 | 1.7**** | 0.1 | 2.2 | 0.1 | 2.0 | 0.1 |
| 17 | 1.1 | 0.0 | 2.4 | 0.1 | 1.4**** | 0.1 | 2.0** | 0.1 | 2.0** | 0.1 |
| 20 | 1.0 | 0.0 | 2.5 | 0.1 | 1.3**** | 0.1 | 1.9**** | 0.1 | 1.9**** | 0.1 |
| 22 | 1.1 | 0.0 | 2.6 | 0.1 | 1.3**** | 0.1 | 2.0**** | 0.1 | 1.9**** | 0.1 |
| 24 | 1.1 | 0.0 | 2.8 | 0.1 | 1.2**** | 0.1 | 2.0**** | 0.1 | 1.9**** | 0.1 |
| 27 | 1.1 | 0.0 | 2.9 | 0.1 | 1.2**** | 0.1 | 1.9**** | 0.1 | 1.9**** | 0.1 |

| | Compound1-13 (3 mg/kg) | | Compound1-13 (10 mg/kg) | | Compound1-13 (30 mg/kg) | |
|---|---|---|---|---|---|---|
| Days | Average | Standard error | Average | Standard error | Average | Standard error |
| 13 | 1.9 | 0.1 | 1.9 | 0.1 | 1.9 | 0.1 |
| 15 | 2.0* | 0.1 | 1.8*** | 0.1 | 1.6**** | 0.1 |
| 17 | 1.9**** | 0.1 | 1.6**** | 0.1 | 1.4**** | 0.1 |
| 20 | 1.8**** | 0.1 | 1.5**** | 0.1 | 1.3**** | 0.1 |
| 22 | 1.7**** | 0.1 | 1.4**** | 0.1 | 1.2**** | 0.0 |
| 24 | 1.6**** | 0.1 | 1.3**** | 0.1 | 1.2**** | 0.0 |
| 27 | 1.6**** | 0.1 | 1.3**** | 0.1 | 1.2**** | 0.0 |

*$p < 0.05$,
**$p < 0.01$,
***$p < 0.001$,
****$p < 0.0001$ vs. Solvent control group, one-way ANOVA.

TABLE 4-6

| | Body weight | | | | | | | | | |
|---|---|---|---|---|---|---|---|---|---|---|
| | Normal group | | Solvent control group | | dexamethasone acetate group (0.3 mg/kg) | | Filgotinib (30 mg/kg) | | Compound1-13 (1 mg/kg) | |
| Days | Average | Standard error | Average | Standard error | Average | Standard error | Average | Standard error | Average | Standard error |
| 0 | 177.6 | 2.0 | 182.0 | 2.3 | 182.2 | 2.7 | 182.7 | 2.9 | 182.0 | 1.6 |
| 13 | 210.2 | 3.4 | 168.1 | 3.3 | 169.1 | 2.5 | 168.0 | 3.0 | 168.0 | 1.3 |

TABLE 4-6-continued

| | | | | Body weight | | | | | |
|---|---|---|---|---|---|---|---|---|---|
| 15 | 209.8 | 3.1 | 167.7 | 3.1 | 162.4 | 2.1 | 167.5 | 2.9 | 170.1 | 2.0 |
| 17 | 212.5 | 2.7 | 168.0 | 3.0 | 160.5 | 1.5 | 168.3 | 3.0 | 168.9 | 1.5 |
| 20 | 216.9 | 3.7 | 166.9 | 3.0 | 161.6 | 2.2 | 169.7 | 2.8 | 168.1 | 1.5 |
| 22 | 218.8 | 3.1 | 168.9 | 3.0 | 163.5 | 2.2 | 171.2 | 2.6 | 169.6 | 1.4 |
| 24 | 218.7 | 3.5 | 171.7 | 2.7 | 163.7 | 2.0 | 174.3 | 3.7 | 173.6 | 1.8 |
| 27 | 220.1 | 3.7 | 177.2 | 2.8 | 163.4** | 2.7 | 181.7 | 3.5 | 180.9 | 1.8 |

| | Compound1-13 (3 mg/kg) | | Compound1-13 (10 mg/kg) | | Compound1-13 (30 mg/kg) | |
|---|---|---|---|---|---|---|
| Days | Average | Standard error | Average | Standard error | Average | Standard error |
| 0 | 187.0 | 2.2 | 181.6 | 2.2 | 181.2 | 2.3 |
| 13 | 169.6 | 1.4 | 168.5 | 2.5 | 169.3 | 2.2 |
| 15 | 172.3 | 1.5 | 171.1 | 2.7 | 174.8 | 2.2 |
| 17 | 170.9 | 1.7 | 175.2 | 2.7 | 180.6** | 2.4 |
| 20 | 172.8 | 1.5 | 179.9 | 3.3 | 188.9**** | 2.5 |
| 22 | 177.0 | 1.3 | 186.3**** | 3.5 | 196.0**** | 2.2 |
| 24 | 179.8 | 1.8 | 190.1**** | 2.5 | 198.8**** | 2.2 |
| 27 | 188.6* | 1.7 | 198.2**** | 2.9 | 206.3**** | 2.7 |

*$p < 0.05$,
**$p < 0.01$,
***$p < 0.001$,
****$p < 0.0001$ vs. Solvent control group, one-way ANOVA.

TABLE 4-7

Pathological Scoring

| | Pathology Scoring (mean value ± standard error) | | | | |
|---|---|---|---|---|---|
| Group | inflammatory cell infiltration | Pannus formation | articular injury | Bone resorption | Total score |
| Normal group | 0.0 ± 0.0 | 0.0 ± 0.0 | 0.0 ± 0.0 | 0.0 ± 0.0 | 0.0 ± 0.0 |
| Solvent control group | 4.0 ± 0.0 | 4.0 ± 0.0 | 4.0 ± 0.0 | 4.0 ± 0.0 | 16.0 ± 0.0 |
| dexamethasone acetate group (0.3 mg/kg) | 1.8 ± 0.2 | 1.4 ± 0.3 | 0.6 ± 0.2 | 0.6 ± 0.2 | 4.4 ± 9.8**** |
| Filgotinib (30 mg/kg) | 4.0 ± 0.0 | 3.9 ± 0.1 | 3.7 ± 0.2 | 3.6 ± 0.2 | 15.2 ± 0.5 |
| Compound1-13 (1 mg/kg) | 3.6 ± 0.3 | 3.5 ± 0.3 | 3.3 ± 0.4 | 2.9 ± 0.5 | 13.3 ± 1.4 |
| Compound1-13 (3 mg/kg) | 3.3 ± 0.3 | 3.2 ± 0.3 | 2.5 ± 0.5 | 2.3 ± 0.5 | 11.3 ± 1.6* |
| Compound1-13 (10 mg/kg) | 1.7 ± 0.3 | 1.4 ± 0.4 | 0.8 ± 0.3 | 0.5 ± 0.3 | 4.4 ± 1.2**** |
| Compound1-13 (30 mg/kg) | 0.6 ± 0.2 | 0.5 ± 0.2 | 0.3 ± 0.1 | 0.2 ± 0.1 | 1.6 ± 0.5**** |

*$p < 0.05$, ****$p < 0.001$, v.s. Solvent control group, One-way ANOVA.

Conclusion: The rats in the solvent control group showed clinical symptoms of arthritis and continued to worsen. Compared with the solvent control group, compounds 1-13 (1, 3, 10, 30 mg/kg), Filgotinib (30 mg/kg) and dexamethasone (0.3 mg/kg) showed a significant inhibit effect on adjuvant-induced arthritis, which is manifested by delayed onset time, and significantly reduced clinical symptoms and pathological changes, and compound 1-13 has a dose-dependent therapeutic effect on adjuvant-induced arthritis model. The above experimental results show that compound 1-13 has a significant therapeutic effect on adjuvant-induced arthritis in rats and the effect is better than Filgotinib.

The invention claimed is:

1. A compound of formula (I), isomers thereof or pharmaceutically acceptable salts thereof,

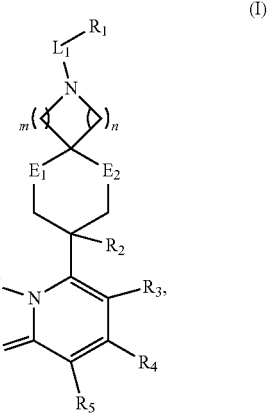

wherein,
$E_1$ and $E_2$ are independently selected from single bond, —$CH_2$— or —$(CH_2)_2$—;

$L_1$ is selected from single bond, —$(CH_2)_g$—, —C(=O)— or —C(=O)—$(CH_2)_h$—;

m is 1 or 2;

n is 1 or 2;

g is 1, 2 or 3;

h is 1, 2 or 3;

$R_1$ is selected from H, CN, $C_{1-6}$ alkyl group or 3~6-membered cycloalkyl group, wherein the above $C_{1-6}$ alkyl group and 3~6-membered cycloalkyl group are optionally substituted by 1, 2 or 3 $R_a$;

$R_2$ is selected from H, F, Cl, Br, I or $C_{1-3}$ alkyl groups, wherein the above $C_{1-3}$ alkyl group is optionally substituted by 1, 2 or 3 $R_b$;

$R_3$, $R_4$ and $R_5$ are independently selected from H, F, Cl, Br, I or $C_{1-3}$ alkyl group, wherein the above $C_{1-3}$ alkyl group is optionally substituted by 1, 2 or 3 $R_c$;

$R_6$, $R_7$ and $R_8$ are independently selected from H, F, Cl, Br, I or $C_{1-3}$ alkyl group, wherein the above $C_{1-3}$ alkyl group is optionally substituted by 1, 2 or 3 $R_d$;

Each $R_a$ is independently selected from H, F, Cl, Br, I, CN or $C_{1-3}$ alkyl group, wherein the above $C_{1-3}$ alkyl group is optionally substituted by 1, 2 or 3 R;

Each $R_b$ is independently selected from F, Cl, Br or I;

Each $R_c$ is independently selected from F, Cl, Br or I;

Each $R_d$ is independently selected from F, Cl, Br or I;

Each R is independently selected from F, Cl, Br or I; and wherein the isomers are selected from geometrical isomers, stereoisomers or tautomers.

2. The compound of formula (I), isomers thereof or pharmaceutically acceptable salts thereof according to claim 1, wherein each $R_a$ is independently selected from H, F, Cl, Br, I or CN.

3. The compound of formula (I), isomers thereof or pharmaceutically acceptable salts thereof according to claim 1, wherein, $R_1$ is selected from H, CN, $C_{1-3}$ alkyl group or 3~5-membered cycloalkyl group, wherein the $C_{1-3}$ alkyl group and 3~5-membered cycloalkyl group are optionally substituted by 1, 2 or 3 $R_a$.

4. The compound of formula (I), isomers thereof or pharmaceutically acceptable salts thereof according to claim 3, wherein $R_1$ is selected from H, CN, $CH_3$,

wherein the $CH_3$,

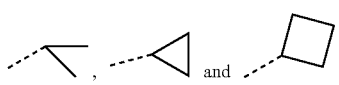

are optionally substituted by 1, 2 or 3 $R_a$.

5. The compound of formula (I), isomers thereof or pharmaceutically acceptable salts thereof according to claim 4, wherein, $R_1$ is selected from H, CN, $CF_3$, $CHF_2$,

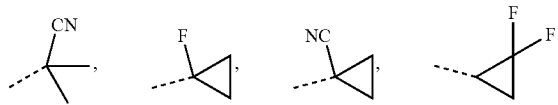

or 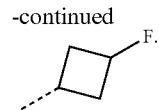

6. The compound of formula (I), isomers thereof or pharmaceutically acceptable salts thereof according to claim 1, wherein, $R_2$ is selected from H, F, Cl, Br or I.

7. The compound of formula (I), isomers thereof or pharmaceutically acceptable salts thereof according to claim 1, wherein, $R_3$, $R_4$ and $R_5$ are independently selected from H, F, Cl, Br or I.

8. The compound of formula (I), isomers thereof or pharmaceutically acceptable salts thereof according to claim 1, wherein, $R_6$, $R_7$ and $R_8$ are independently selected from H, F, Cl, Br or I.

9. The compound of formula (I), isomers thereof or pharmaceutically acceptable salts thereof according to claim 1, wherein, $L_1$ is selected from single bond, —$CH_2$—, —$(CH_2)_2$—, —C(=O)— or —C(=O)—$(CH_2)$—.

10. The compound of formula (I), isomers thereof or pharmaceutically acceptable salts thereof according to claim 1, wherein, structural unit

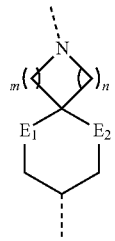

is selected from

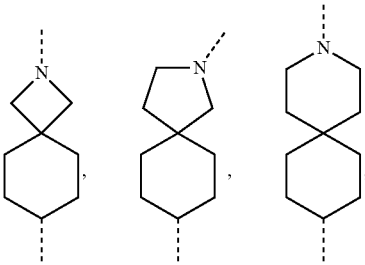

or 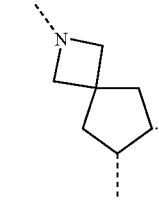

11. The compound of formula (I), isomers thereof or pharmaceutically acceptable salts thereof according to claim 1, wherein, structural unit

81
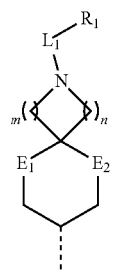
is selected from
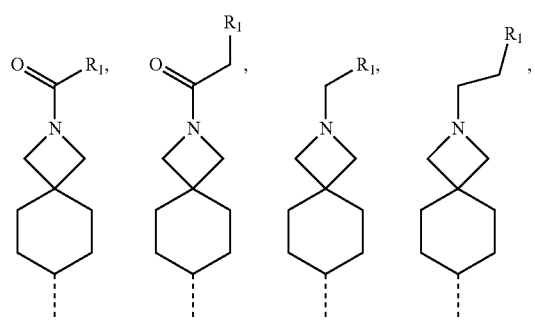
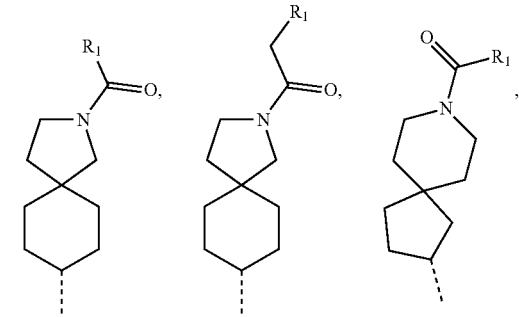
82
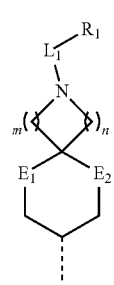
is selected from
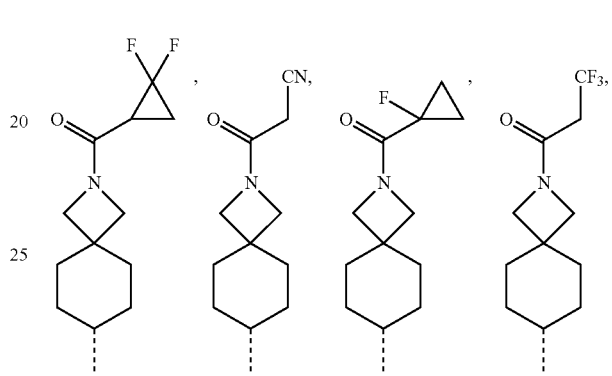
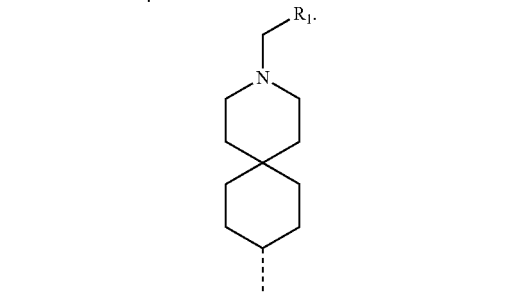
12. The compound of formula (I), isomers thereof or pharmaceutically acceptable salts thereof according to claim 1, wherein, structural unit

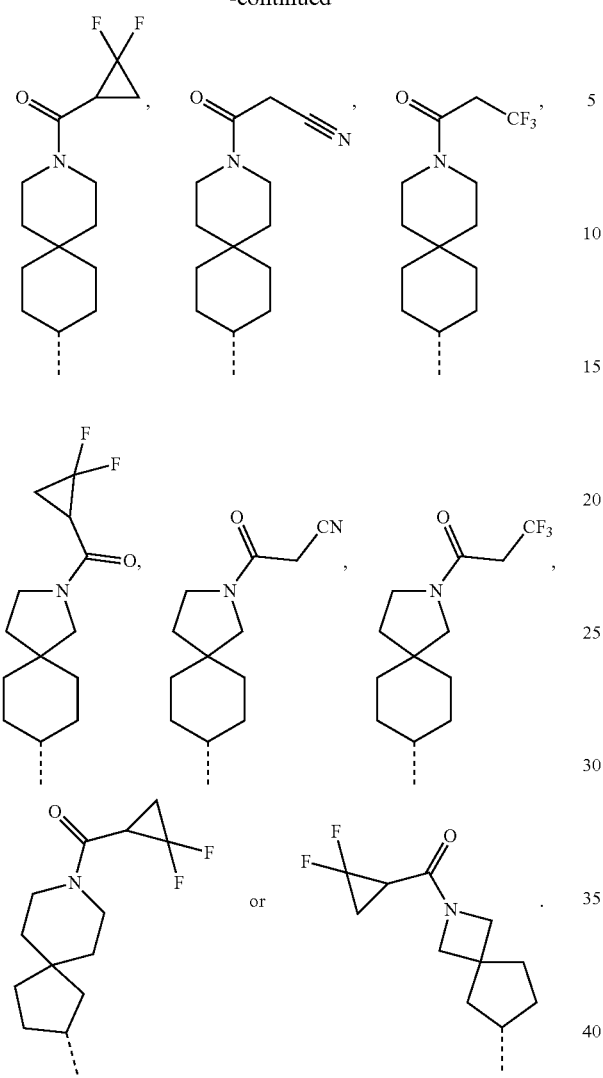
13. The compound of formula (I), isomers thereof or pharmaceutically acceptable salts thereof according to claim 1, wherein the compound is selected from the group consisting of:
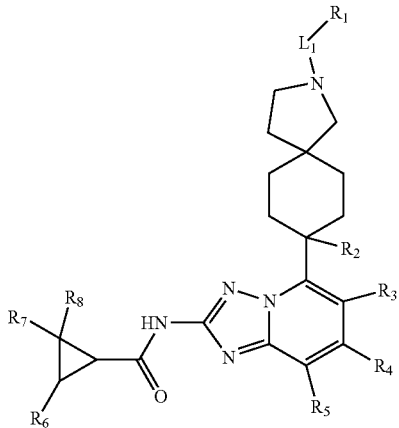
(I-2)
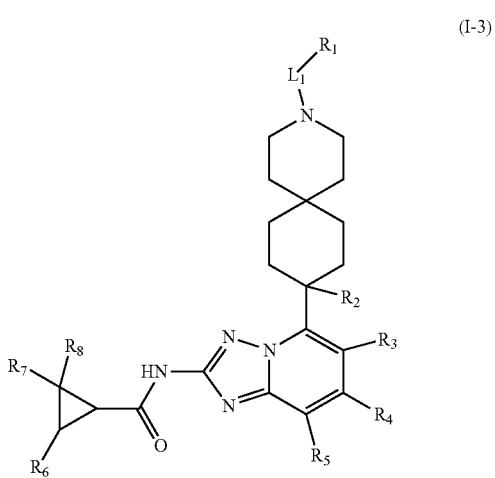
(I-3)
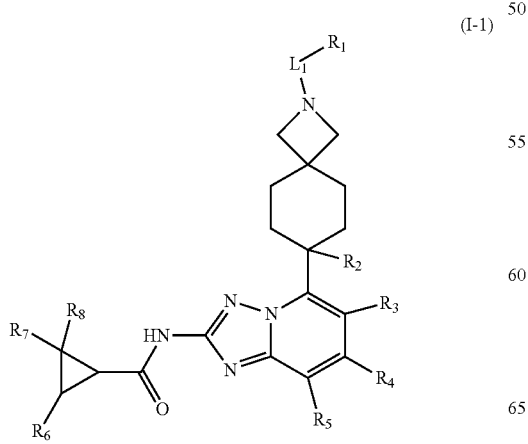
(I-1)
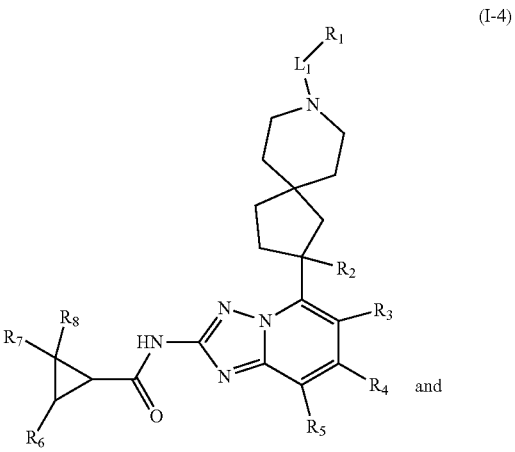
(I-4)
and

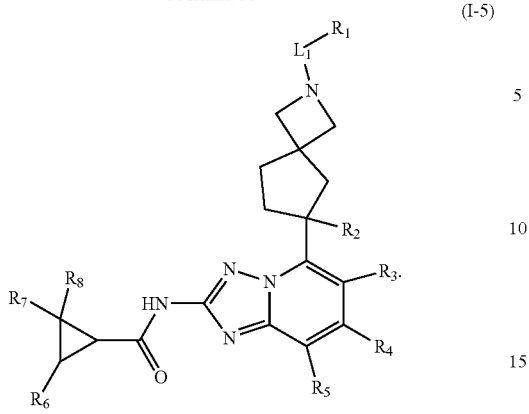
(I-5)
14. The compound of formula (I), isomers thereof or pharmaceutically acceptable salts thereof according to claim 13, wherein the compound is
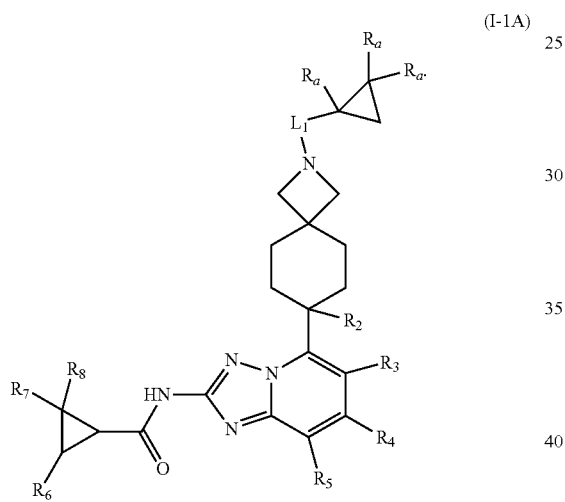
(I-1A)
15. A compound, isomers thereof or pharmaceutically acceptable salts thereof, wherein the compound is selected from the group consisting of:
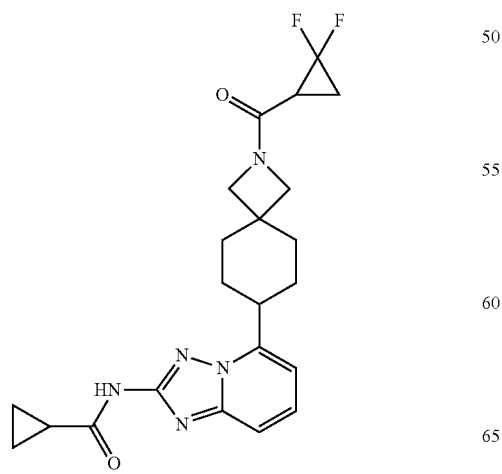
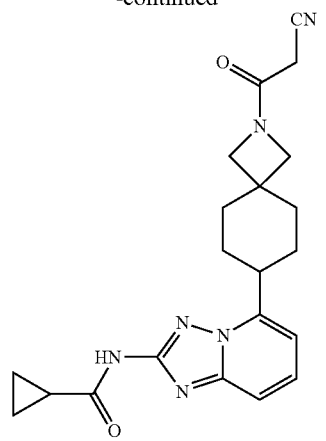
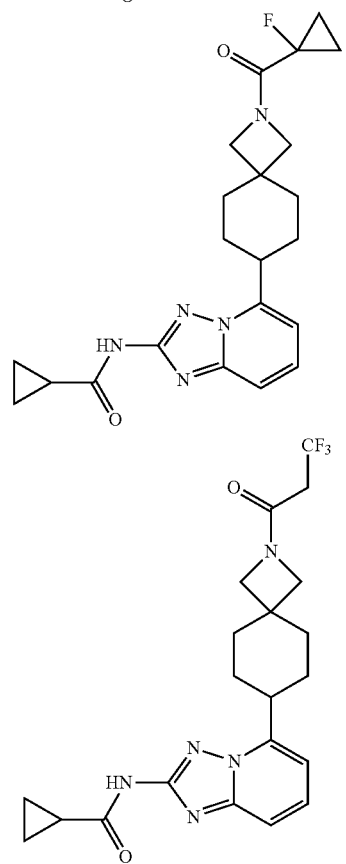
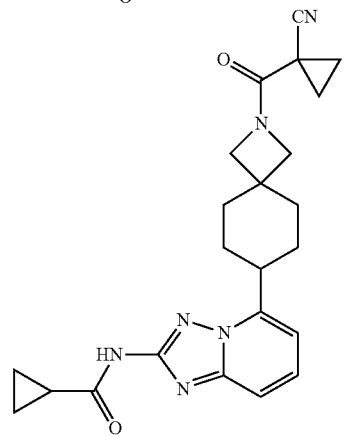

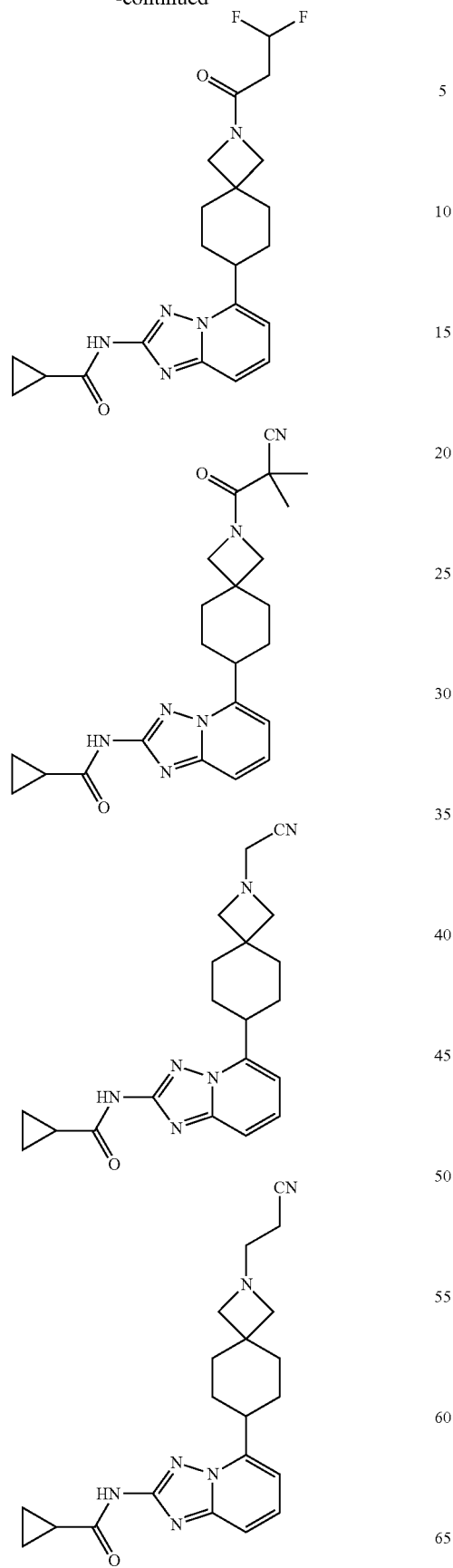
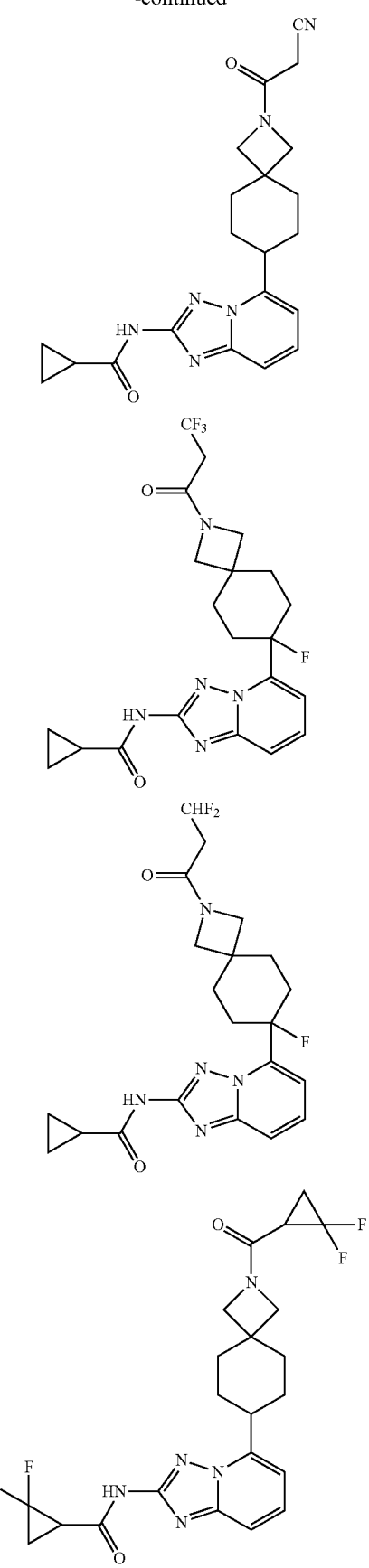

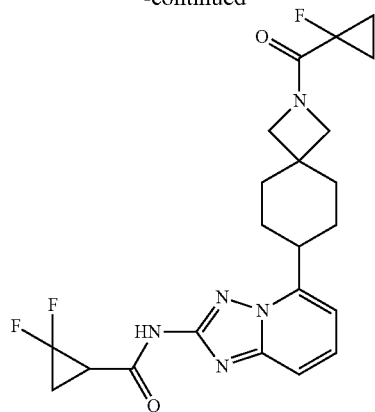
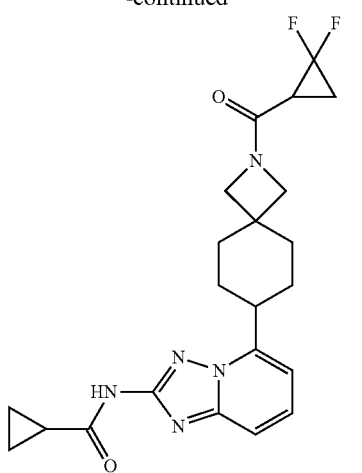

-continued
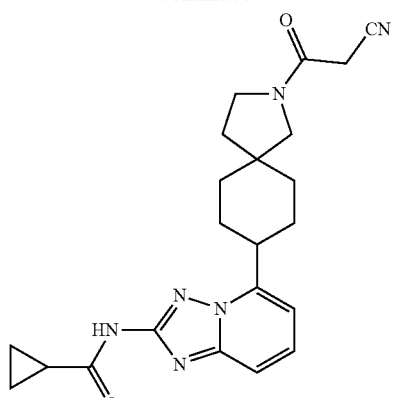
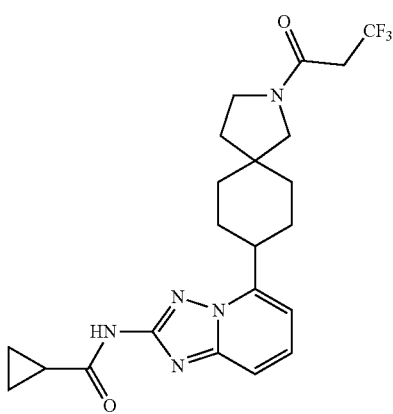
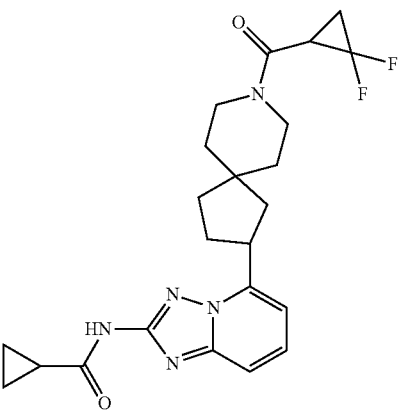
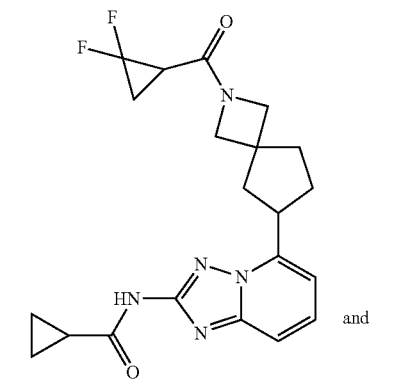
and
-continued
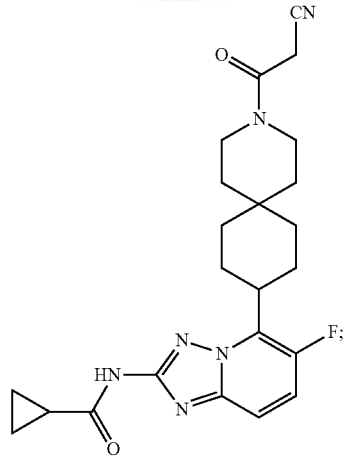
wherein the isomers are selected from geometrical isomers, stereoisomers or tautomers.
16. The compound, isomers thereof or pharmaceutically acceptable salts thereof according to claim 15, wherein the compound is selected from the group consisting of:
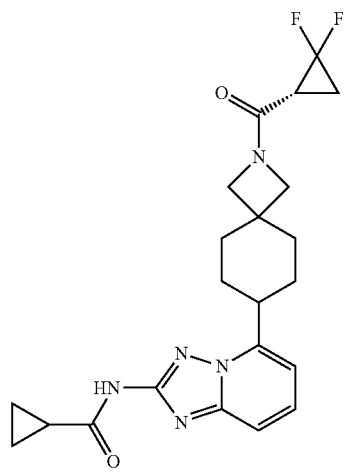
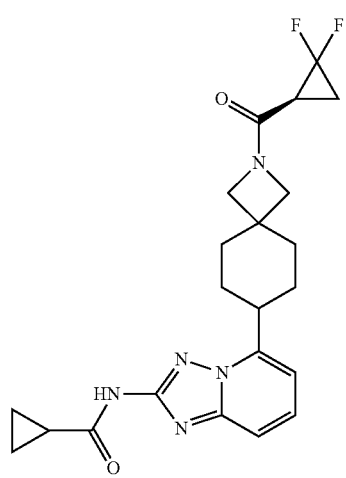

93
-continued
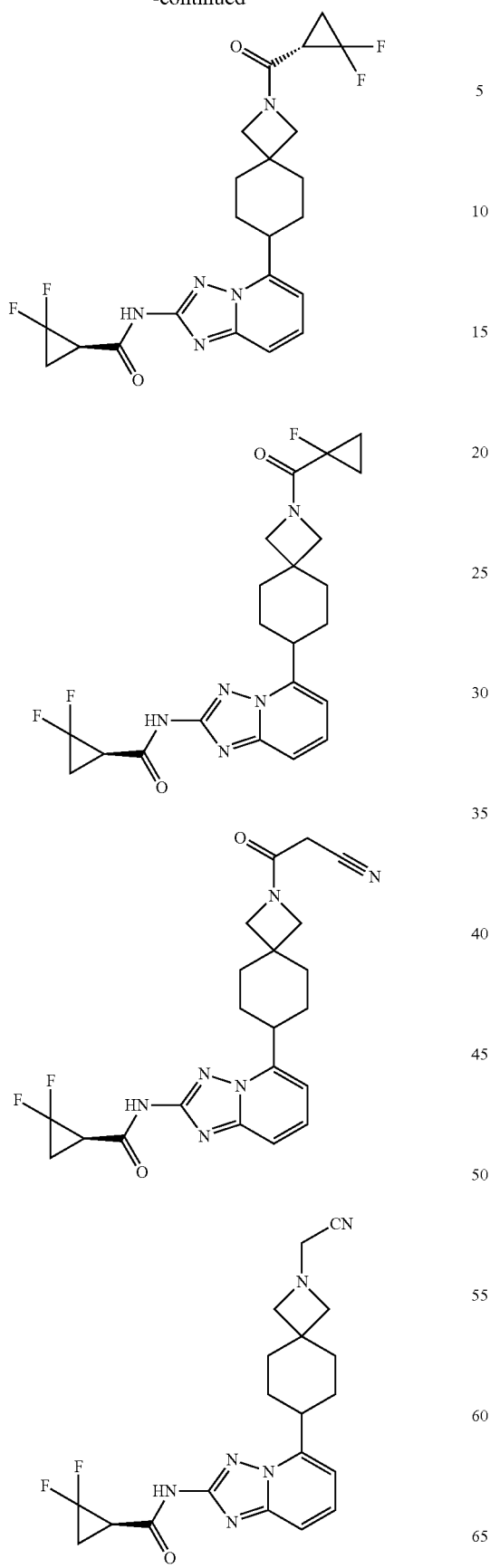
94
-continued
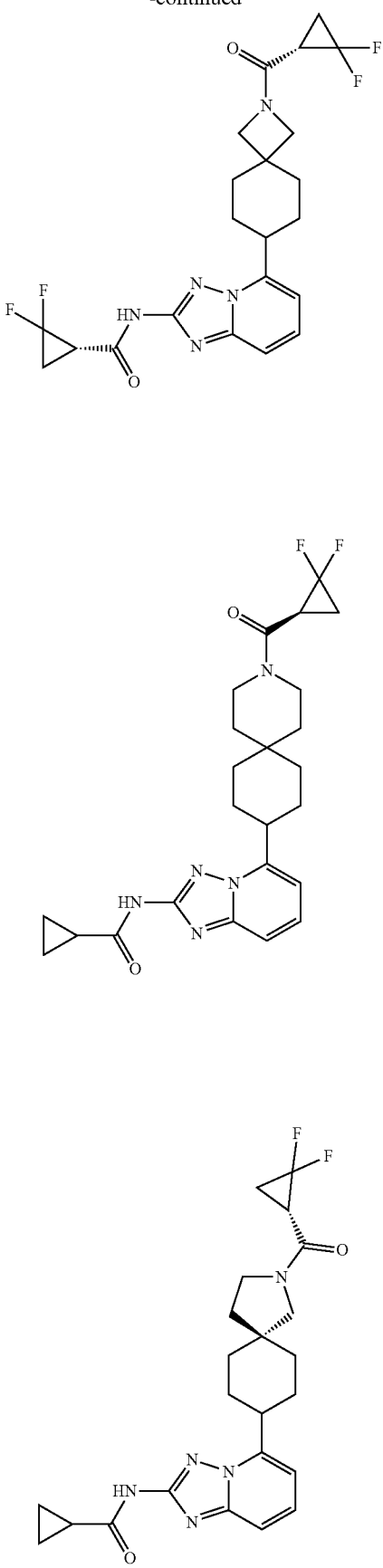

95
-continued
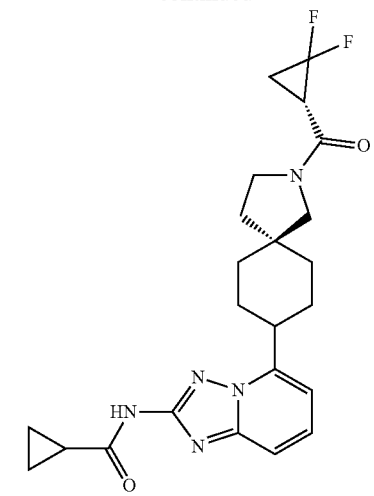
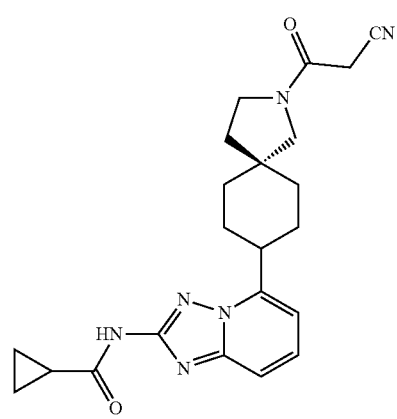
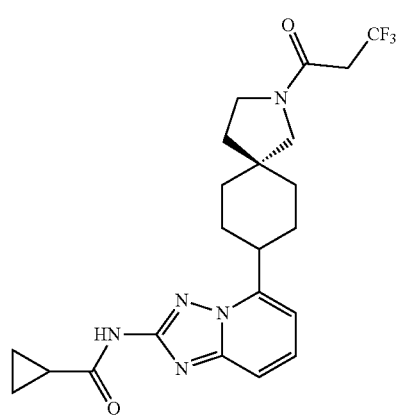
96
-continued
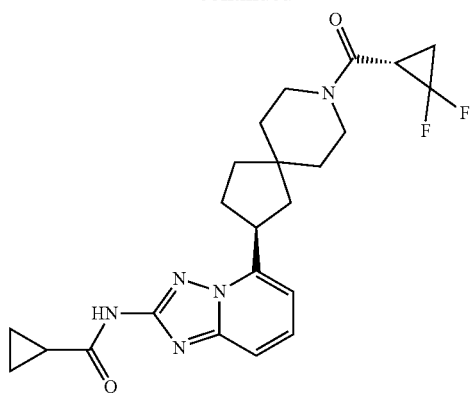
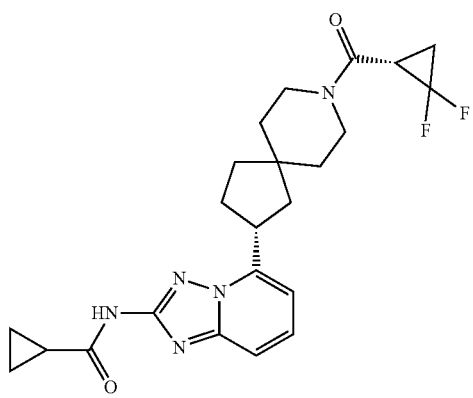
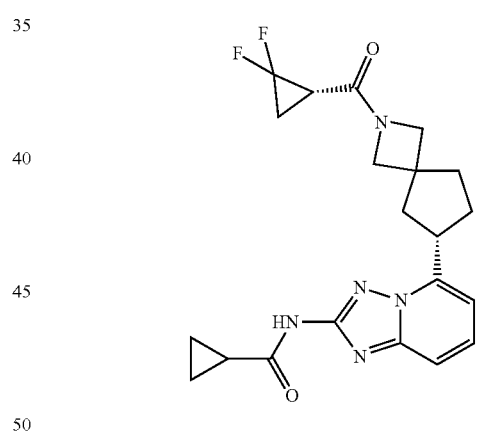
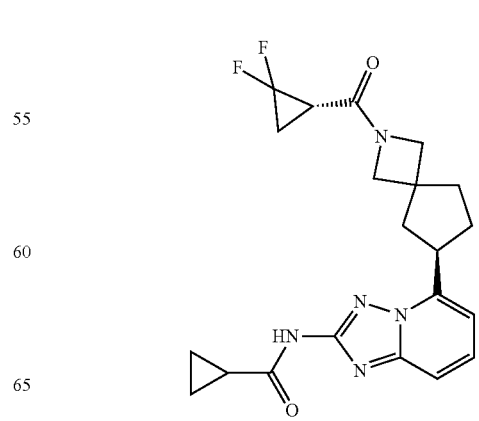

-continued

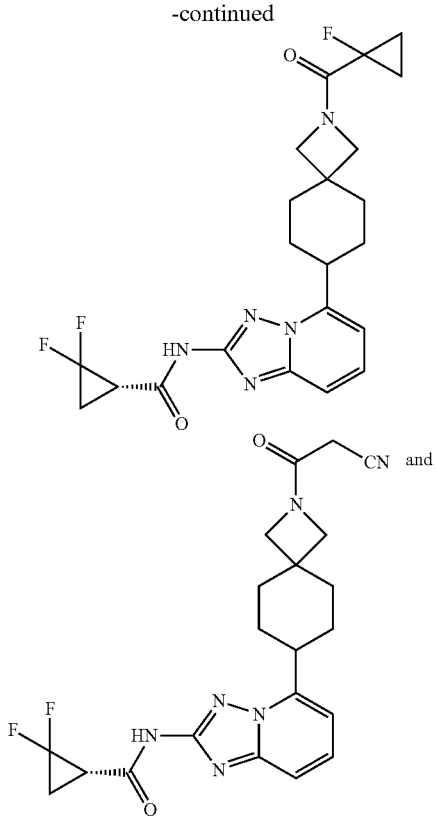

and

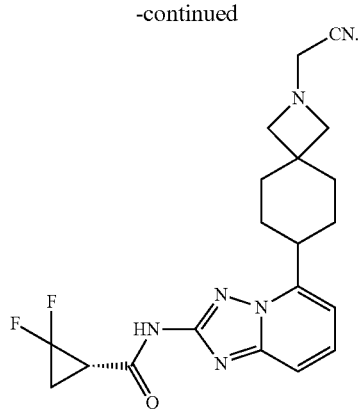

17. A pharmaceutical composition, comprising the compound, isomers thereof or pharmaceutically acceptable salts thereof according to claim 1 and a pharmaceutically acceptable carrier.

18. A method for treating JAK1 and/or TYK2 related diseases, comprising administering a compound, isomers thereof or pharmaceutically acceptable salts thereof according to claim 1.

19. The method according to claim 18, wherein the JAK1 and/or TYK2 related disease is rheumatoid arthritis.

* * * * *